United States Patent
Shair et al.

(10) Patent No.: US 7,045,360 B2
(45) Date of Patent: May 16, 2006

(54) METHOD FOR ANALYSIS OF REACTION PRODUCTS

(75) Inventors: Matthew D. Shair, Boston, MA (US); Gregory A. Korbel, Cambridge, MA (US); Gojko Lalic, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 827 days.

(21) Appl. No.: 09/778,708

(22) Filed: Feb. 7, 2001

(65) Prior Publication Data

US 2002/0090728 A1 Jul. 11, 2002

Related U.S. Application Data

(60) Provisional application No. 60/180,664, filed on Feb. 7, 2000.

(51) Int. Cl.
G01N 21/00 (2006.01)

(52) U.S. Cl. ........................ 436/166; 436/164; 436/800; 548/100; 548/416; 548/427; 548/455; 536/25.32

(58) Field of Classification Search ................. 436/166, 436/164, 800; 548/100, 416, 427, 455; 536/25.32
See application file for complete search history.

(56) References Cited

U.S. PATENT DOCUMENTS

| | | | |
|---|---|---|---|
| 4,847,385 A | 7/1989 | Kusakata et al. | 548/455 |
| 5,453,505 A | 9/1995 | Lee et al. | 544/124 |
| 5,627,027 A | 5/1997 | Waggoner et al. | 435/6 |
| 5,808,044 A | 9/1998 | Brush et al. | 536/25.32 |
| 6,545,164 B1 * | 4/2003 | Waggoner et al. | 548/427 |

OTHER PUBLICATIONS

Blaser, et al., "The Chiral Pool as a Source of Enantioselective Catalysts and Auxillaries", Chem. Rev. 92: 935–952, 1992.

Bromidge, et al., "A Parallel Combinatorial Approach to Locating Homochiral Lewis Acid Catalysts for the Asymmetric Aza–Diels–Alder Reaction of an Imino Dienophile", Tetrahedron Lett. 39: 8905–8908, 1998.

Burgess, et al., "New Catalysts and Conditions for a C–H Insertion Reaction Identified by High Throughput Catalyst Screening", Angew. Chem. Int. Ed. Engl. 35: 220–222. 1996.

Burgess, et al., "Application of Novel Phosphine Oxazoline Ligands in Asymmetric Allylations of 4–Acyloxy–2–Pentene Derivatives" Tetrahedron Asymmetry, 9: 2465–2469, 1998.

Carpino, et al., "Tert–Butyloxycarbonyl and Benzyloxycarbonyl Amino Acid Fluorides. New, Stable Rapid–Acting Acylating Agents for Peptide Synthesis", J. Org. Chem., 56: 2611–2614, 1991.

Francis, et al., "Discovery of Novel Catalysts for Alkene Epoxidation from Metal–Binding Combinatorial Libraries", Angew. Chem. Int. Ed. 38: 937–941, 1999.

Green, et al., Mechanism of the Transformation of a Stiff Polymer Lyotropic Nematic Liquid.

(Continued)

Primary Examiner—Monique T. Cole
(74) Attorney, Agent, or Firm—Brenda Herschbach Jarrell; Nadege M. Lagneau; Choate, Hall & Stewart

(57) ABSTRACT

The present invention provides methods, compounds, and kits useful in the analysis of reaction products and components of reaction mixtures, and in certain embodiments for the rapid and simultaneous determination of enantiomeric ratios, percent conversions, and absolute configurations.

15 Claims, 27 Drawing Sheets

(9 of 27 Drawing Sheet(s) Filed in Color)

OTHER PUBLICATIONS

Crystal to the Cholesteric State by Dopant–Mediated Chiral Information Transfer, *J. Am .Chem. Soc.*, 120: 9810–9817, 1998.

Guo et al., "Measurement of Enantiomeric Excess by Kinetic Reaction and Mass Spectrometry" *Angew. Chem. Int. Ed. Engl*. 38: 1755–1758, 1999.

Horeau et al. "Nouvelle Methode Generale De Determination De La Purete Enantiomerique Et De La Configuration Absolute Des Alcools Secondaires Chiraux", *Tetrahedron Lett.*, 3259–3266, 1977.

Mehta, et al., "Improved Efficiency and Selectivity in Peptide Synthesis: Use of Triethylsilane as a Carbocation Scavenger in Deprotection of t–Butyl Esters and t–Butoxycarbonyl–Protected Sites", *Tet. Lett*, 33: 5441, 1992.

Ponnusamy, et al., "A Novel Method for the Rapid, Non–Aqueous *t*–Butoxycarbonylation of Some O–Labeled Amino Acids and O–N.M.R. Parameters of the Products" *Synthesis* , 48–49, 1986.

Reetz, M.T., "Combinatorial and Evolution–Based Methods in the Creation of Enantioselective Catalysts", *Angew. Chem. Int. Ed*. 40: 285–310, 2001.

Schreiber, et al., "Printing Small Molecules as Microarrays and Detecting Protein–Ligand Interactions en Masse" *J. Am. Chem. Soc.*, 121: 7967–7968, 1999.

Schreiber, et al., "Stereoselective Synthesis of Over Two Million Compounds Having Structural Features Both Reminiscent of Natural Products and Compatible with Miniaturized Cell–Based Assays", *J. Am. Chem. Soc.*, 120: 8565–8566, 1998.

Whitesell, et al., "Cyclohexyl–Based Chiral Auxiliaries", *Chem. Rev.*, 92: 953–964, 1992.

Reetz, et al., "A Method for High–Throughput Screening of Enantioselective Catalysts", Angew Chem. Int. Ed., 38(12): 1758–1761, 1999.

International Search Report issued for corresponding PCT application PCT/US01/04005.

* cited by examiner

Reagents and conditions: step 1) BocHNCH(R)CO$_2$H, PyAOP, $^i$Pr$_2$NEt, DMF,; step 2) Ac$_2$O, pyridine; step 3) 10% CF$_3$CO$_2$H and 10% Et$_3$SiH in CH$_2$Cl$_2$, then 3% Et$_3$N in CH$_2$Cl$_2$; step 4) Pentafluorophenyl diphenylphosphinate, $^i$Pr$_2$NEt, 1:1 mixture of 1 and 2, DMF, -20°C.

Attachment of amino acids as their allyl amides to nitrone-functionalized microslides Ala (s = 2.0)
| Calculated %e.e | 100 | 87.5 | 60.4 | 39.7 | 21.5 | 7.4 | 13.4 | 5.2 | 25.1 | 49.3 | 71.0 | 100 |
| Enantiomer | D | D | D | D | D | D | D | L | L | L | L | L |

Pro (s = 4.7)
| Calculated %e.e | 100 | 87.0 | 72.2 | 58.3 | 43.4 | 31.0 | 34.2 | 20.1 | 6.3 | 12.0 | 39.0 | 100 |
| Enantiomer | D | D | D | D | D | D | D | D | D | L | L | L |

Phe (s = 1.8)
| Calculated %e.e | 100 | 85.0 | 61.5 | 39.6 | 18.4 | 0.7 | 10.4 | 3.4 | 30.6 | 53.3 | 81.9 | 100 |
| Enantiomer | D | D | D | D | D | D | D | L | L | L | L | L | t-Leu (s = 1.4)

| | | | | | | | | | | | |
|---|---|---|---|---|---|---|---|---|---|---|---|
| Approximate %e.e | 100 | 80 | 60 | 40 | 20 | 0 | 0 | 20 | 40 | 60 | 80 | 100 |
| Calculated %e.e | 100 | 55.3 | 28.8 | N/A | 33.7 | 34.8 | 37.6 | 6.8 | 6.3 | 46.0 | 70.8 | 100 |
| Expected enantiomer | D | D | D | D | D | D | D | L | L | L | L | L |
| Enantiomer | D | D | D | N/A | D | D | D | D | L | L | L | L |

FIGURE 14

| Alanine | 100% ee | 90% ee | 80% ee | 70% ee | 60% ee | 50% ee | 40% ee | 30% ee | 20% ee | 10% ee | 0% ee |
|---|---|---|---|---|---|---|---|---|---|---|---|
| Valid cases | 9.0 | 8.0 | 8.0 | 8.0 | 9.0 | 9.0 | 9.0 | 9.0 | 8.0 | 8.0 | 9.0 |
| Mean | 100.0 | 91.4 | 80.2 | 67.5 | 62.6 | 54.9 | 38.8 | 31.9 | 21.5 | 11.6 | 0.0 |
| Std. error of mean | 0.0 | 1.2 | 2.4 | 4.3 | 3.7 | 4.9 | 3.4 | 3.5 | 1.8 | 1.5 | 0.0 |
| Variance | 0.0 | 11.7 | 47.3 | 145.1 | 126.1 | 217.2 | 105.1 | 108.3 | 26.6 | 18.0 | 0.0 |
| Std. Deviation | 0.0 | 3.4 | 6.9 | 12.0 | 11.2 | 14.7 | 10.3 | 10.4 | 5.2 | 4.2 | 0.0 |
| Minimum | 100.0 | 86.5 | 69.7 | 47.7 | 48.0 | 35.9 | 26.5 | 21.4 | 14.4 | 6.0 | 0.0 |
| Maximum | 100.0 | 95.7 | 91.2 | 85.7 | 79.7 | 79.5 | 58.9 | 53.3 | 27.8 | 17.6 | 0.0 |
| Range | 0.0 | 9.2 | 21.5 | 38.0 | 31.7 | 43.6 | 32.3 | 31.9 | 13.4 | 11.6 | 0.0 |
| Median | 100.0 | 92.0 | 79.1 | 65.9 | 60.4 | 58.4 | 40.2 | 27.2 | 20.7 | 11.2 | 0.0 |
| Geom. mean | 100.0 | 91.3 | 79.9 | 66.5 | 61.8 | 53.1 | 37.7 | 30.6 | 21.0 | 10.9 | --- |

| Alanine | -10% ee | -20% ee | -30% ee | -40% ee | -50% ee | -60% ee | -70% ee | -80% ee | -90% ee | -100% ee |
|---|---|---|---|---|---|---|---|---|---|---|
| Valid cases | 10.0 | 10.0 | 10.0 | 9.0 | 8.0 | 8.0 | 8.0 | 7.0 | 8.0 | 10.0 |
| Mean | 12.3 | 24.4 | 31.8 | 42.4 | 61.5 | 60.1 | 71.5 | 76.1 | 89.6 | 100.0 |
| Std. error of mean | 1.5 | 1.7 | 2.2 | 2.2 | 5.2 | 2.5 | 2.1 | 1.6 | 1.1 | 0.0 |
| Variance | 23.1 | 27.6 | 46.3 | 43.6 | 214.0 | 50.8 | 36.2 | 18.6 | 10.1 | 0.0 |
| Std. Deviation | 4.8 | 5.3 | 6.8 | 6.6 | 14.6 | 7.1 | 6.0 | 4.3 | 3.2 | 0.0 |
| Minimum | 5.1 | 14.4 | 19.7 | 29.8 | 44.5 | 47.1 | 64.4 | 67.1 | 85.8 | 100.0 |
| Maximum | 18.1 | 33.5 | 41.0 | 52.6 | 89.5 | 71.1 | 82.7 | 79.9 | 95.4 | 100.0 |
| Range | 13.0 | 19.1 | 21.3 | 22.8 | 45.0 | 24.0 | 18.3 | 12.8 | 9.6 | 0.0 |
| Median | 14.7 | 24.9 | 31.8 | 41.9 | 57.4 | 59.3 | 70.0 | 77.5 | 89.2 | 100.0 |
| Geom. mean | 11.2 | 23.9 | 31.1 | 41.9 | 60.1 | 59.7 | 71.2 | 76.0 | 89.6 | 100.0 |

FIGURE 16B

| Valine | 100% ee | 90% ee | 80% ee | 70% ee | 60% ee | 50% ee | 40% ee | 30% ee | 20 % ee | 10% ee | 0% ee |
|---|---|---|---|---|---|---|---|---|---|---|---|
| Valid cases | 7 | 7 | 6 | 7 | 7 | 7 | 7 | 7 | 7 | 7 | 10 |
| Mean | 100.0 | 88.8 | 78.6 | 70.7 | 58.4 | 52.1 | 38.9 | 31.1 | 19.6 | 11.9 | 0.0 |
| Std. error of mean | 0.0 | 2.0 | 3.2 | 3.5 | 3.3 | 3.7 | 3.4 | 3.0 | 2.8 | 1.3 | 0.0 |
| Variance | 0.0 | 28.3 | 60.8 | 84.4 | 74.4 | 94.2 | 79.1 | 64.5 | 55.4 | 12.0 | 0.0 |
| Std. Deviation | 0.0 | 5.3 | 7.8 | 9.2 | 8.6 | 9.7 | 8.9 | 8.0 | 7.4 | 3.5 | 0.0 |
| Minimum | 100.0 | 82.1 | 65.0 | 56.7 | 44.7 | 36.6 | 29.4 | 22.7 | 5.2 | 7.7 | 0.0 |
| Maximum | 100.0 | 98.0 | 84.9 | 82.6 | 68.5 | 66.1 | 52.6 | 41.2 | 28.5 | 16.7 | 0.0 |
| Range | 0.0 | 15.9 | 19.9 | 26.0 | 23.9 | 29.5 | 23.2 | 18.5 | 23.2 | 9.0 | 0.0 |
| Median | 100.0 | 88.0 | 80.9 | 72.7 | 58.5 | 51.2 | 35.8 | 26.3 | 19.4 | 11.4 | 0.0 |
| Geom. mean | 100.0 | 88.7 | 78.2 | 70.1 | 57.8 | 51.3 | 38.1 | 30.2 | 17.7 | 11.5 | --- |

| Valine | -10% ee | -20% ee | -30% ee | -40% ee | -50% ee | -60% ee | -70% ee | -80% ee | -90% ee | -100% ee |
|---|---|---|---|---|---|---|---|---|---|---|
| Valid cases | 10 | 10 | 10 | 10 | 10 | 2 | 5 | 10 | 10 | 10 |
| Mean | 13.3 | 25.2 | 34.5 | 42.4 | 53.2 | 98.8 | 75.7 | 76.8 | 92.6 | 100.0 |
| Std. error of mean | 1.3 | 1.2 | 1.6 | 3.0 | 2.3 | 21.7 | 3.0 | 1.3 | 2.8 | 0.0 |
| Variance | 16.0 | 15.5 | 24.5 | 88.2 | 55.0 | 941.8 | 46.3 | 16.1 | 77.4 | 0.0 |
| Std. Deviation | 4.0 | 3.9 | 4.9 | 9.4 | 7.4 | 30.7 | 6.8 | 4.0 | 8.8 | 0.0 |
| Minimum | 7.8 | 19.2 | 27.3 | 34.0 | 45.7 | 75.1 | 71.3 | 69.8 | 81.6 | 100.0 |
| Maximum | 18.7 | 31.8 | 42.0 | 65.8 | 68.7 | 118.5 | 87.5 | 81.7 | 114.3 | 100.0 |
| Range | 10.9 | 12.6 | 14.8 | 31.8 | 22.9 | 43.4 | 16.2 | 11.9 | 32.8 | 0.0 |
| Median | 14.9 | 25.2 | 33.7 | 40.7 | 52.5 | 96.8 | 72.7 | 76.7 | 91.4 | 100.0 |
| Geom. mean | 12.7 | 24.9 | 34.1 | 41.7 | 52.7 | 94.4 | 75.5 | 76.7 | 92.2 | 100.0 |

FIGURE 17B

| Leucine | 100% ee | 90% ee | 80% ee | 70% ee | 60% ee | 50% ee | 40% ee | 30% ee | 20 % ee | 10% ee | 0% ee |
|---|---|---|---|---|---|---|---|---|---|---|---|
| Valid cases | 12 | 6 | 8 | 6 | 8 | 9 | 9 | 9 | 8 | 9 | 12 |
| Mean | 100.0 | 89.7 | 79.1 | 69.1 | 59.1 | 49.1 | 35.7 | 29.1 | 19.8 | 12.3 | 0.0 |
| Std. error of mean | 0.0 | 2.4 | 2.1 | 2.2 | 2.6 | 2.1 | 2.6 | 2.5 | 1.7 | 2.1 | 0.0 |
| Variance | 0.0 | 35.4 | 36.4 | 29.3 | 53.2 | 40.5 | 62.5 | 57.2 | 22.8 | 39.2 | 0.0 |
| Std. Deviation | 0.0 | 5.9 | 6.0 | 5.4 | 7.3 | 6.4 | 7.9 | 7.6 | 4.8 | 6.3 | 0.0 |
| Minimum | 100.0 | 81.1 | 69.3 | 62.5 | 46.7 | 39.5 | 23.1 | 20.1 | 13.2 | -2.1 | 0.0 |
| Maximum | 100.0 | 95.5 | 87.1 | 76.1 | 68.1 | 58.5 | 47.3 | 44.2 | 28.3 | 17.4 | 0.0 |
| Range | 0.0 | 14.3 | 17.8 | 13.6 | 21.4 | 19.0 | 24.1 | 24.1 | 15.1 | 19.5 | 0.0 |
| Median | 100.0 | 91.6 | 78.8 | 69.6 | 61.9 | 51.6 | 37.3 | 28.4 | 20.1 | 14.9 | 0.0 |
| Geom. mean | 100.0 | 89.5 | 78.9 | 68.9 | 58.7 | 48.7 | 34.8 | 28.2 | 19.3 | --- | --- |

| Leucine | -10% ee | -20% ee | -30% ee | -40% ee | -50% ee | -60% ee | -70% ee | -80% ee | -90% ee | -100% ee |
|---|---|---|---|---|---|---|---|---|---|---|
| Valid cases | 11 | 10 | 9 | 10 | 11 | 11 | 11 | 11 | 9 | 12 |
| Mean | 14.8 | 29.8 | 34.8 | 47.0 | 54.3 | 62.6 | 73.2 | 78.5 | 89.7 | 100.0 |
| Std. error of mean | 1.8 | 1.3 | 2.2 | 1.9 | 1.7 | 2.9 | 1.7 | 1.1 | 1.2 | 0.0 |
| Variance | 34.1 | 15.6 | 42.3 | 37.8 | 33.4 | 93.8 | 31.3 | 13.7 | 12.6 | 0.0 |
| Std. Deviation | 5.8 | 4.0 | 6.5 | 6.2 | 5.8 | 9.7 | 5.6 | 3.7 | 3.6 | 0.0 |
| Minimum | 9.0 | 22.1 | 27.5 | 35.1 | 46.2 | 51.7 | 65.6 | 73.7 | 84.1 | 100.0 |
| Maximum | 28.3 | 38.2 | 47.4 | 57.3 | 64.5 | 86.1 | 86.1 | 86.6 | 97.1 | 100.0 |
| Range | 19.3 | 16.1 | 19.9 | 22.2 | 18.3 | 34.4 | 20.5 | 12.9 | 12.9 | 0.0 |
| Median | 13.4 | 29.6 | 35.4 | 47.4 | 55.3 | 60.3 | 72.4 | 79.3 | 89.2 | 100.0 |
| Geom. mean | 14.0 | 29.6 | 34.3 | 46.7 | 54.0 | 62.0 | 73.0 | 78.4 | 89.6 | 100.0 |

FIGURE 18B

| Prolin | 100% ee | 90% ee | 80% ee | 70% ee | 60% ee | 50% ee | 40% ee | 30% ee | 20 % ee | 10% ee | 0% ee |
|---|---|---|---|---|---|---|---|---|---|---|---|
| Valid cases | 5 | 4 | 5 | 5 | 5 | 4 | 4 | 5 | 5 | 5 | 3 |
| Mean | 100.0 | 89.4 | 82.2 | 73.3 | 65.2 | 60.8 | 45.3 | 34.9 | 25.2 | 13.6 | 0.0 |
| Std. error of mean | 0.0 | 3.1 | 2.2 | 1.1 | 2.3 | 2.5 | 2.8 | 2.4 | 2.0 | 1.4 | 0.0 |
| Variance | 0.0 | 38.0 | 23.8 | 6.3 | 26.3 | 24.6 | 31.4 | 27.7 | 20.4 | 9.9 | 0.0 |
| Std. Deviation | 0.0 | 6.2 | 4.9 | 2.5 | 5.1 | 5.0 | 5.6 | 5.3 | 4.5 | 3.2 | 0.0 |
| Minimum | 100.0 | 85.2 | 75.0 | 71.2 | 59.1 | 56.7 | 39.6 | 27.4 | 20.0 | 9.7 | 0.0 |
| Maximum | 100.0 | 98.3 | 88.2 | 77.4 | 73.2 | 66.6 | 52.1 | 40.6 | 30.1 | 18.1 | 0.0 |
| Range | 0.0 | 13.1 | 13.2 | 6.2 | 14.2 | 9.9 | 12.5 | 13.2 | 10.1 | 8.4 | 0.0 |
| Median | 100.0 | 87.1 | 82.5 | 72.9 | 64.9 | 60.0 | 44.8 | 34.4 | 23.1 | 12.7 | 0.0 |
| Geom. mean | 100.0 | 89.3 | 82.1 | 73.3 | 65.0 | 60.7 | 45.1 | 34.8 | 24.9 | 13.3 | --- |

| Prolin | -10% ee | -20% ee | -30% ee | -40% ee | -50% ee | -60% ee | -70% ee | -80% ee | -90% ee | -100% ee |
|---|---|---|---|---|---|---|---|---|---|---|
| Valid cases | 9 | 10 | 9 | 10 | 9 | 10 | 10 | 10 | 8 | 10 |
| Mean | 6.4 | 21.1 | 31.2 | 42.1 | 42.8 | 67.5 | 74.6 | 84.6 | 93.3 | 100.0 |
| Std. error of mean | 1.1 | 0.8 | 1.0 | 2.0 | 3.0 | 2.0 | 1.5 | 2.3 | 1.3 | 0.0 |
| Variance | 11.4 | 8.5 | 8.9 | 38.5 | 81.4 | 40.7 | 23.0 | 52.2 | 12.6 | 0.0 |
| Std. Deviation | 3.4 | 2.9 | 3.0 | 6.2 | 9.0 | 6.4 | 4.8 | 7.2 | 3.5 | 0.0 |
| Minimum | -1.7 | 16.2 | 26.3 | 32.6 | 22.0 | 57.6 | 64.2 | 68.8 | 88.9 | 100.0 |
| Maximum | 9.5 | 24.9 | 35.0 | 55.5 | 53.3 | 79.5 | 80.2 | 97.0 | 98.9 | 100.0 |
| Range | 11.2 | 8.8 | 8.7 | 22.9 | 31.4 | 21.9 | 16.0 | 28.3 | 10.1 | 0.0 |
| Median | 8.4 | 21.6 | 32.6 | 43.3 | 43.1 | 65.6 | 76.5 | 85.6 | 92.2 | 100.0 |
| Geom. mean | --- | 20.9 | 31.1 | 41.7 | 41.6 | 67.3 | 74.5 | 84.3 | 93.3 | 100.0 |

FIGURE 19B

| Serine | 100% ee | 90% ee | 80% ee | 70% ee | 60% ee | 50% ee | 40% ee | 30% ee | 20% ee | 10% ee | 0% ee |
|---|---|---|---|---|---|---|---|---|---|---|---|
| Valid cases | 6 | 6 | 6 | 6 | 5 | 6 | 5 | 6 | 6 | 6 | 8 |
| Mean | 100.0 | 91.1 | 77.1 | 65.0 | 54.7 | 48.9 | 40.0 | 36.8 | 27.0 | 13.4 | 0.0 |
| Std. error of mean | 0.0 | 2.2 | 2.8 | 3.3 | 2.6 | 1.7 | 2.6 | 2.2 | 3.5 | 3.5 | 0.0 |
| Variance | 0.0 | 28.5 | 47.8 | 63.5 | 34.7 | 17.2 | 35.0 | 29.8 | 73.0 | 72.4 | 0.0 |
| Std. Deviation | 0.0 | 5.3 | 6.9 | 8.0 | 5.9 | 4.1 | 5.9 | 5.5 | 8.5 | 8.5 | 0.0 |
| Minimum | 100.0 | 86.5 | 66.0 | 53.7 | 46.2 | 42.9 | 34.2 | 27.5 | 15.2 | 0.4 | 0.0 |
| Maximum | 100.0 | 98.4 | 85.6 | 77.0 | 62.6 | 54.7 | 46.7 | 44.2 | 39.5 | 26.6 | 0.0 |
| Range | 0.0 | 11.9 | 19.6 | 23.3 | 16.3 | 11.7 | 12.8 | 16.8 | 24.4 | 26.2 | 0.0 |
| Median | 100.0 | 88.7 | 77.9 | 65.0 | 54.5 | 49.4 | 37.6 | 37.7 | 26.7 | 13.2 | 0.0 |
| Geom. mean | 100.0 | 91.0 | 76.8 | 64.6 | 54.4 | 48.8 | 39.7 | 36.4 | 25.8 | 8.1 | --- |

| Serine | -10% ee | -20% ee | -30% ee | -40% ee | -50% ee | -60% ee | -70% ee | -80% ee | -90% ee | -100% ee |
|---|---|---|---|---|---|---|---|---|---|---|
| Valid cases | 7 | 8 | 8 | 8 | 8 | 8 | 7 | 7 | 7 | 8 |
| Mean | 10.9 | 34.0 | 33.8 | 45.4 | 60.9 | 63.0 | 75.2 | 83.6 | 88.0 | 100.0 |
| Std. error of mean | 4.1 | 2.6 | 2.5 | 3.9 | 3.5 | 2.7 | 4.5 | 3.3 | 4.6 | 0.0 |
| Variance | 116.7 | 52.4 | 49.8 | 122.1 | 99.4 | 57.3 | 144.2 | 74.4 | 147.5 | 0.0 |
| Std. Deviation | 10.8 | 7.2 | 7.1 | 11.1 | 10.0 | 7.6 | 12.0 | 8.6 | 12.1 | 0.0 |
| Minimum | -2.6 | 18.0 | 21.3 | 30.9 | 46.4 | 48.8 | 54.3 | 70.4 | 65.9 | 100.0 |
| Maximum | 26.4 | 41.7 | 43.2 | 60.2 | 76.4 | 70.4 | 91.8 | 96.3 | 101.8 | 100.0 |
| Range | 29.0 | 23.7 | 21.8 | 29.3 | 30.0 | 21.6 | 37.5 | 25.9 | 35.9 | 0.0 |
| Median | 11.2 | 36.8 | 34.8 | 47.1 | 62.3 | 66.4 | 76.2 | 83.9 | 87.8 | 100.0 |
| Geom. mean | --- | 33.1 | 33.1 | 44.1 | 60.2 | 62.6 | 74.3 | 83.2 | 87.2 | 100.0 |

| Cys | 100% ee | 90% ee | 80% ee | 70% ee | 60% ee | 50% ee | 40% ee | 30% ee | 20 % ee | 10% ee | 0% ee |
|---|---|---|---|---|---|---|---|---|---|---|---|
| Valid cases | 8 | 8 | 8 | 8 | 8 | 8 | 8 | 8 | 8 | 8 | 6 |
| Mean | 100.0 | 84.0 | 78.7 | 79.1 | 72.9 | 67.7 | 45.8 | 49.2 | 41.2 | -1.5 | 0.0 |
| Std. error of mean | 0.0 | 2.8 | 6.6 | 5.0 | 4.1 | 4.6 | 3.5 | 6.2 | 4.1 | 5.1 | 0.0 |
| Variance | 0.0 | 63.8 | 351.6 | 196.9 | 100.7 | 172.0 | 73.6 | 307.7 | 134.1 | 209.5 | 0.0 |
| Std. Deviation | 0.0 | 8.0 | 18.8 | 14.0 | 10.0 | 13.1 | 8.6 | 17.5 | 11.6 | 14.5 | 0.0 |
| Minimum | 100.0 | 72.0 | 37.4 | 60.0 | 58.3 | 47.8 | 32.8 | 36.0 | 27.2 | -33.3 | 0.0 |
| Maximum | 100.0 | 95.4 | 97.7 | 101.5 | 89.3 | 82.2 | 55.4 | 89.4 | 56.1 | 12.0 | 0.0 |
| Range | 0.0 | 23.4 | 60.3 | 41.5 | 31.0 | 34.4 | 22.6 | 53.5 | 28.9 | 45.3 | 0.0 |
| Geom. mean | 100.0 | 83.7 | 76.0 | 78.0 | 72.3 | 66.5 | 45.0 | 47.1 | 39.8 | --- | --- |

| Cys | -10% ee | -20% ee | -30% ee | -40% ee | -50% ee | -60% ee | -70% ee | -80% ee | -90% ee | -100% ee |
|---|---|---|---|---|---|---|---|---|---|---|
| Valid cases | 6 | 7 | 7 | 6 | 6 | 7 | 6 | 6 | 6 | 7 |
| Mean | -1.0 | 40.0 | 32.3 | 45.7 | 53.7 | 64.6 | 68.4 | 77.1 | 83.1 | 100.0 |
| Std. error of mean | 2.4 | 3.3 | 3.6 | 3.3 | 3.5 | 7.3 | 3.9 | 5.3 | 4.6 | 0.0 |
| Variance | 34.7 | 76.6 | 88.4 | 67.3 | 73.4 | 373.1 | 105.3 | 171.7 | 125.8 | 0.0 |
| Std. Deviation | 5.9 | 8.8 | 9.4 | 8.2 | 8.6 | 19.3 | 10.3 | 13.1 | 11.2 | 0.0 |
| Minimum | -8.4 | 25.0 | 19.3 | 34.1 | 39.3 | 44.7 | 49.7 | 55.0 | 63.0 | 100.0 |
| Maximum | 6.6 | 51.1 | 44.5 | 55.5 | 64.8 | 102.6 | 79.3 | 92.7 | 92.5 | 100.0 |
| Range | 15.0 | 26.0 | 25.2 | 21.5 | 25.6 | 58.0 | 29.6 | 37.7 | 29.5 | 0.0 |
| Geom. mean | --- | 39.1 | 31.1 | 45.1 | 53.1 | 62.5 | 67.6 | 76.1 | 82.4 | 100.0 |

FIGURE 21B

METHOD FOR ANALYSIS OF REACTION PRODUCTS

PRIORITY INFORMATION

This application claims priority under 35 U.S.C. §119(e) to provisional patent application 60/180,664 filed Feb. 7, 2000, entitled "Method for Analysis of Reaction Products", the entire contents of which are hereby incorporated by reference.

BACKGROUND OF THE INVENTION

As a result of the importance of asymmetric synthesis in synthetic organic, medicinal, agricultural, and natural products chemistry, and their related industries, the discovery of chiral ligand-metal complexes that are capable of catalyzing reactions with high enantioselectivity, and generating optically pure or enantiomerically enriched products has been an area of intense research (see, for example, R. Noyori, "Asymmetric Catalysis in Organic Synthesis", Wiley, N.Y. 1994). Unfortunately, catalyst discovery and optimization has traditionally been conducted using the laborious and time consuming one-at-a-time technique, which involves the synthesis of "potential" catalysts one-at-a time and subsequently testing those "potential" catalysts one-at-a-time for activity.

In recent years, there has been a significant increase in the use of combinatorial chemistry techniques for the discovery of new catalysts (see, for example, Jandeleit et al. "Combinatorial Materials Science" *Angew. Chem. Int. Ed. Engl.* 1999, 38, 2494; Crabtree, R. H. "Speeding Catalyst Discovery and Optimization" *Chemtech*, April 1999, 21–26). One recent example of the use of combinatorial techniques for catalyst discovery and optimization is the discovery of a novel catalyst for alkene epoxidation (Francis, M. B., Jacobsen, E. N. *Angew. Chem. Int. Ed.* 1999, 38, 937) in which 192 different ligands were tested and visually selected for their metal-binding ability in a pooled assay with 30 different metal ion sources, and then screened for the ability to catalyze the epoxidation of trans-β-methylstyrene using gas chromatography. Other developments in catalyst discovery using combinatorial methods include the discovery of catalysts for metallocarbene C—H insertions (Burgess et al. *Angew. Chem. Int. Ed. Engl.* 1996, 35, 220), homochiral Lewis Acid catalysts for asymmetric aza-Diels-Alder reactions (Bromidge et al. *Tetrahedron Lett.* 1998, 39, 8905), and palladium-catalyzed allylic alkylations (Porte et al. *J. Am. Chem. Soc.* 1998, 120, 9810; Burgess et al. *Tetrahedron. Asymmetry* 1998, 9, 2465), to name a few. For a more comprehensive discussion of the use of combinatorial techniques in asymmetric catalysis, see Jandeleit et al., and references cited therein.

Although there has been a significant improvement in the discovery of new catalysts using combinatorial catalysis techniques, many of the techniques relied upon to assay these potential catalysts are still laborious and time consuming. For example, most of the assays rely on the use of traditional gas chromatography or mass spectrometry methods to analyze reaction products and typically can only analyze one sample every few minutes, and additionally require additional time between samples. One example of the progress towards the development of high-throughput screening techniques includes the use of mass tagged chiral acylating agents to diastereoselectively derivatize and automate qualtitive electrospray ionization mass spectrometry (ESI-MS) (Guo et al. *Angew. Chem. Int. Ed. Engl.* 1999, 38, 1755). This method, however, is still laborious and time consuming, particularly for the screening of as many as, or more than, 10,000 products, because each sample must be injected into the mass spectrometer (only samples with differing molecular weights may be combined) and requires approximately two minutes to complete. Therefore, the analysis of 10,000 reaction products, at two minutes per sample, including a 20 minute wash after every 36 samples, would require approximately 17.65 days (working 24 hours a day) to complete.

Clearly, there remains a need to develop truly high-throughput methods for the analysis of reaction products and/or mixtures, particularly for the determination of enantiomeric ratios, relative conversion and absolute configuration for large numbers (e.g., tens-of-thousands, or more) of reaction mixtures. A significant acceleration in the discovery and optimization of enantioselective catalysts, stoichiometric reagents, reactions, and reaction conditions would result if tens-of-thousands (or millions) of experiments, such as catalysis experiments, were able to be performed simultaneously in a relatively short amount of time, preferably within one working day, followed by high-throughput determination or identification of product characteristics including, but not limited to, functional group identity, percent yields, product enantiomeric ratios, relative conversions and absolute configurations.

SUMMARY OF THE INVENTION

In recognition of the need to develop more rapid methods for the identification and optimization of catalysts, reactions, or reaction conditions in asymmetric synthesis, the present invention provides methods, compounds, and kits useful in the analysis of reaction products. In certain embodiments, the present invention provides methods and kits for the rapid and simultaneous determination of enantiomeric ratios, percent conversions, and absolute configurations. In certain other embodiments, the present invention additionally provides methods and kits for the rapid and simultaneous determination of the identity of reaction products including, but not limited to product functionality, percent yield, enantiomeric ratios, percent conversions, and absolute configurations, to name a few.

In certain embodiments, the invention provides a method for high-throughput screening of reaction products comprising determining any one or all of enantiomeric ratios, absolute configuration and percent conversion for the products of at least 10,000 reactions in 48 hours or less. In certain other embodiments, any one or all of enantiomeric ratios, absolute configuration and percent conversion for the products of at least 10,000 reactions is determined in 24 hours or less. In still other embodiments, any one or all of enantiomeric ratios, absolute configuration and percent conversion for the products of at least 10,000 reactions is determined in 1 hour or less.

The present invention provides a method of analyzing the components of one or more reaction mixtures comprising 1) arraying the components of one or more reaction mixtures on a surface; 2) contacting the components of one or more reaction mixtures with one or more sets of identification reagents, whereby the identification reagent comprises a detection reagent and an identification moiety; and 3) analyzing said one or more reaction mixtures, whereby interaction of the identification reagents with the components of the reaction mixtures enables determination of the identity of the reaction components, and whereby each identification reagent is capable of being uniquely identified. In certain embodiments, the step of arraying comprises printing at least 10,000 reaction mixtures. In certain other embodiments, the steps of contacting and analyzing comprise contacting the components of one or more reaction mixtures with a first set of identification reagents and analyzing the components, whereby interaction of said identification reagents with the reaction components enables determination of any one or all of enantiomeric ratios, absolute configuration or percent conversion; and contacting the components of one or more reaction mixtures with a second set of identification reagents and analyzing the components, whereby interaction of said identification reagents with the reaction components enables determination of functional group identities of one or more or the reaction components. In still other embodiments, the identification reagent is a chiral detecting reagent.

In yet other embodiments, the method further comprises a step of determining percent yield based upon the determination of the functional group identities of one or more reaction components.

In other embodiments, a method for analyzing reaction products for one or more reactions is provided comprising 1) arraying one or more samples of one or more reaction products on a surface; 2) contacting said one or more samples of reaction products from said one or more reactions with one or more sets of chiral detecting reagents, wherein each chiral detecting reagent comprises a detecting reagent and a chiral reagent; and 3) analyzing said one or more samples of reaction products, whereby interaction of said chiral detecting agents with the reaction products enables determination of any one or all of enantiomeric ratios, absolute configuration and percent conversion. In certain embodiments, the step of arraying comprises printing at least 10,000 reaction products. In certain other embodiments, the step of analyzing is conducted using a scanning technique. In yet other embodiments, the step of analyzing comprises analyzing 10,000 or more samples in 48 hours or less. In still other embodiments, the step of arraying comprises printing one or more samples of enantiomeric reaction products.

In certain embodiments, for each of the methods as described above and as disclosed herein at least one set of chiral detecting reagents comprises a pair of reagents, each having the following structural formula (I):

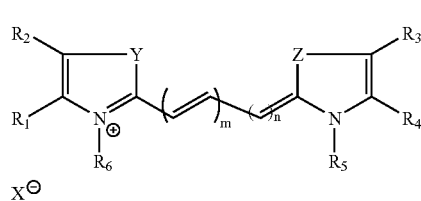

wherein $R_1$ and $R_2$, and $R_3$ and $R_4$ taken together each independently comprise a substituted or unsubstituted cyclic or polycyclic aryl or heteroaromatic moiety; wherein m is 1, 2, or 3; wherein n is 0 or 1; wherein Z or Y each independently comprise —C(R)$_2$—, wherein each occurrence of the functional moiety R, is independently selected from the group consisting of hydrogen and methyl; NR, wherein R is selected from the group consisting of hydrogen and methyl; O; S; or Se; wherein X is a non-coordinating negative counter ion including, but not limited to $BF_4$, $PF_6$, $ClO_4$, TsO, I, Br; and wherein $R_5$ or $R_6$ each independently comprise lower alkyl, a chiral reagent (CR) or a chiral reagent and linker (L-CR), whereby said chiral reagent is attached to the detecting agent via the linker, with the proviso that at least one of $R_5$ or $R_6$ is a chiral reagent (CR) or a chiral reagent and linker (L-CR); and wherein the chiral reagent (CR) for the first chiral detecting reagent (CDR) and for the second chiral detecting reagent (CDR) in a pair are enantiomers, and wherein each of said chiral detecting reagents in a set is capable of selectively reacting with one enantiomeric reaction product over the other enantiomeric reaction product in a sample of reaction products and is capable of being uniquely identified.

In certain embodiments, for each of said chiral detecting reagents, $R_1$ and $R_2$ and $R_3$ and $R_4$ taken together each comprise, a benzene moiety, $C_6H_6$; wherein each of Z and Y are —C(CH$_3$)$_2$ wherein the linker moiety, L, comprises —(CH)$_p$—(CO)—; wherein p is 1–5, and in certain embodiments is 4, and wherein the chiral reagent (CR) comprises a chiral acylating agent having the general structure: —(NH)—(CHR$_x$)—COOH, where R$_x$ comprises a chiral amino acid residue.

In another aspect of the present invention a chiral detecting reagent is provided comprising the structure (I):

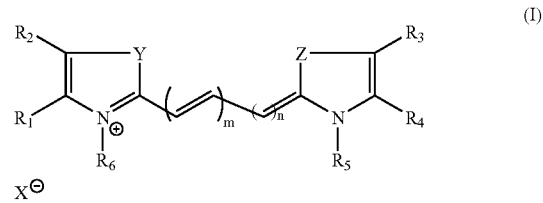

wherein $R_1$ and $R_2$, and $R_3$ and $R_4$ taken together each independently comprise a substituted or unsubstituted cyclic or polycyclic aryl or heteroaromatic moiety; wherein m is 1, 2, or 3; wherein n is 0 or 1; wherein Z or Y each independently comprise —C(R)$_2$—, wherein each occurrence of the functional moiety R, is independently selected from the group consisting of hydrogen and methyl; NR, wherein R is selected from the group consisting of hydrogen and methyl; O; S; or Se; wherein X is a non-coordinating negative counter ion including, but not limited to $BF_4$, $PF_6$, $ClO_4$, TsO, I, Br; and wherein $R_5$ or $R_6$ each independently comprise lower alkyl, a chiral reagent (CR) or a chiral reagent and linker (L-CR), whereby said chiral reagent is attached to the detecting agent via the linker, with the proviso that at least one of $R_5$ or $R_6$ is a chiral reagent (CR) or a chiral reagent and linker (L-CR).

In certain embodiments, $R_1$ and $R_2$ and $R_3$ and R4 taken together each comprise a benzene moiety, $C_6H_6$; wherein each of Z and Y are —C(CH$_3$)$_2$ ; wherein the linker moiety comprises —CH)$_p$—(CO)—; wherein p is 1–5, and in certain embodiments is 4, and wherein the chiral reagent comprises a chiral acylating agent having the general structure: —(NH)—(CHR$_x$)—COOH, where R$_x$ comprises a chiral amino acid residue.

In still another aspect the present invention provides a kit comprising one or more sets of chiral detecting reagents, wherein each set of chiral detecting reagents includes a pair of reagents for reaction with one or more functional groups present in products to be analyzed, wherein each chiral detecting reagent in the pair is capable of selectively reacting with one enantiomeric product over another in a reaction mixture, and whereby each chiral detecting reagent is capable of being uniquely identified.

In certain embodiments, at least one set of chiral detecting reagents in kits described above and as disclosed herein comprises the structural formula:

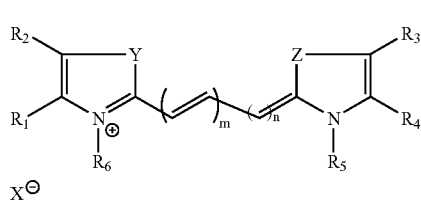

(I)

wherein $R_1$ and $R_2$, and $R_3$ and $R_4$ taken together each independently comprise a substituted or unsubstituted cyclic or polycyclic aryl or heteroaromatic moiety; wherein m is 1, 2, or 3; wherein n is 0 or 1; wherein Z or Y each independently comprise —$C(R)_2$—, wherein each occurrence of the finctional moiety R, is independently selected from the group consisting of hydrogen and methyl; NR, wherein R is selected from the group consisting of hydrogen and methyl; O; S; or Se; wherein X is a non-coordinating negative counter ion including, but not limited to $BF_4$, $PF_6$, $ClO_4$, TsO, I, Br; and wherein $R_5$ or $R_6$ each independently comprise lower alkyl, a chiral reagent (CR) or a chiral reagent and linker (L-CR), whereby said chiral reagent is attached to the detecting agent via the linker, with the proviso that at least one of $R_5$ or $R_6$ is a chiral reagent (CR) or a chiral reagent and linker (L-CR); and wherein the chiral reagent (CR) for the first chiral detecting reagent (CDR) and for the second chiral detecting reagent (CDR) in a pair are enantiomers, and wherein each of said chiral detecting reagents is capable of selectively reacting with one enantiomeric reaction product over the other enantiomeric reaction product in a pair and is capable of being uniquely identified.

In still other embodiments for the kits as described above and as disclosed herein, $R_1$ and $R_2$ and $R_3$ and $R_4$ taken together each comprise a benzene moiety, $C_6H_6$; wherein each of Z and Y are —$C(CH_3)_2$ wherein the linker moiety comprises —$(CH)_p$—(CO)—; wherein p is 1–5, and in certain embodiments is 4, and wherein the chiral agent comprises a chiral acylating agent having the general structure: —(NH)—($CHR_x$)—COOH, where $R_x$ comprises a chiral amino acid residue.

In yet other embodiments, kits as described above and as disclosed herein further comprises at least one set of identification reagents, wherein said identification reagents comprise a detection reagent and an identification moiety, whereby the identification moiety is capable of reacting with specific functional groups in a reaction mixture, and enables determination of functional group identity and percent yield.

DESCRIPTION OF THE DRAWING

The file of this patent contains at least one drawing executed in color. Copies of this patent with color drawings will be provided by the Patent and Trademark Office upon request and payment of the necessary fee.

FIG. 14 depicts the spot colors and mean ee % resulting from the printing of amino acids on glass slides as mixtures of enantiomers ranging from 100% ee D- to 100% ee L- in steps of 10% ee and subsequently treating the amino acids with pseudoenantiomeric probes 1 and 2 (shown in FIG. 4).

DEFINITIONS

Figure 1:
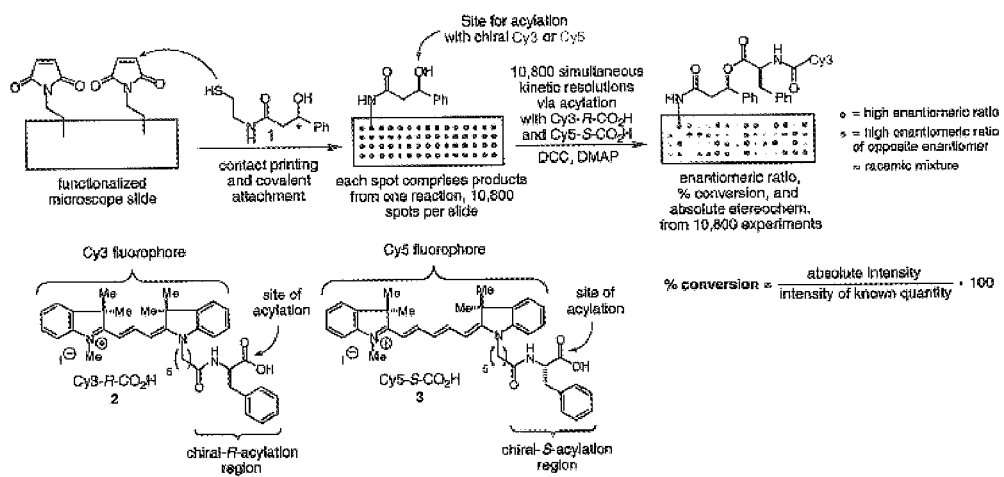
FIG. 1 depicts one embodiment of the present invention in which the reaction products are printed to generate Reaction Microarrays for subsequent analysis using Cy3 and Cy5 based chiral detecting agents.

As discussed above, the present invention provides a novel method for the analysis of reaction products to obtain information about the identity of components (for example reactants and products) of a reaction mixture, including, but not limited to functional group identity, percent yield, enantiomeric ratios, absolute configurations and yields, as will be described in more detail below. Additionally, the present invention provides kits and novel compounds useful in the method of the present invention. In particular, the compounds of the present invention, and definitions of specific functional groups are described in more detail below. For purposes of this invention, the chemical elements are identified in accordance with the Periodic Table of the Elements, CAS version, Handbook of Chemistry and Physics, $72^{nd}$ Ed., inside cover, and specific functional groups are defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. This invention is not intended to be limited in any manner by the permissible substituents of organic compounds. Combinations of substituents and variables envisioned by this invention are preferably those that result in the formation of stable compounds useful as chiral detecting agents in the present invention. The term "stable", as used herein, preferably refers to compounds which possess stability sufficient to allow manufacture and which maintain the integrity of the compound for a sufficient period of time to be useful for the purposes detailed herein (e.g., as a chiral detecting agent).

"Chiral": The term "chiral", as used herein, refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

"Stereoisomers": The term "stereoisomers" refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

"Enantiospecific reaction": The term, "enantiospecific reaction", as used herein, refers to a reaction process in which only one enantiomer is produced.

"Enantioselective reaction": The term "enantioselective reaction", as used herein, refers to a reaction in which one enantiomer is produced in preference to the other enantiomer. One way to express the degree of enantioselectivity of a particular reaction is as the "enantiomeric excess", which, as used herein, refers to the proportion of the major enantiomer produced in a reaction minus that of the minor enantiomer produced, expressed as a percentage, and as defined by the following equation:

$$e.e.(\%) = [\text{mole fraction (major enantiomer)} - \text{mole fraction (minor enantiomer)}] \times 100$$

Yet another way to express the degree of enantioselectivity of a particular reaction is by using "enantiomeric ratios", which simply is the amount of one enantiomer produced over the amount of the other enantiomer produced. One of ordinary skill in the art will realize that this ratio may be described with reference to either the major or minor enantiomer (i.e., as 1:2 or as 2:1).

"Racemic mixture": The term "racemic mixture", as used herein, refers to a mixture having equal amounts of two enantiomers.

"Scalemic mixture": The term "scalemic mixture", as used herein, refers to a mixture having unequal amounts of two enantiomers.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, alkyl, alkenyl, alkynyl, haloalkyl, alkoxy, thioalkoxy, amino, alkylamino, dialkylamino, acylamino, cyano, hydroxy, halo, mercapto, nitro, carboxaldehyde, carboxy, alkoxycarbonyl, imine, phosphoryl, sulfonyl, silyl groups, and carboxamide to name a few. It will be understood by those skilled in the art that the moieties substituted on the hydrocarbon chain can themselves be substituted, if appropriate. For instance, the substituents of a substituted alkyl may include substituted and unsubstituted forms of the above described functional moieties, as well as other appropriate and stable functional moieties not listed. Cycloalkyls can be further substituted with alkyls, alkenyls, alkoxys, thioalkyls, aminoalkyls, carbonyl-substituted alkyls, —$CF_3$, —CN, and the like.

The terms "alkenyl" and "alkynyl" refer to unsaturated aliphatic groups analogous in length and possible substitution to the alkyls described above, but which contain at least one double or triple bond respectively.

As used herein, the term "amino" means —$NH_2$; the term "nitro" means —$NO_2$; the term "halogen" designates —F, —Cl, —Br or —I; the term "thiol" means —SH; the term "hydroxyl" means —OH; and the term "sulfonyl" means —$SO_2$.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters and —CN.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —CN, or the like.

The term "heteroatom" as used herein means an atom of any element other than carbon or hydrogen. Preferred heteroatoms are nitrogen, oxygen, sulfur, phosphorus and selenium.

DETAILED DESCRIPTION OF THE INVENTION

The importance of asymmetric synthesis in the chemical and pharmaceutical industry is evidenced by the ever-increasing research efforts to discover catalysts capable of effecting enantioselective, and even more desirably enantiospecific, transformations (see, for example, Jandeleit et al. "Combinatorial Materials Science" *Angew. Chem. Int. Ed.* 1999, 38, 2494). As mentioned above, despite the increased interest and progress made in new screening methods, one of the biggest obstacles to the discovery of new catalysts, reactions, or reaction conditions is the inability to screen large numbers of products rapidly (for a recent review see Reetz, M. T. *Angew. Chem. Int. Ed.* 2001, 40, 284–310).

In recognition of the need to develop more rapid methods for the identification and optimization of catalysts, reactions, or reaction conditions in asymmetric synthesis, the present invention provides methods, compounds, and kits useful in the analysis of reaction products. In general, the method of the present invention can be utilized to determine the identity of one or more components of a reaction mixture (e.g., starting materials or reaction products). It will be appreciated that the term "identity of one or more components of a reaction mixture" refers to a number of characteristics of reactants (e.g., starting materials or products) including, but not limited to functional group identity (e.g., alcohol, ketone, amine, etc.) and chirality. In certain embodiments, where the chirality of reaction products is of interest, the method provides for the rapid and simultaneous determination of enantiomeric ratios, percent conversions, and absolute configurations. In certain other embodiments, the functional group identity of the starting materials and/or reaction products is of interest and the method provides for the rapid and simultaneous determination of functional group identity useful in the determination of percent yield.

In general, the method of the present invention involves 1) contacting the components of one or more reaction mixtures with one or more sets of identification reagents, whereby the identification reagent comprises a detection reagent and an identification moiety; and 2) analyzing said one or more reaction mixtures, whereby interaction of the identification reagents with the components of the reaction mixtures enables determination of the identity of the reaction components, and whereby each identification reagent is capable of being uniquely identified.

In certain embodiments, the identification reagents are chiral detecting reagents, and the method of the present invention involves contacting a sample of enantiomeric reaction products with one or more sets of chiral detecting reagents, and analyzing the sample of reaction products, whereby the interaction of the chiral detecting reagents with the reaction products enables rapid analysis and simultaneous determination of enantiomeric ratios, relative (percent) conversions, and absolute configurations. In particular, the method of the present invention takes advantage of the principles of kinetic resolution, in which a preferential reaction occurs (at a faster rate) between one chiral reagent and one enantiomeric product to form a diastereomeric product as a result of the lower transition state energy for that reaction.

Expanding on this general principle, the present invention utilizes identification reagents comprising an identification moiety and a detecting agent, whereby interaction of the identification reagents with a reaction mixture enables the determination of the identity of one or more components of a reaction mixture. In certain embodiments the identification reagents are chiral detection reagents (comprising a chiral agent and a detecting agent), whereby each agent in a set reacts at a different rate with each enantiomer in a reaction mixture, and thus reaction between one chiral detecting agent (A) and one enantiomeric product (A1) occurs to form a diastereomeric product, while a reaction between a second chiral detecting agent (B) and a second enantiomeric product (B1) occurs to form a diastereomeric product. Furthermore, the attachment of each one of the pair of chiral agents to a uniquely identifiable detecting agent allows rapid analysis of the reaction products by scanning methods. By "scanning methods", as used herein, it is meant that the method of analysis used (e.g., "scanning method") results in simultaneous and instantaneous analysis of reaction products.

Figure 2:
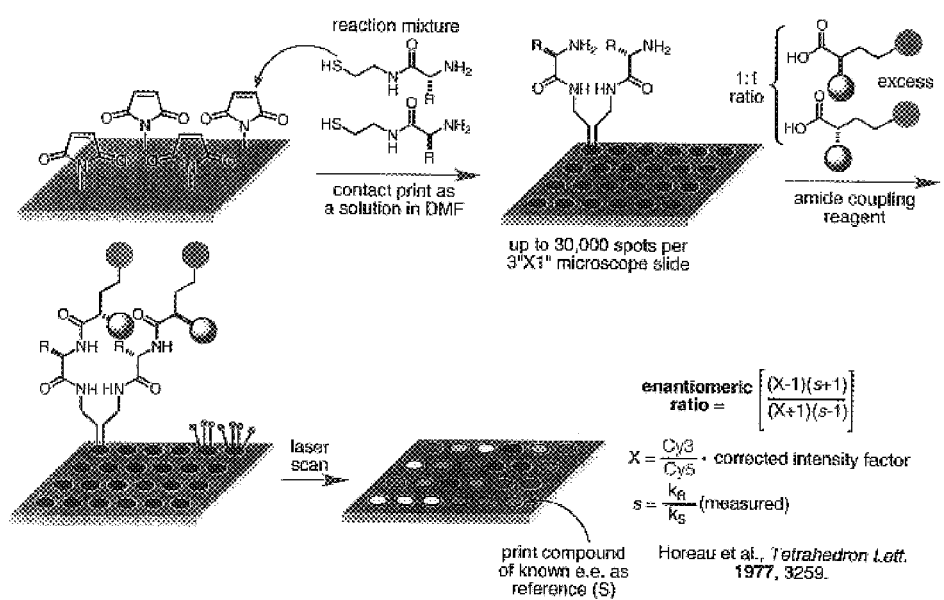
FIG. 2 depicts another embodiment of the present invention and depicts in more detail the printed samples of reaction product.

In this manner, because each chiral detecting agent reacts selectively (e.g., a kinetic resolution is effected) with a specific enantiomeric product via the chiral agent component, and has a detecting agent associated therewith, each enantiomeric product can be uniquely identified and, in addition, it is possible to quantify the amount of particular enantiomeric product formed over the competing enantiomeric product. For example, the enantiomeric ratio will be determined from the ratio of one enantiomer over another (as determined by the detecting agents, e.g., Cy3/Cy5 as depicted in the figures) factoring in a measured s value for a particular reaction being determined using Horeau's equation as shown in FIG. 2. The s value can be easily determined using a product of known e.e. and measuring the ratio (as determined by the detecting agents). FIG. 2 depicts one embodiment of the present invention in which the Cy3/Cy5 ratio is determined using a laser scanner and compared with a product of known e.e. Subsequently, the absolute configuration of the product can be determined by comparing the sign of the ratio of the presence of the detecting agents to a product of known absolute configuration. Furthermore, percent conversion can be determined by measuring the absolute intensity of each sample of reaction products divided by a sample of known quantity.

In certain other embodiments, the identifier moiety comprises a reagent that is capable of interacting selectively with a particular functional group (and not necessarily with a particular enantiomer) and thus mixtures of reaction components can be contacted with identification reagents comprising a reagent that is capable of interacting selectively with a particular functional group either prior to, simultaneously with, or after contacting with chiral detecting agent. Once the identification moiety interacts selective with a particular functionality (e.g., an amine, or other functional group), the detection reagent enables the unique identification of the functionality of interest. To clarify, it would be possible in certain embodiments to develop an identification reagent (or set of reagents) in which one of the set comprises, for example, an identification moiety capable of interacting selectively with a functional group in the starting materials, and has a unique detection agent (distinct from detection agents used in chiral detection reagents, for example) to enable determination of the amount of starting material present. By combining the information obtained from contacting with a set of chiral detecting regents and contacting with a set (or one) of identification reagents, the percent yield can be determined. Additionally, a set of identification reagents developed for a variety of functional groups and each uniquely identifiable would be useful in the "screening" of novel reactions (where an unexpected functionality is obtained, for example), or for the analysis of reaction progression.

In certain embodiments for the methods as described above and herein, the reaction products to be analyzed can be attached to a support or surface and thus are amenable to analysis as a single unit using rapid scanning techniques. This ability to rapidly scan and analyze the reaction products allows for the high throughput screening of thousands and even millions of reaction products in a short period of time, which previously has not been possible using existing methods of analysis of enantiomeric ratios and/or enantiomeric excess. The results of this ability to conduct mass screening of reaction products will enable the discovery and optimization of asymmetric catalysts, stoichiometric reagents, reactions, and reaction conditions, as well as enable the determination of important structure-activity relationships, to name a few.

Various characteristics of the method of the present invention, including certain compounds and kits, utilized in certain preferred embodiments of the present invention are discussed in more detail below. Certain examples of inventive methods, reactions and compounds are also presented, although these specific embodiments and examples are not intended to limit the scope of the present invention.

Reactions and Arrays of Reaction Products

It will be appreciated that the method of the present invention can be utilized to evaluate the components (e.g., starting materials and reaction products) from a variety of reactions, and in certain embodiments from a variety of asymmetric reactions. It will be appreciated that a variety of reaction conditions and parameters may be tested and evaluated by analyzing the products of the present invention. For example, certain parameters which can be investigated and evaluated are the discovery of novel catalysts, the discovery of novel stoichiometric reagents, the optimization of reaction conditions, and even the discovery of heretofore unknown or unachievable asymmetric reactions using known catalysts, to name a few. It will be appreciated that the reaction products from any experiment generating reaction products, and in certain embodiments, enantiomeric products, may be analyzed using the method of the present invention. Additionally, as also discussed herein, the method of the invention can be utilized to determine the chemical functionality and thus percent yields of components of a reaction mixture.

For example, in one embodiment, the analysis of any enantiomeric reaction product can be effected. Because the chiral detecting agents, as discussed herein and as described in the examples) are tailored for specific reaction (e.g., chiral acylation) with certain functionalities, as will be discussed in more detail below, the present invention contemplates the generation of one or more sets of chiral detecting reagents for any possible desirable chemical functionality. Using the principles as set forth herein, to generate a tailored set of chiral detection reagents involves: 1) selecting a desired reaction or set of reactions to analyze (e.g., chiral reduction of ketones to alcohols), 2) selecting a chiral reagent that is capable of reacting with the resulting functionality (alcohols) to generate a diastereomeric product that can be readily detected (via attachment to a detection agent, as described herein), and 3) testing the ability of the chiral reagent to interact selectively (react faster to effect a kinetic resolution) with one enantiomer present in a reaction mixture. That is, for a given pair of chiral reagents (enantiomeric pair), it is necessary to ensure that one in the pair will react selectively with one enantiomer present in a reaction mixture and that the second in the pair will react selectively with the other enantiomer present in a reaction mixture.

As but a few examples, the present invention contemplates the evaluation of reaction products of reactions including, but not limited to, Aldol reactions, enolate hydroxylations, Mannich reactions, alkylations, Diels-Alder cycloadditions, hydroboration reactions, epoxidations, dihydroxylation reactions, reduction of ketones, asymmetric synthesis of amino acids, enantioselective additions of dialkylzinc reagents to aldehydes, asymmetric hydrogenation reactions, and asymmetric aza-Diels-Alder reactions, to name a few. For a comprehensive review of asymmetric synthesis, including reactions, reaction conditions and catalysts, see "Comprehensive Asymmetric Catalysis" (Comprehensive Overviews in Chemistry), Eric N. Jacobsen (Ed.), Andreas Pfaltz (Ed.) and Hisashi Yamamoto (Ed.), Springer-Verlag: 1999, and references cited therein, the entire contents of which are incorporated herein by reference.

In addition, it will be appreciated that the reaction products of the wide variety of asymmetric reactions described above may also be produced by a variety of methods. In certain preferred embodiments, the reaction products utilized in the present invention are generated using combinatorial methods. In particular, the development of combinatorial methods for asymmetric catalysis has been of great importance to facilitate the rapid discovery of new catalysts, new reactions and improved reaction conditions. As mentioned above, however, although synthetic methods have greatly improved, the analysis of these products is still the rate limiting step, and there still remains a need to develop methods for the high-throughput screening of these reaction products.

In certain embodiments, the reaction products are generated in a combinatorial fashion and any of the following may be evaluated, although evaluation is not limited to these examples: 1) testing one "potential catalyst" against a wide variety of reactions (e.g., reduction of ketones, dihydroxylations, etc.); 2) optimizing and/or varying reaction conditions (e.g., varying different reaction conditions such as metal, ligand, temperature, time, concentration, additives, and substrates, to name a few); or 3) testing a large number of "potential catalysts" (e.g., variations in metals, ligands, or additives, to name a few) for the ability to catalyze one particular reaction of interest. In this fashion, in certain embodiments, as many as, or more than, 10,000 reaction products can be generated for analysis. It will be appreciated, however, that the method of the present invention can be utilized for the analysis of as few as one sample of reaction products, and as many as several million, or more, reaction products.

In certain embodiments, these reaction products are then "printed" on, or attached to a material of interest. It will be appreciated that any material geometry, e.g, flat, round, elliptical, to name a few, may be utilized, although in certain preferred embodiments the material contains a flat surface for rapid analysis of a "sheet" of material. Exemplary materials include, but are not limited to, glass, polymer, metals (e.g., gold), and silicon to name a few. Additionally, these materials may include beads, solid surfaces, solid substrates, particles and supports. Certain examples of these include, but are not limited to, glass slides, beads, pellets, disks, capillaries, pore-glass beads, silica gels, polystyrene beads optionally cross-linked with divinylbenzene, latex beads, glass particles, and flexible membrane supports, and soluble supports.

It will be appreciated that, in general, any appropriate material having a functional moiety capable of reacting with an appropriate functionality present in the reaction product to effect attachment can be utilized. In certain embodiments, the material also comprises a material that does not interfere with the direct analysis of the reaction products attached to the surface once exposed to the identification (or chiral detecting) agents.

Figure 3:
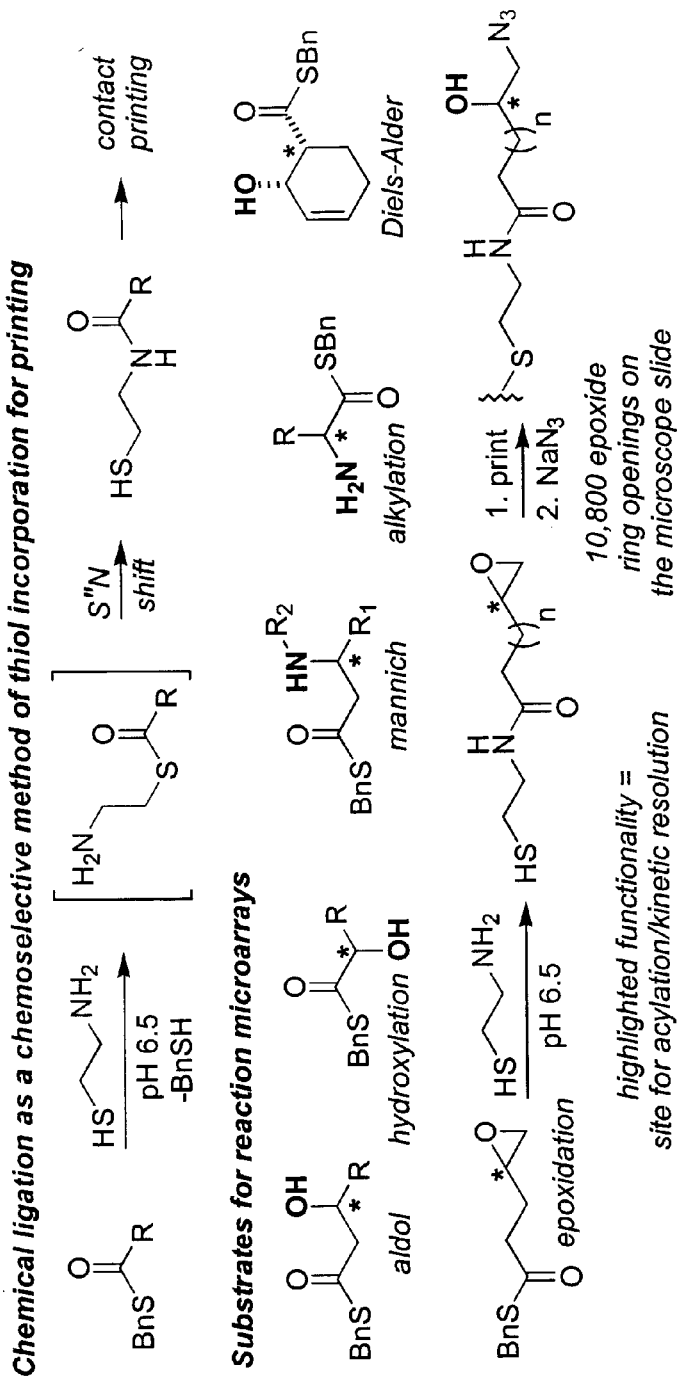
FIG. 3 depicts the use of chemical ligation as a chemoselective method of thiol incorporation for printing and also depicts certain substrates for use in the method of the present invention.
Figure 4:
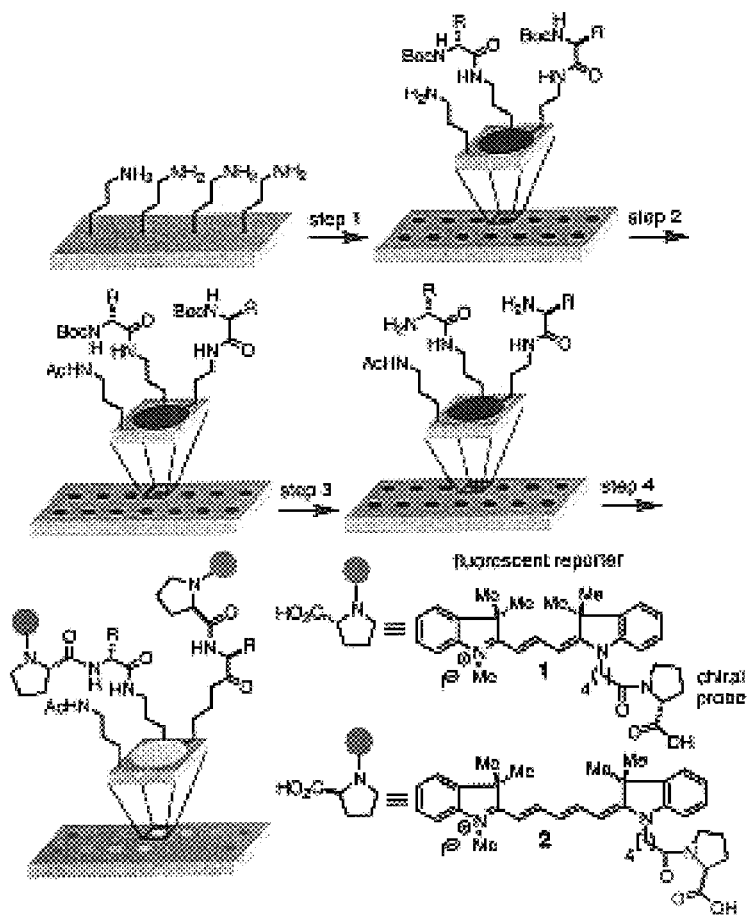
FIG. 4 depicts the printing of N-Boc protected α-amino acids onto amine-functionalized glass slides and the contacting of the amino acids with pseudoenantiomeric fluorescent probes 1 and 2.
Figure 5:
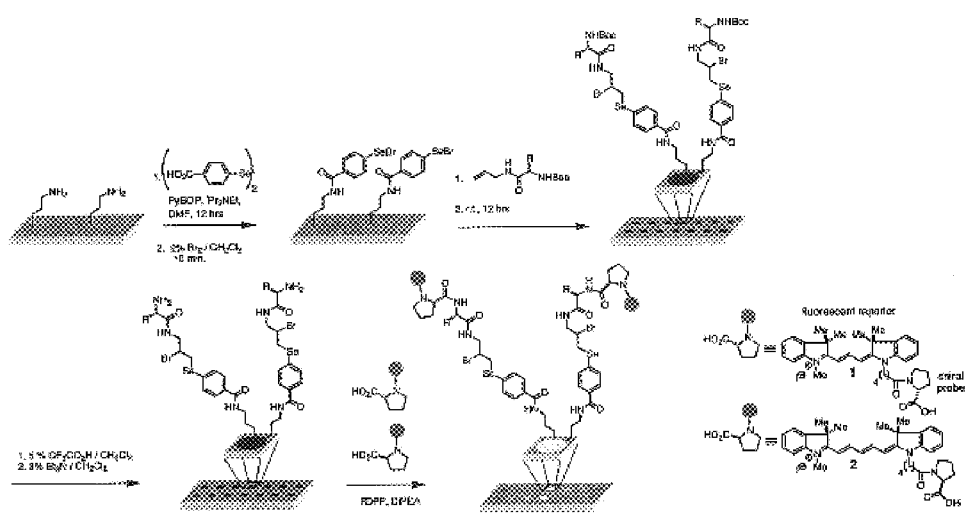
FIG. 5 depicts the attachment of amino acids as their allyl amides to selenyl bromide-functionalized microslides.
Figure 6:
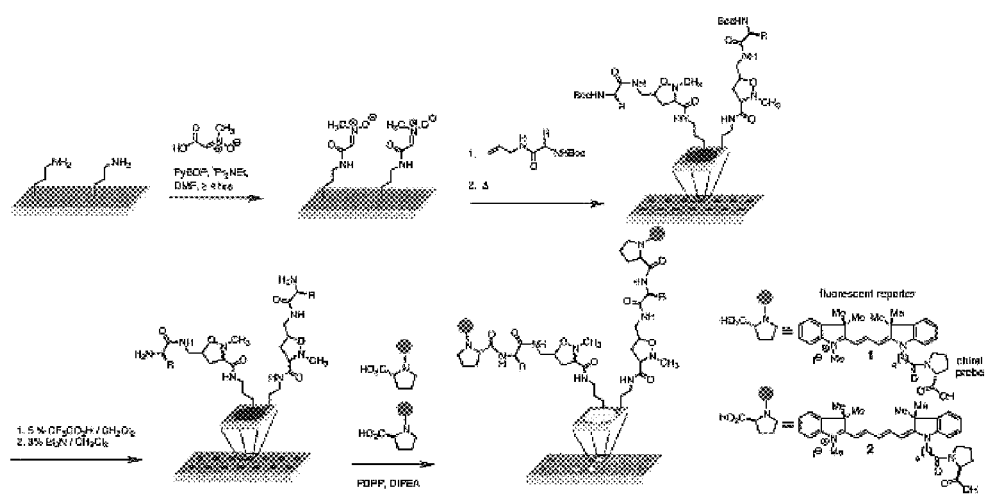
FIG. 6 depicts the attachment of amino acids as their allyl amides to nitrone-functionalized microslides.
Figure 7:
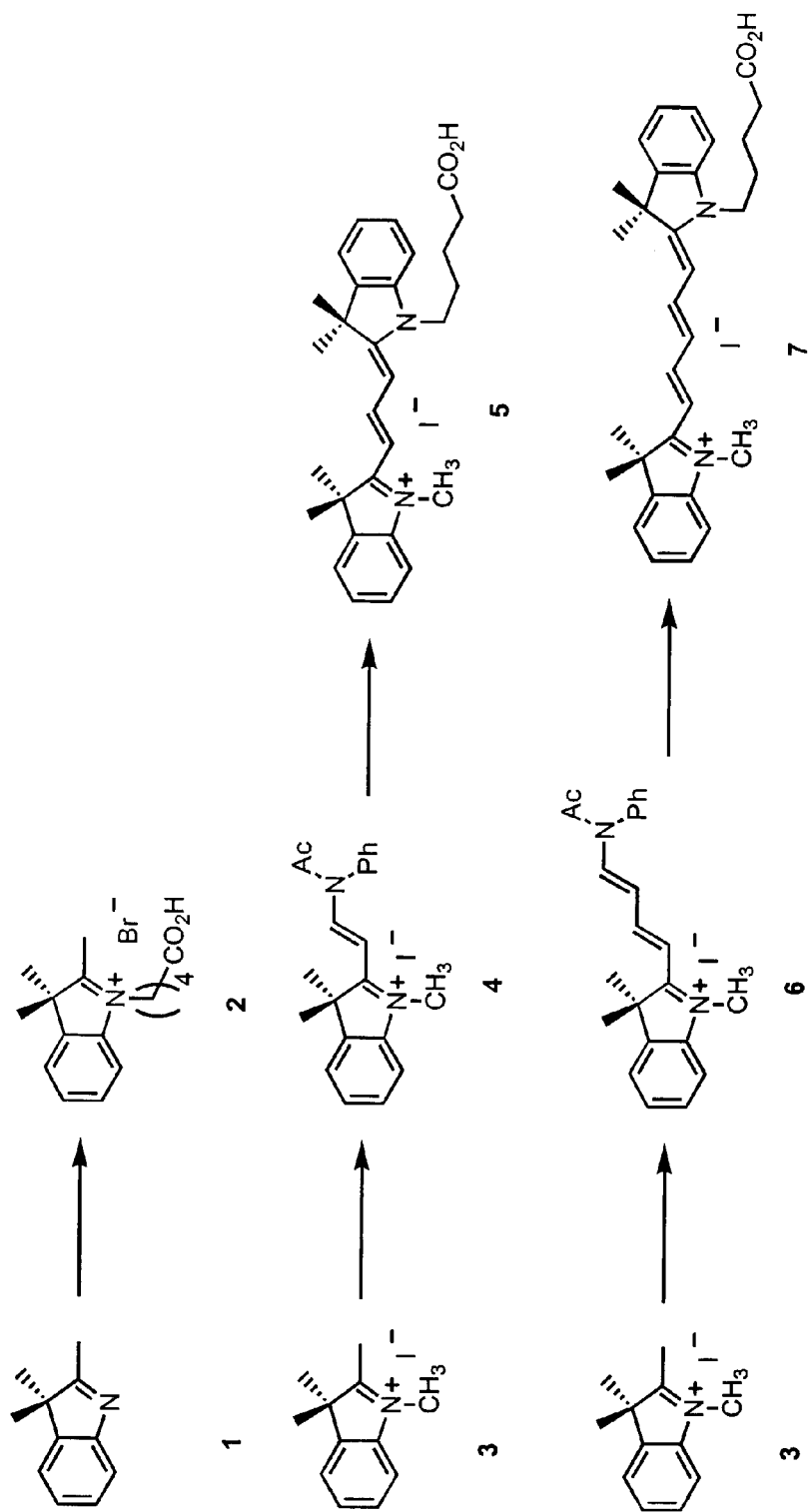
FIG. 7 depicts a scheme for the synthesis of indocarbocyanine and indodicarbocyanine fluorophores.
Figure 8:
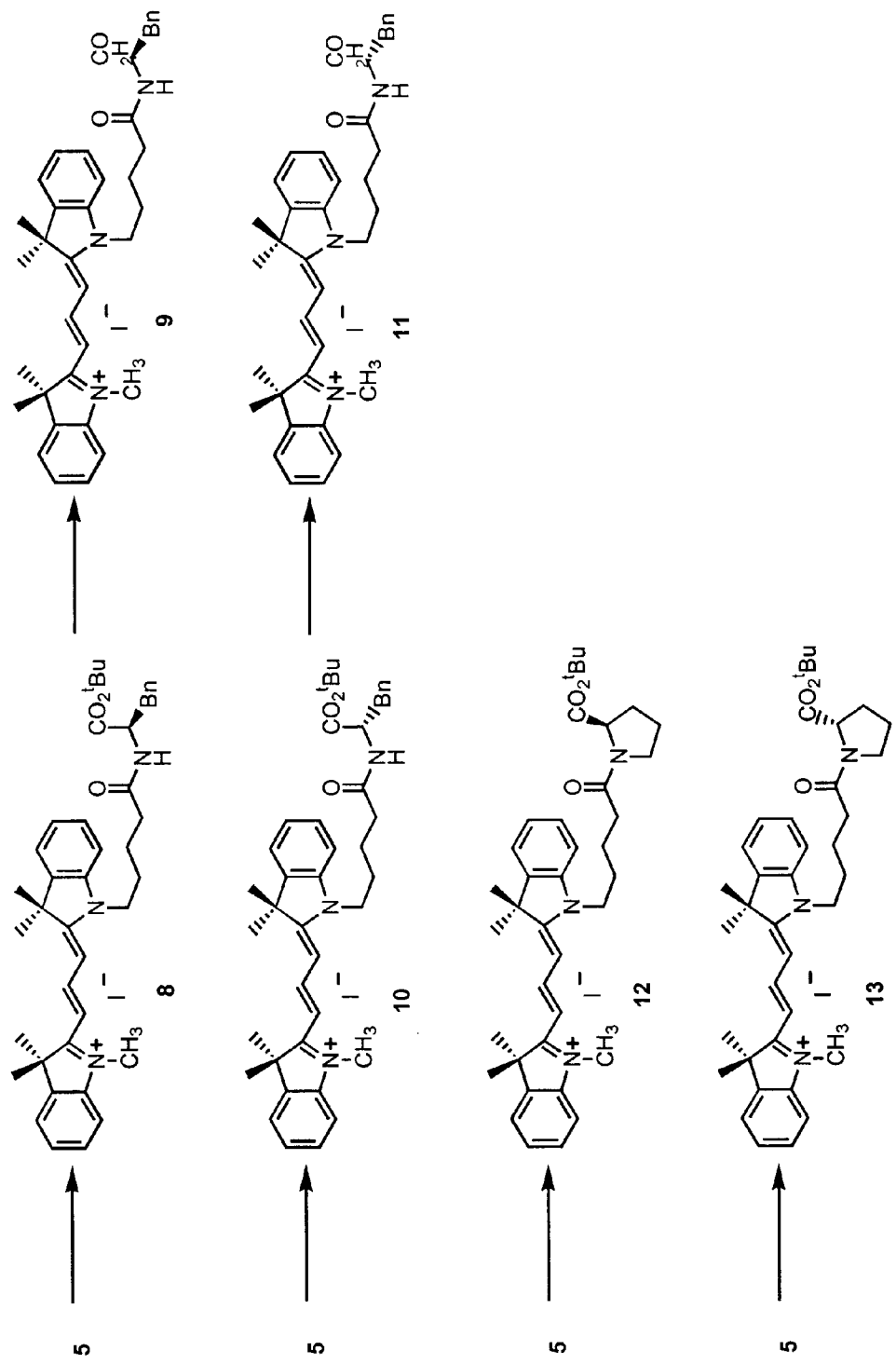
FIG. 8 depicts the synthesis of Cy3 fluorophore conjugates by ${}^t$Bu-protected amino acids.
Figure 9:
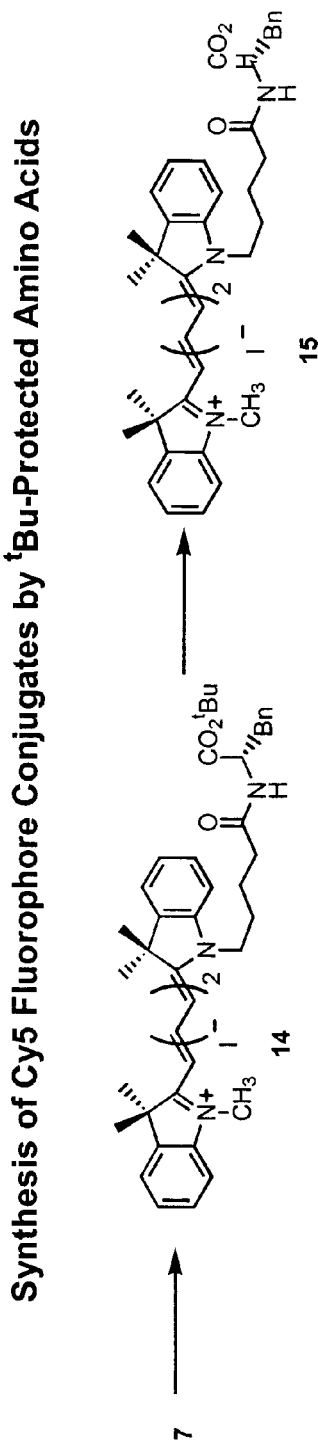
FIG. 9 depicts the synthesis of Cy5 fluorophore conjugates by ${}^t$Bu-protected amino acids.
Figure 10:
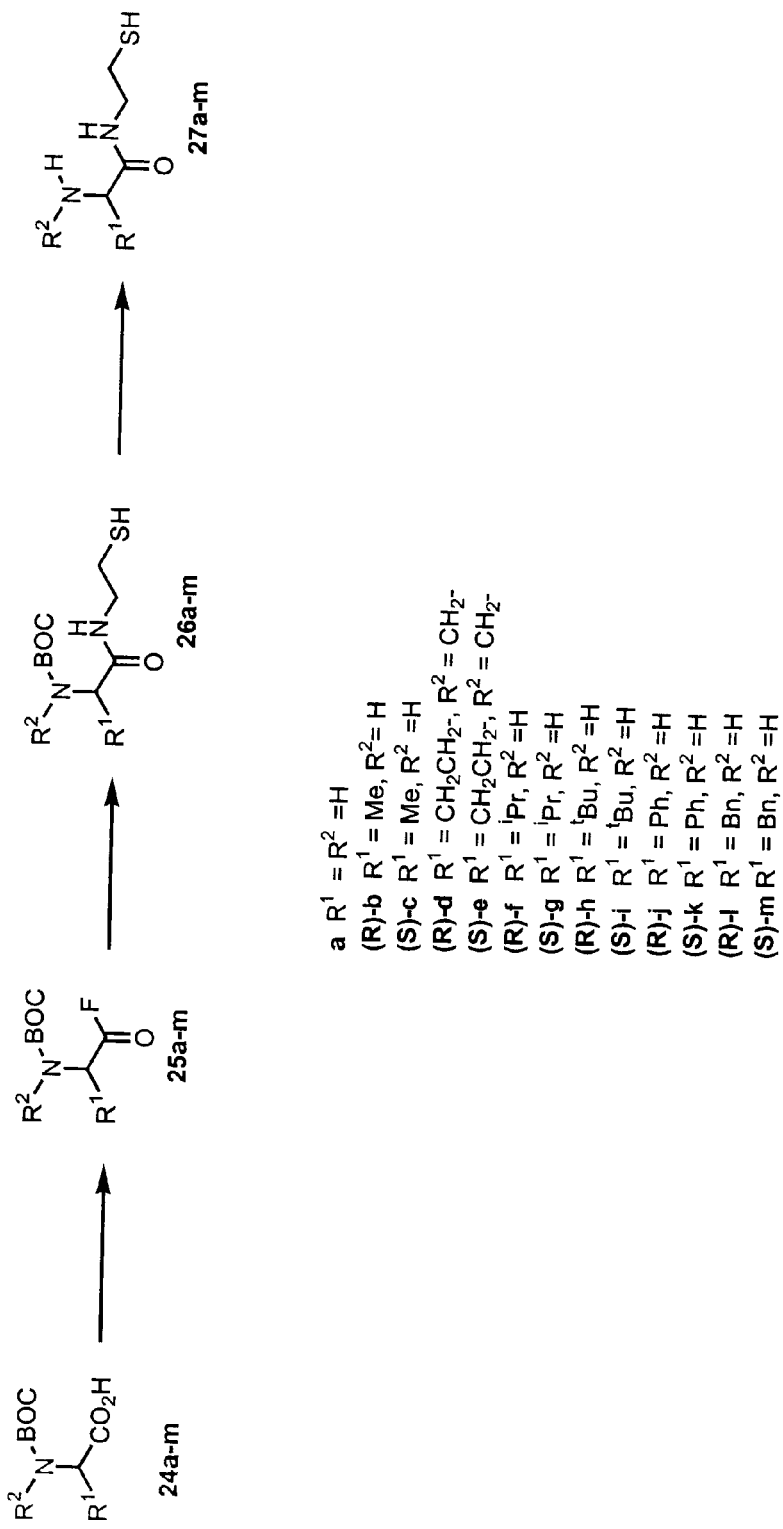
FIG. 10 depicts the synthesis of amino acid substrates for printing.
Figure 11:
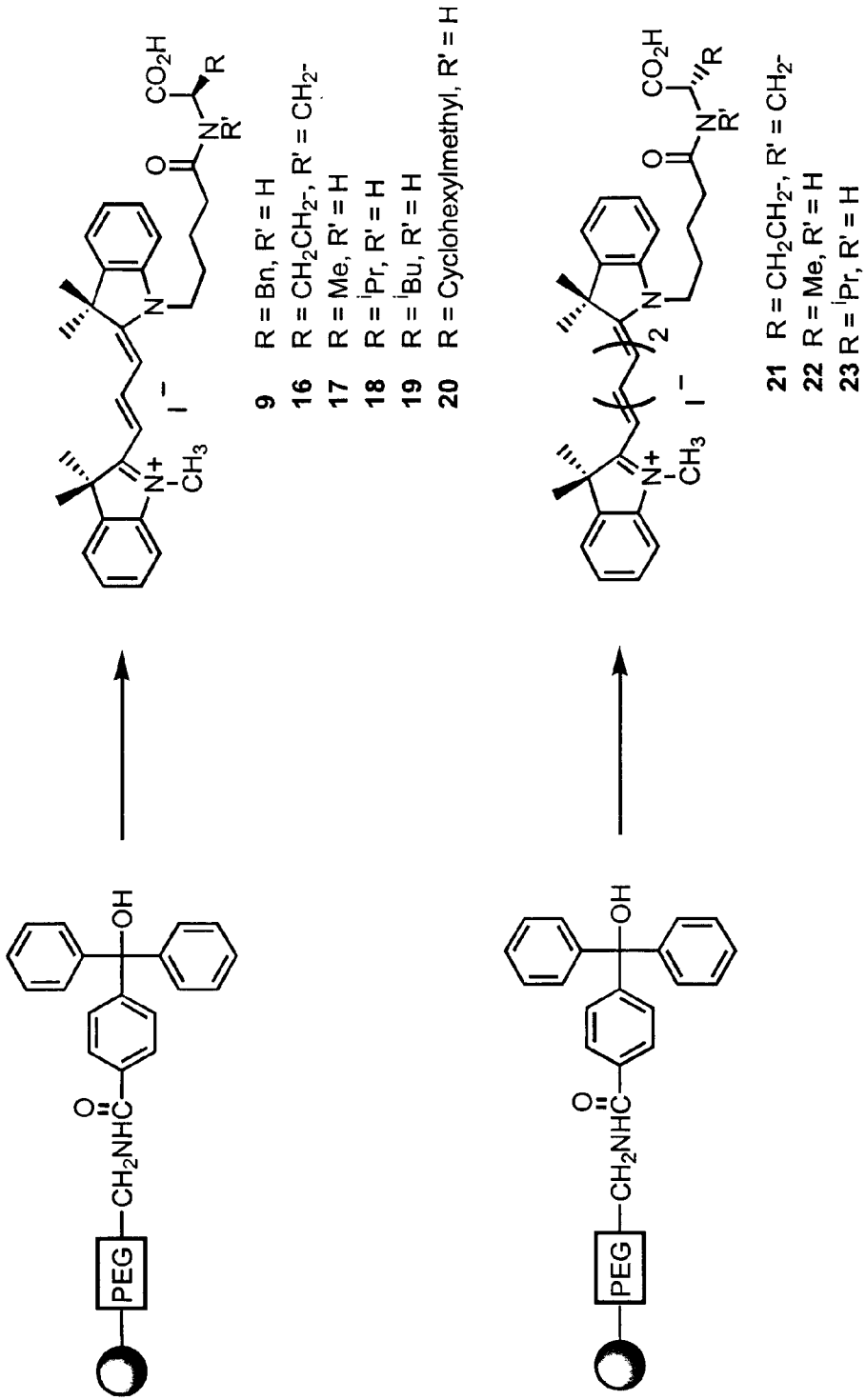
FIG. 11 depicts the solid phase synthesis of cyanine-amino acid conjugates.
Figure 12:
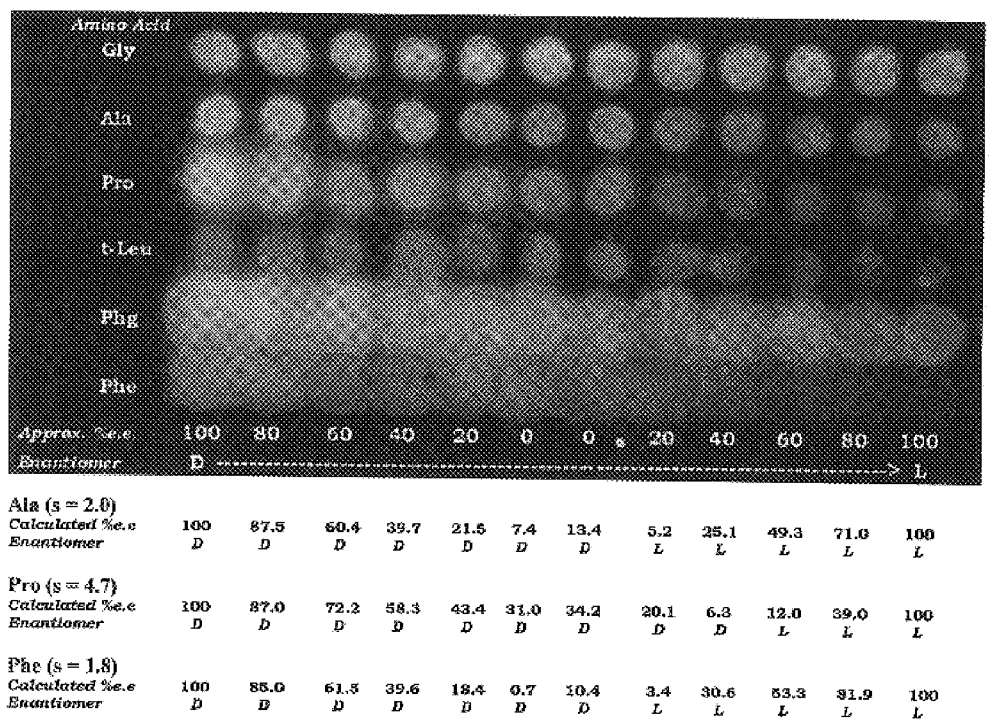
FIG. 12 depicts changes in ratios of fluorescence intensity and the calculated values of s and percentage enantiomeric excess for the chiral amino acids alanine, proline and phenylalanine.
Figure 13:
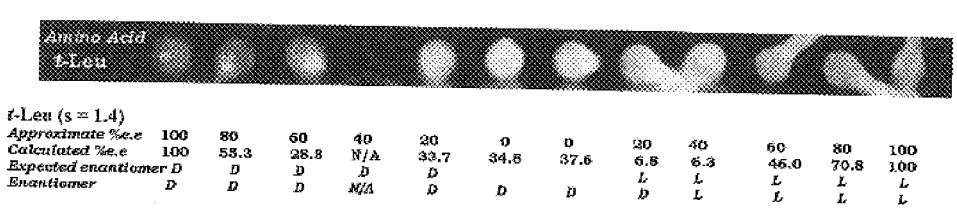
FIG. 13 depicts the changes in ratios of fluorescence intensity and the calculated values of s and percentage enantiomeric excess for the chiral amino acid tert-leucine.

In one exemplary embodiment, reaction products from a desired reaction or set of reactions are printed onto a glass surface. Certain methods of attachment of the reaction products to the slide include, but are not limited to carbenoid-based insertion reactions, thiol-maleimide conjugate addition reactions (for example, thioesters produced by specific reactions can be modified using chemical ligation to generate thiols for the conjugate addition), attachment of alcohols via thionyl chloride modified surfaces, and conjugate additions with hydrazine amides to name a few. FIG. 3 depicts exemplary substrates for reaction microarrays and the chemical ligation method as one example of thiol incorporation for printing. FIG. 4 depicts the attachment of reaction products to amines present on the slide surface. Additionally, FIG. 5 depicts (and the examples describe) the attachment of amino acids as their allyl amides via reaction with selenyl bromide-functionalized microslides. FIG. 6 also depicts the attachment of amino acids as their allyl amides to nitrone-functionalized microslides (as also described in the examples). It will be appreciated, however, that other methods of attachment can be utilized, specifically taking into account the finctional groups present in the reaction products and the material to be printed onto. Specific factors to take into consideration for the attachment or printing of reaction products include 1) ensuring that the linkage is robust enough so that the substrates are not inadvertently cleaved during the analysis and 2) ensuring that the functionalities are inert, that it, they do not interfere with the subsequent analysis.

In certain embodiments, the reaction products are robotically contact printed and covalently attached to the surface at a density of 10,800 spots per slide or more, following recently reported protocols (see, Schreiber et al., and patent application Ser. Nos. 60/133,595 and 09/567,910) entitled "Small Molecule Printing", the entire contents of which are incorporated herein by reference) In certain embodiments, each spot contains approximately 0.02 nmoles of product from one of 10,800 reactions. Whether 10,000 reaction products, fewer than 10,000, or more than 10,000 reaction products are printed, it is possible to use a variety of printing techniques. For example, techniques including, but not limited to, contact printing, piezoelectric printing, and ink jet printing can be utilized in the method of the present invention.

The foregoing description is intended to present certain embodiments of the present invention and is not intended to limit the scope of the present invention. It will be appreciated that any method of printing and covalent attachment may be utilized which results in the generation of reaction samples capable of being analyzed using the method of the present invention.

Identification Agents and Analysis

In another aspect of the present invention, identification reagents are provided for use in the method of the present invention, which reagents comprise an identifier moiety and a detection agent, whereby said identifier moiety is optionally attached to the detection agent via a linker. In general, the identification reagent can be described using the following formula:

IA=IM-DR wherein IM is the identification moiety and DR is the detection reagent. As described above, the method of the present invention takes advantage of the ability of one identification reagent in a pair (or set) to react selectively (e.g., reaction occurs faster to effect a kinetic resolution, or occurs because of functional group selectivity) with one or more components of a reaction mixture over one or more of the other components. For example, a set of identification reagents can be provided to identify functional groups (and thus to potentially determine % yield or to screen new reactions), or to determine enantiomeric excess (by selective reaction with one enantiomer over another).

In certain embodiments, the identification reagents are utilized to determine the chirality of a molecule and thus the identification reagents are chiral detecting reagents comprising: 1) a chiral agent and 2) a detection agent, whereby said chiral agent is optionally attached to the detection agent via a linker. In general, the chiral detecting agents of the present invention can be described using the following general formula:

CDR=DR-CR where the chiral detecting reagent (CDR) comprises a detecting reagent (DR) and a chiral reagent (CR). In certain embodiments, the detecting reagent (DR) and the chiral reagent (CR) are connected via a linker moiety (L) to generate a compound having the following general formula:

CDR=DR-L-CR

As discussed above, the method of the present invention utilizes the ability of chiral detecting agents to selectively react (i.e., react faster) with one enantiomer over another competing enantiomer. Thus, according to the method of the present invention, each enantiomeric form of a particular chiral agent present in the chiral detecting agent is capable of selectively reacting with one enantiomer of the reaction products over the other. That is, chiral agent ($A_r$) is capable of reacting selectively (i.e., faster) with only one of the enantiomeric products, while chiral agent ($A_s$) is capable of reacting selectively (i.e., faster) with only the other enantiomeric product (that did not react in that manner with chiral agent $A_s$). As discussed previously, selecting a particular chiral reagent for the chiral detecting reagent, the particular reaction to be analyzed must be taken into consideration to ensure that, for the set of chiral detecting reagents employed, each chiral detecting reagent within the set will contain a functionality that is capable of interacting with the reaction product, but will also react selectively with one enantiomeric product over the other. That is, in the method of the present invention, any chiral group may be utilized that is capable of effecting a kinetic resolution, as described herein, by forming a covalent bond or interaction with the substrate and producing a diastereomeric product that can be readily detected.

In certain embodiments, chiral amino acids are utilized as the chiral reagents in the method of the present invention. Exemplary amino acids include, but are not limited to, alanine, proline, t-leucine, pipicolinic acid, and phenylalanine. It will also be appreciated that, in addition to these particular amino acids, di- or tri-peptides could also be utilized in the method of the present invention. Still other chiral agents to be utilized in the method of the present invention include, but are not limited to alkaloids such as cinchona derivatives, ephedrine, emetine, sparteine, strychnine, and brucine to name a few. Additionally, sugars, camphor derivatives, menthol derivatives, cyclohexyl derivatives, 8-membered ring derivatives, hydroxy acid derivatives and appropriately functionalized BINOL or BINAP derivatives can be utilized, to name a few. The following references also provide a discussion of some of these chiral agents (Blaser et al. *Chem. Rev.* 1992, 92, 935; Whitesell et al. *Chem. Rev.* 1992, 92, 953–964), the entire contents of which are incorporated herein by reference.

In addition to a chiral reagent, the chiral detecting reagent, or more generally an identification reagent, also comprises a detecting component, or a detecting reagent. As used herein, the detecting reagent is any agent capable of being uniquely detected using scanning methods, as described herein. Exemplary detecting reagents include those agents that are excitable (e.g., photosensitive or fluorescent), radioactive, or chemiluminescent, to name a few, and that are capable of simultaneous and instantaneous or nearly instantaneous detection. These methods are particularly useful for large arrays of materials and enable the high-throughput determination of reaction identity (e.g., functionality, enantiomeric ratios, etc.)

In certain embodiments, photosensitive detecting agents are utilized, for example dyes. In certain other embodiments, fluorescent dyes are utilized particularly those that have a fluorescence between about 500 and 900 nm. Preferred detecting agents are also photostable and are not prone to aggregation. As mentioned above, the identification reagents, or chiral detecting agents, as used in the present invention, comprise a set (or pair) of agents, each one reacting preferentially with one reaction component (or enantiomer) over another. Thus, the identification and chiral detecting agents of the present invention also comprise a detecting agent capable of uniquely identifying one reaction component or enantiomer over another after the interaction with the reaction component or enantiomer, which ultimately enables detection, analysis and determination of desired properties (e.g., functionality or enantiomeric ratios, to name a few). Fluorescent dyes are particularly useful in this regard, because small changes in the dye structure yields compounds that fluoresce in different regions of the spectrum and thus are readily identifiable and quantifiable using scanning methods.

Although any detection reagent, as described above can be utilized in the method and kits of the present invention, in certain embodiments, the present invention provides chiral detecting agents having the general structural formula (I). These agents incorporate fluorescent dyes as the detecting agent and also incorporate a chiral reagent.

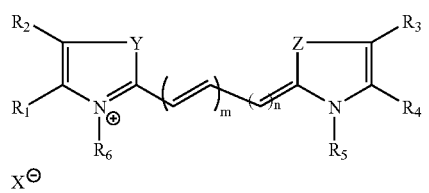

wherein $R_1$ and $R_2$, and $R_3$ and $R_4$ taken together each independently comprise a substituted or unsubstituted cyclic or polycyclic aryl or heteroaromatic moiety; wherein m is 1, 2, or 3; wherein n is 0 or 1; wherein Z or Y each independently comprise —C(R)$_2$—, wherein each occurrence of the functional moiety R is independently selected from the group consisting of hydrogen and methyl; NR, wherein R is selected from the group consisting of hydrogen and methyl; O; S; or Se; wherein X is a non-coordinating negative counter ion including, but not limited to $BF_4$, $PF_6$, $ClO_4$, TsO, I, Br; and wherein $R_5$ or $R_6$ each independently comprise lower alkyl, a chiral reagent (CR) or a chiral reagent and linker (L-CR), whereby said chiral reagent is attached to the detecting agent via the linker. In certain embodiments, the linker moiety comprises —(CH)$_p$—(CO)—, wherein p is 1–5, most preferably 4, and the chiral agent comprises a chiral acylating agent, as described in certain embodiments herein. In certain embodiments, the chiral agent comprises a chiral acylating agent having the general structure: —(NH)—(CHR$_x$)—COOH, where R$_x$ comprises a chiral amino acid residue. In certain other embodiments of the present invention, the chiral reagent (CR) or the chiral reagent and linker (L-CR) can be attached at any one of $R_1$–$R_6$, or as substitutions of other moieties thereof attached at $R_1$–$R_6$ (e.g, the chiral reagent or chiral reagent and linker can be attached via an aryl moiety or other functional group).

In yet another aspect, the present invention provides kits comprising a pair of chiral detecting agents, wherein both the chiral agent and the detecting agent are tailored to specific reaction products desired to be analyzed. In certain embodiments, these kits comprise a set of chiral detecting reagents wherein at least one of said pair in said set comprises the formula (I) as described above, wherein each of said chiral detecting agents in said pair selectively reacts with and uniquely identifies one reaction product over the other. In certain other embodiments, the kits include at least one set of identification reagents useful for the identification of one or more functional groups and for the determination of percent yield.

It will be appreciated that although certain embodiments of the chiral detecting reagents are described herein, the scope of the present invention is not limited to these embodiments, or those described in the experimental details, and thus encompass any reagent capable of 1) selectively reacting with one enantiomer over another and 2) uniquely identifying that enantiomer, thus enabling rapid identification and analysis.

Uses

The present invention provides methods for rapidly analyzing reaction products from reactions, specifically enabling the determination of enantiomeric ratios, percent conversions, and absolute configurations. By analyzing products directly from reaction mixtures, the screen can be used for catalyst discovery and optimization using standard or combinatorial approaches.

In one embodiment, the method of the present invention utilizes microarrays of reaction products, namely reaction microarrays. An advantage of the use of reaction microarrays for catalyst discovery using combinatorial methods is the determination of enantiomeric ratios from every reaction, as opposed to other screens that may identify only a few catalysts that give the highest enantiomeric ratios. A large amount of information can be extracted from each set of experiments relating catalyst structure, additives and conditions to the degree of asymmetric induction and reaction conversion. Encoded within this data are important trends that would not have been uncovered by screens that only identify the most active catalysts. In analogy to the development of bioinformatics resulting from DNA microarrays, chemical informatics programs will be necessary in order to organize and mine the data returned by reaction microarrays from tens-of-thousands of catalysis experiments or more. Reaction microarrays can also help to accelerate catalysis discovery by lowering the barrier to attempting catalytic enantioselective reactions with new and unorthodox chiral ligand-metal combinations. The information returned by these experiments may lead to a better understanding of the complex chemical forces involved in asymmetric catalysis and the development of novel catalysts.

In addition to the use of reaction microarrays for the analysis of reaction products (the reactions for which were completed in another reaction vessel), the method of the present invention also contemplates the use of reaction microarrays to perform the reactions themselves on the microarrays. Thus, in one embodiment, first a surface (e.g., glass slide) can be finctionalized with desired reaction substrates (Y), then a series of reagents X1, X2, etc., can be generated in a multiwell format (in a combinatorial approach) (e.g., 384 well plate or multiple 384 or other dimension well plates). Subsequent printing of the reagents (X1, X2, etc) onto the surface printed with reaction substrates (Y) leads to direct reaction on the surface, the reaction products of which can then be directly analyzed using scanning methods. Thus, reaction and analysis can both be automated to provide an effective high throughput technique.

Still other uses for the method of the present invention include, but are not limited to, screening for suicide inhibitors of enzymes, screening of catalytic antibodies, evaluating levels of enzymatic activity (for example, ester hydrolysis, or amide cleavage by the enzyme, followed in a separate step by acylation/attachment of a chiral detecting agent), and evaluating the stereospecificity of the enzyme. Furthermore, the method of the present invention could also be utilized to analyze the kinetics of a reaction and monitor the course of a given reaction by arraying the reactions at different times.

It will be appreciated that the method of the present invention is not limited to the uses described above, or in the specification; rather the method of the present invention is generally applicable and other uses of the present invention are intended to be within the scope of the present invention.

Equivalents

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification and guidance which can be adapted to the practice of this invention in its various embodiments and the equivalents thereof.

Exemplification
Experimental Description Certain Embodiments of the Invention 1) Referring to FIG. 1, in which a specific embodiment of the present invention is depicted, reaction products from an aldol reaction are functionalized with a free thiol, and are then robotically contact printed and covalently attached to maleimide-functionalized microscope slides. FIG. 2 depicts another general scheme for the inventive reaction microarrays in which 30,000 samples are printed, and also further depicts printed reaction "spots" containing the sample of reaction product to be screened. The slide is then exposed to a 1:1 mixture of excess chiral detecting reagents, 2 and 3 as depicted in FIG. 1, in the presence of reagents described herein. Reagents 2 and 3 (as shown in FIG. 1), contain enantiomeric amino acids that have each been attached separately to Cy3 or Cy5 fluorescent dye. Exposure of the slide to excess 2 or 3 under acylation conditions results in 10,800 simultaneous kinetic resolutions. Using the equation reported by Horeau (Horeau et al. *Tetrahedron Lett.* 1977, 3259), the enantiomeric ratio for each reaction is determined from the Cy3/Cy5 ratio at each spot factoring in the measured s value for the acylation reaction. The s value is easily determined by printing one spot with a product of known e.e. and one racemic spot, and measuring the Cy3/Cy5 ratio of each of these spots. Following 10,800 simultaneous kinetic resolutions, a laser scanner is used to rapidly (15 minutes or less) measure the Cy5/Cy3 ratio at each of the 10,800 spots. The equation, as depicted in FIGS. 1 and 2 is then used to determine the enantiomeric ratio of each reaction. Furthermore, the absolute configuration of the product from each reaction is determined by comparing the sign of the Cy3/Cy5 ratio to a spot that was printed using a product of known absolute configuration. The percent conversion of each reaction is determined by measuring the absolute fluorescence intensity at each spot divided by a spot of known quantity.

2) Referring to FIG. 4, samples of N-Boc protected α-amino acids were arrayed and covalently attached to amine-functionalized glass slides. Automated contact printing of nanoliter volumes from 2 mM solutions chemoselectively attached $<10^{-11}$ moles of amino acid to each spot on a glass slide in a spatially arrayed manner (FIG. 4, step 1). Uncoupled surface amines were acetylated (step 2) and en mass Boc-deprotection yielded the free amino of the amino acids (step 3). In analogy to DNA microarrays, where relative gene expression levels are measured by a ratio of fluorescent reporters, reaction microarrays utilize two fluorescent probes to measure a ratio of enantiomers (step 4).

Referring to FIG. 4, pseudoenantiomeric fluorescent probes 1 and 2 combine a fluorescent reporter with a chiral probe and are synthesized by coupling Cy3 and Cy5 fluorophores to D- and L-enantiomers of proline, respectively. These chiral fluorescent probes are covalently attached to the immobilized amino acid samples by exposing the glass slide to an excess of an equimolar mixture of 1 and 2 under amide coupling conditions. Parallel kinetic resolution during the amide coupling reaction converts the ee information of the sample into a ratio of fluorophores that, upon excitation by an automated laser scanner, is observed as a ratio of fluorescent intensities. Fluorescence emission is measured following excitation of Cy3 at 532 nm and excitation of Cy5 at 635 nm. The resulting image is false-colored with Cy3 fluorescence represented as green and Cy5 fluorescence represented as red. Equivalent fluorescent emission intensity of Cy3 and Cy5 is yellow.

$$\% \ ee = [((x-1)(s+1))/((x+1)(s-1))] \times 100\%;$$

where $x = I_{fluor, Cy5}/I_{fluor, Cy3} \times 1/z$ and $s = k_{fas}/k_{slow}$ \hfill (Eq. 1)

An extension of quantitative studies on the kinetic resolution of secondary alcohols provides a relationship (equation 1) between ee and the measured fluorescent intensity ratio at each spot. The ratio of fluorescent intensities of 1 and 2 is divided by a normalization factor, z, to account for non-equivalent equimolar fluorescent intensities of Cy3 and Cy5. For any substrate, the value of z is defined as the fluorescent intensity ratio of the racemate. The value of s quantifies the kinetic resolution and is obtained from z and the measured value of x for a sample of known ec. For 100% ee, eq. 1 simplifies to s=x. Previous work (Horeau, A. In Stereochemistry: Fundamentals and Methods; Kagan. H. B., Ed.; Thieme, Stuttgart, 1977; Vol. 3, pp. 51–94; Guo, J. et al.

*Angew. Chem., Int. Ed.* 1999, 38, 1755) has shown that perfect recognition is not necessary and that small s values are sufficient for accurate determination of ee.

Figure 14:
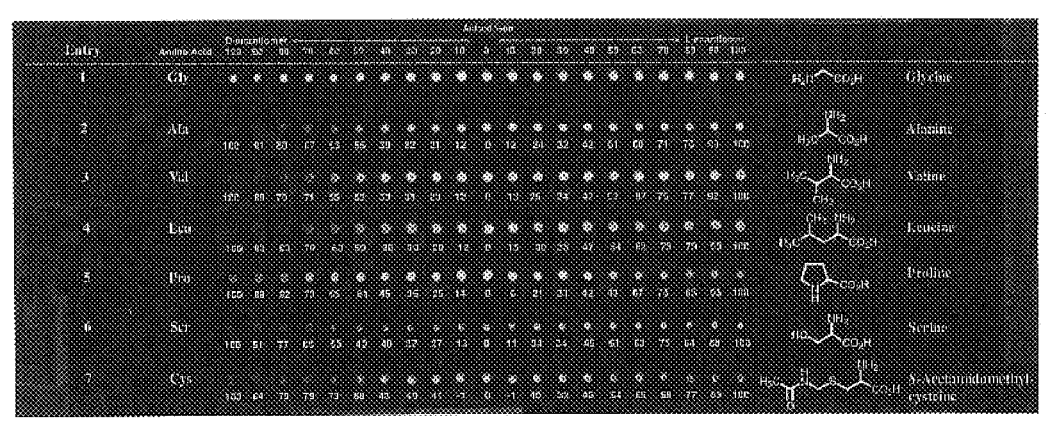

The accuracy of this method was tested on structurally diverse α-amino acids of varying ee (FIG. 14). The glass slide was arrayed with Gly, Ala, Val, Leu, Pro, Ser, and Cys and treated as described in FIG. 4. The six chiral amino acids were printed as mixtures of enantiomers ranging from 100% ee D to 100% ee L in steps of 10% ee. The achiral α-amino acid Gly produced yellow spots (equivalent incorporation of red and green fluorophores), indicating no preference for either chiral probe. The six chiral amino acids exhibited a noticeable change of spot color in the progression from one enantiomer to the other, and more importantly, measured ee values correlated well with actual ee values. The red or green color of each spot can be used to assign the absolute configuration of the predominant enantiomer in each sample when correlated to the color of a sample of known absolute configuration. Observed s values ranged from 1.2 to 3.6, with higher values generally corresponding to more accurate ee measurements. Standard error of the mean was <8% ee in all but one sample, and the average measured ee values of 116 out of 126 samples (92%) were within ±10% ee of the actual value.

Figure 15:
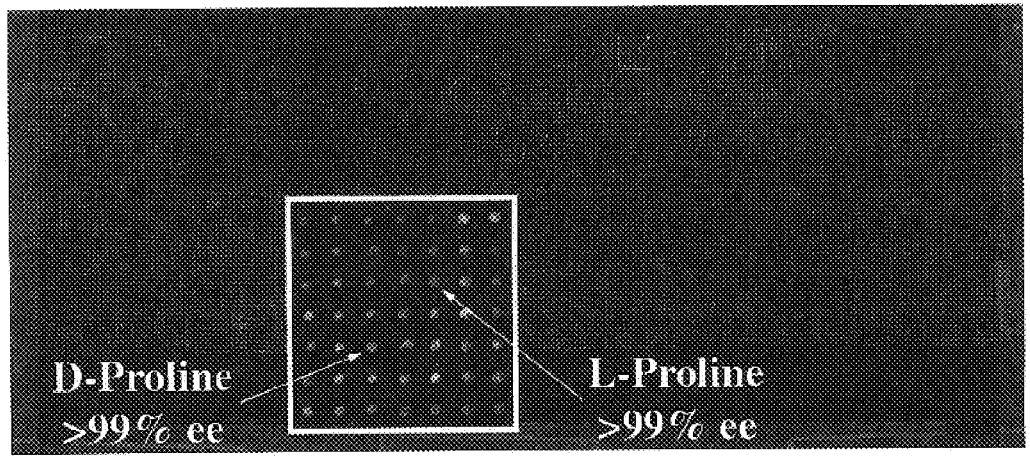
FIG. 15 depicts the identification of two >99% ee samples of proline in a collection of 15,552 samples.
Figure 16A:
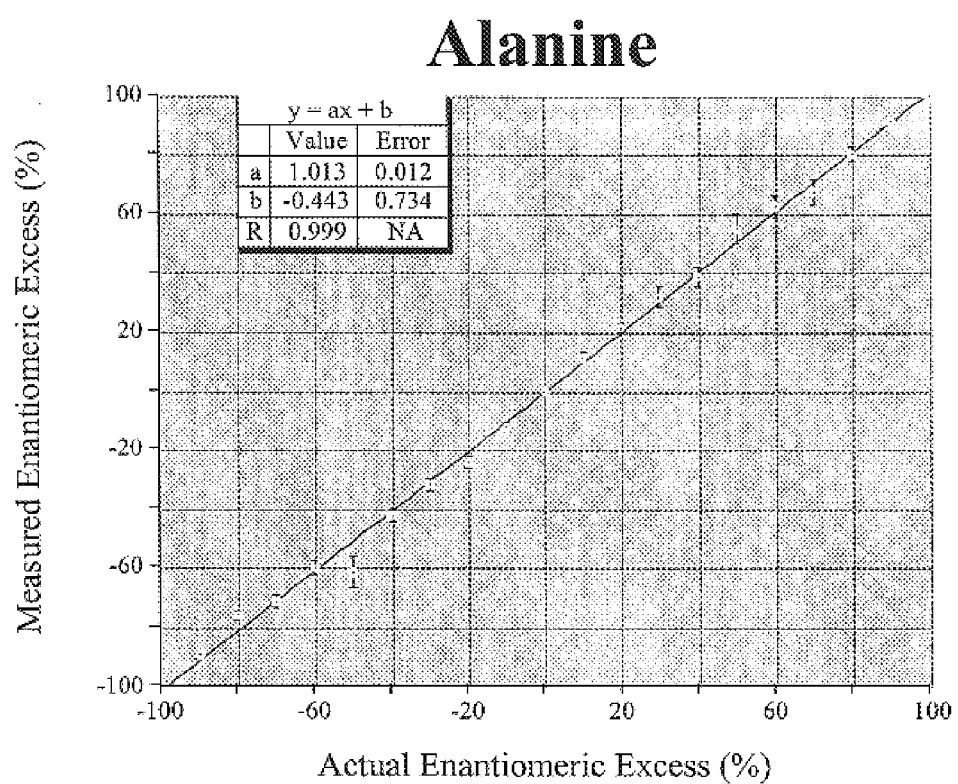
FIG. 16 depicts an exemulary graph representing Alanine kinetic resolution and enantiomeric excess calculation.
Figure 17A:
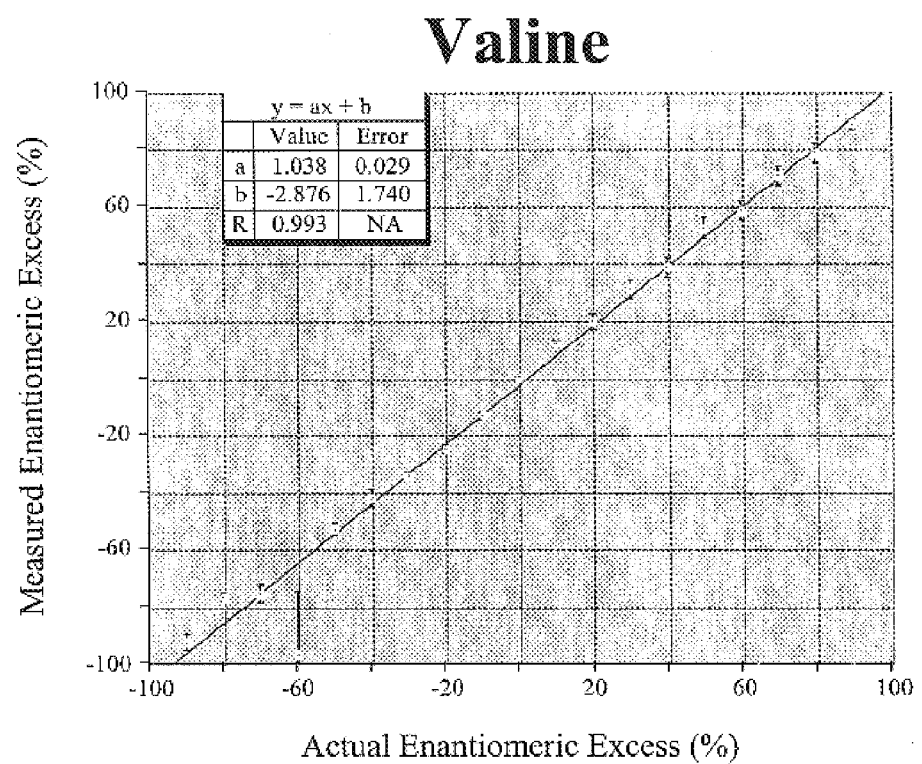
FIG. 17 depicts an exemplary graph representing Valine kinetic resolution and enantiomeric excess calculation.
Figure 18A:
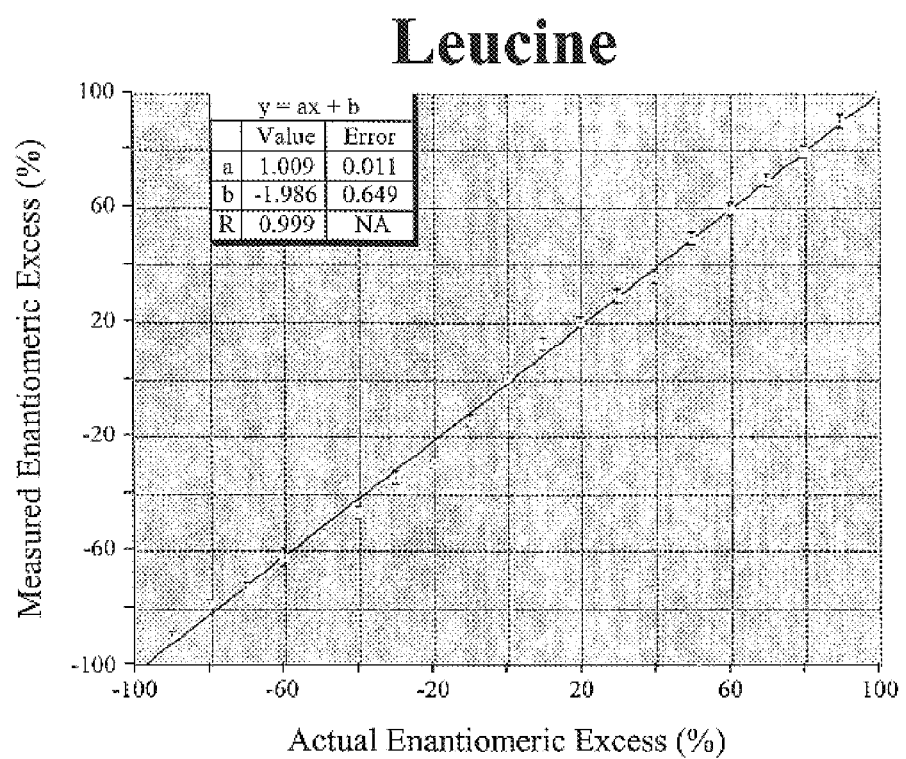
FIG. 18 depicts an exemplary graph representing Leucine kinetic resolution and enantiomeric excess calculation.
Figure 19A:
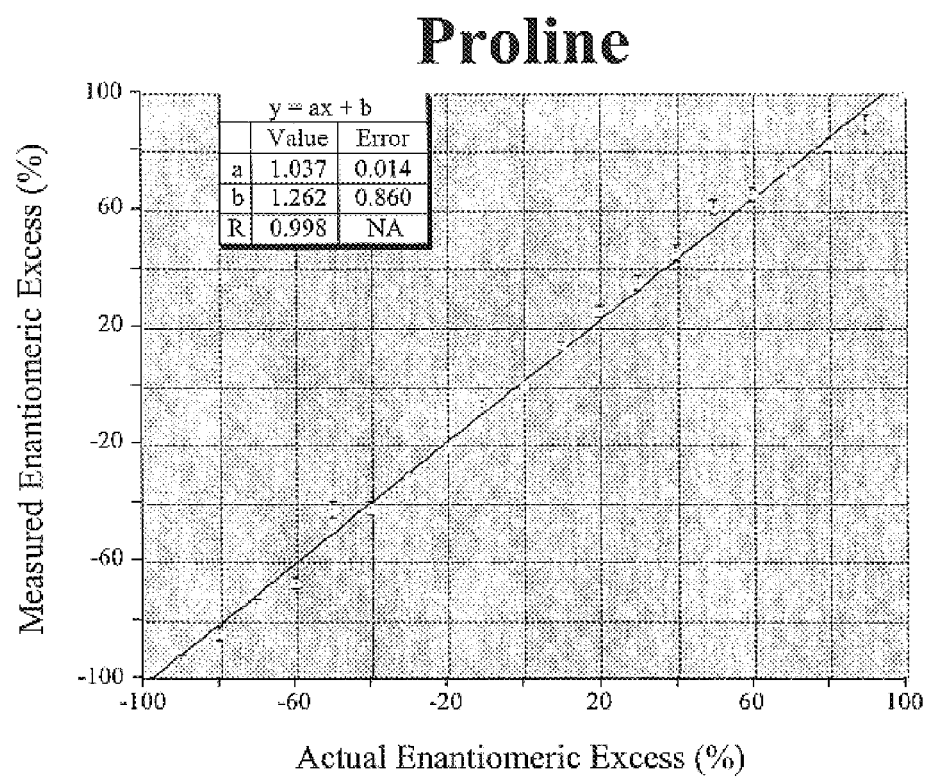
FIG. 19 depicts an exemplary graph representing Proline kinetic resolution and enantiomeric excess calculation.
Figure 20A:
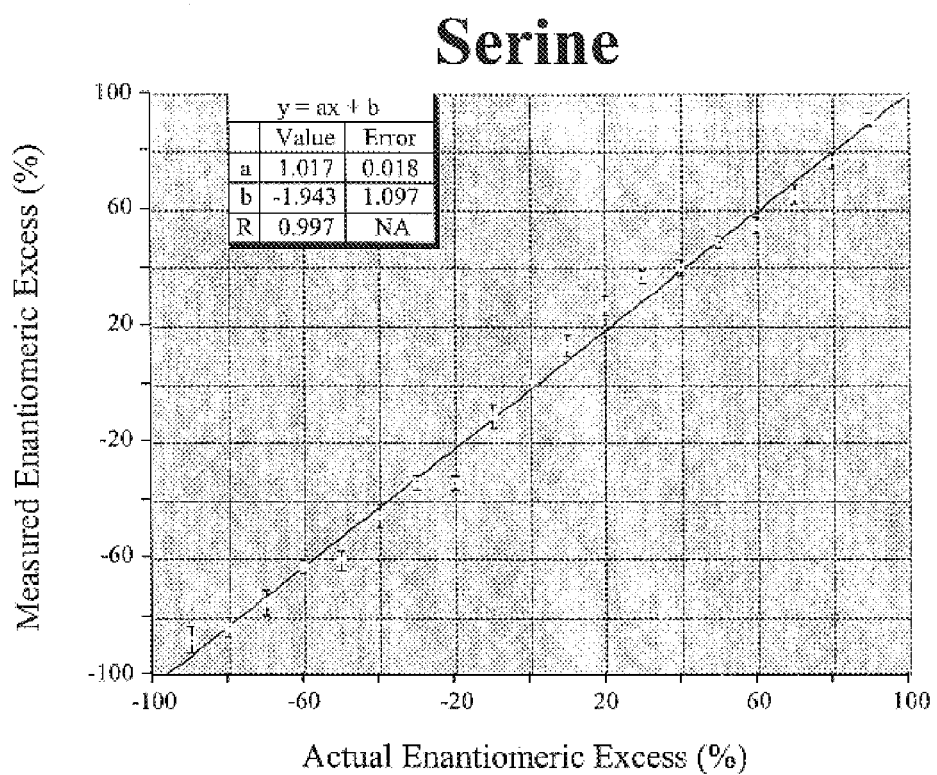
FIG. 20 depicts an exemplary graph representing Serine kinetic resolution and enantiomeric excess calculation.
Figure 21A:
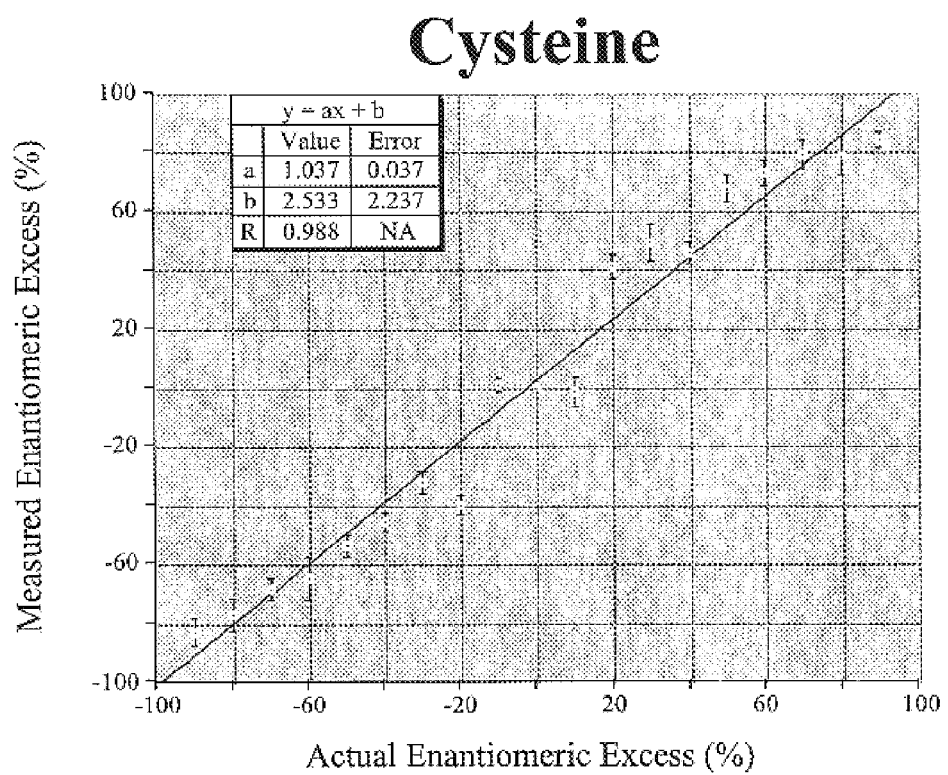
FIG. 21 depicts an exemplary graph representing Cysteine kinetic resolution and enantiomeric excess calculation.

A high throughput analysis of ee was performed by arraying 15,552 samples of proline onto a glass slide (FIG. 15) and manipulating the slides as indicated in FIG. 4. Of these samples, 15,500 were printed from 20 standard mixtures that were between 0 and 20% ee of either enantiomer. A single sample was >99% ee of the L-enantiomer. Pronounced differences in color enabled both rapid identification and determination of absolute configuration of the two samples known to be >99% ee in less than 48 hours. In this experiment, spot diameters were less than or equal to ≦140 μm, which would allow approximately 75,000 samples to be arrayed onto a 25 mm×75 mm glass slide and analyzed in a comparable amount of time.

The following experimentals more particularly describe methods for carrying out certain embodiments of the present invention, although these experimentals are not intended to limit the scope of the present invention.

Experimental Procedures and Data

Each of the reaction products numbered herein refer to structures and reaction schemes as depicted in FIGS. 7–12. See also, U.S. Pat. Nos. 5,808,044; 5,627,027; 5,453,505; 4,847,385; Ponnusamy et al. *Synthesis* 1986, 48–49; Carpino et al. *J. Org. Chem.* 1991, 56, 261 1; and Mehta et al. *Tet. Lett.* 1992, 33, 5441, the entire contents of which are hereby incorporated by reference.

General Procedures:

All reactions were performed in oven-dried glassware under an atmosphere of argon unless noted otherwise. Anhydrous 1-butanol and anhydrous dimethylformamide (DMF) were purchased from Aldrich. Anhydrous toluene was freshly distilled over Na, and anhydrous methylene chloride was distilled over calcium hydride.

1-[(4-(1-Carboxybutyl)]-2,3,3-trimethyl-3H-indolium Bromide (2)

To 5-bromovaleric acid (7.326 g, 40.5 mmol), was added 2,3,3-trimethylindolenine. The reaction was heated, with vigorous stirring, for 20 hours at 110 C. The burgundy solid was broken up and washed with six 40 mL portions of refluxing ethyl acetate, two 40 mL portions of refluxing acetone, and two 120 mL portions of refluxing acetone. Filtration of the solid and drying under vacuum afforded 7.742 g (56%) of 1 as a pale pink powder: mp 188–190 C; IR (film) 3384, 1723 cm$^{-1}$; $^1$H-NMR (400 MHz, CD$_3$OD+1 drop D$_2$O, 23 C) δ 7.90–7.87 (m, 1H); 7.78–7.75 (m, 1H); 7.67–7.63 (m, 2H); 4.56–4.52 (t, J=7.7 Hz, 2H); 2.44–2.40 (t, J=7.0 Hz, 2H); 2.04–1.96 (m, 2H); 1.80–1.72 (m, 2H); 1.61 (s, 6H) ppm; 13C-NMR (125 MHz, CD$_3$OD+1 drop D$_2$O, 23 C) δ 196.9, 175.4, 142.3, 141.4, 130.0, 129.4, 123.6, 123.5, 115.5, 115.4, 54.8, 48.0, 32.7, 27.0, 21.7 ppm; HRMS (ESI) calcd for C$_{16}$H$_{22}$N$_2$O$^+$260.1651, found 260.1639; TLC R$_f$0.12(CH$_2$Cl$_2$/methanol 3:1 v/v).

2-[(E)-2-(Carboxy-phenyl-amino)-vinyl]-1,3,3-trimethyl-3H-indolium Iodide (4)

To 1,2,3,3-tetramethyl-3H-indolium iodide (2.0020 g, 6.65 mmol), N,N'-diphenylformamidine (1.630 g, 8.31 mmol), and potassium acetate (65 mg, 0.67 mmol) was added 15 mL acetic anhydride. The mixture was heated for 5 hours at 120 C, during which time a red precipitate formed. The reaction was cooled to room temperature and filtered. The solid was collected and repeatedly recrystallized from ethanol/diethyl ether until the decanted solvent was colorless, and finally recrystallized from methanol/diethyl ether. Filtration of the solid and drying under vacuum afforded 2.171 g (73%) of 3 as a orange-yellow powder: mp 160 C (dec.); $^1$H-NMR (500 MHz, CDCl$_3$, 22 C) δ 9.19–9.16 (d, J=14.2 Hz, 1H); 7.72–7.69 (m, 2H); 7.65–7.62 (m, 1H); 7.55–7.54 (m, 2H); 7.50–7.45 (m, 4H); 5.62–5.59 (d, J=14.2 Hz, 1H); 3.86 (s, 3H); 2.11 (s, 3H); 1.83 (s, 6H) ppm; $^{13}$C-NMR (100 MHz, CDCl$_3$, 20 C) δ 170.3, 148.0, 141.9, 135.6, 131.5, 131.1, 129.5, 129.0, 128.4, 122.4, 114.2, 98.1, 77.5, 52.2, 35.8, 28.4, 24.0 ppm; IR (thin film): 1680 cm$^{-1}$; TLC R$_f$=0.81 (CH$_2$Cl$_2$/methanol 4:1 v/v).

1-[(4"-(1"-Carboxybutyl)]-1',3,3,3',3'-pentamethyl-indocarbocyanine Iodide (Cy3, 5)

To 2 (1.0040 g , 2.25 mmol), 4 (797 mg, 2.34 mmol) and potassium acetate (275 mg, 2.8 mmol) was added 10 mL anhydrous 1-butanol under argon. The mixture was heated with stirring for 1.5 hours at 100 C. Sodium iodide (6.75 g, 45 mmol) was added to the flask and the reaction was heated for 1 hour at 100 C. The reaction was cooled to room temperature and allowed to crystallize overnight. Crystals were filtered and washed with diethyl ether until the filtrate was colorless. Product was dissolved in methylene chloride (CH$_2$Cl$_2$) and concentrated in vacuo to a red solid. The crude product was purified by silica gel chromatography using a gradient elution of 30%–50% ethanolic chloroform. Appropriate fractions were combined and concentrated in vacuo to afford 915 mg (71%) of 5 as a red solid with a metallic green luster: $^1$H-NMR (400 MHz, CDCl$_3$, 23 C) δ 8.34–8.27 (dd, J=14 Hz, J =13 Hz, 1H); 7.35–7.29 (m, 4H); 7.22–7.16 (m, 2H); 7.11–7.07 (m, 2H); 6.82–6.75 (dd, J=14 Hz, J=14 Hz, 2H); 4.13 (bt, 2H); 3.71 (s, 3H); 2.47 (bt, 2H); 1.85 (m, 4H); 1.65 (s, 6H); 1.64 (s, 6H). $^{13}$C-NMR (100 MHz, CDCl$_3$, 23 C) δ 178.4, 174.3, 173.6, 150.8, 142.9, 142.1, 140.8, 140.6, 129.1, 129.0, 125.5, 125.4, 122.3, 122.1, 111.1, 111.0, 104.9, 104.8, 77.5, 49.3, 49.2, 44.6, 37.0, 32.1, 30.0, 28.4, 26.9, 23.3 ppm; IR (thin film): 3420, 1670 cm$^{-1}$; HRMS (ESI) calc'd for C$_{29}$H$_{35}$N$_2$O$_2$$^+$443.2699, found 443.2717 ; TLC R$_f$ 0.66 (CH$_2$Cl$_2$/methanol 4:1 v/v); UV λ$_{max}$ 546 nm.

1-[4"-(1"-Carboxybutyl)]-1'3,3,3',3'-pentamethyl-indodicarbocyanine Iodide (Cy5, 7)

To 2 (602.8 mg, 2.0 mmol) and potassium acetate (412.2 mg, 4.2 mmol) was added 50 mL acetic anhydride. The mixture was heated to 110 C, and malonaldehydebis (phenylimine)monohydrochloride (1.035 g, 4.0 mmol) was added in ~50 mg portions over 45 minutes. The reaction was maintained at 110 C for 1 additional hour then cooled to room temperature. Acetic acid and acetic anhydride were removed by distillation as their azeotropes with heptane, and the crude product was dried under vacuum overnight and used without further purification. To this intermediate was added 1,2,3,3-tetramethyl-3H-indolium iodide (1.5588 g, 4.4 mmol), potassium acetate (786 mg, 8.0 mmol) sodium iodide (6.00 g, 40 mmol) and 50 mL 1-butanol. The reaction was heated to 95 C for 90 minutes, then cooled slightly and the 1-butanol solvent was removed by vacuum distillation, and the remaining solid was dissolved in $CH_2Cl_2$ and washed with water. The organic phase was dried over anhydrous sodium sulfate, filtered, and concentrated in vacuo to a blue solid. The crude product was purified by flash chromatography using 8% methanolic $CH_2Cl_2$ as eluant. The appropriate fractions were combined and concentrated in vacuo to yield 223 mg (18%) of desired product as a deep blue solid with a metallic red luster: $^1$H-NMR (500 MHz, $CDCl_3$, 23 C) δ 8.04–7.97 (dt, J=13 Hz, J=13 Hz, 2H); 7.38–7.3 (m, 4H); 7.23–7.18 (m, 2H); 7.12–7.09 (m, 2H); 7.03–6.98 (t, J=12 Hz, 1H); 6.49–6.46 (d, J=14 Hz, 1H); 6.41–6.39 (d, J=13 Hz, 1H); 4.10–4.07 (t, J=7 Hz, 2H); 3.69 (s, 3H); 2.57–2.55 (t, J=7 Hz, 2H); 1.85–1.81 (m, 4H); 1.72 (s, 12H). $^{13}$C-NMR (125 MHz, $CDCl_3$, 23 C) δ 176.4, 173.2, 172.7, 153.5, 153.4, 142.8, 142.0, 141.2, 141.0, 128.8, 128.7, 126.6, 125.2, 125.1, 122.3, 122.2, 110.8, 110.6, 104.2, 104.0, 77.5, 49.6, 49.5, 44.4, 34.6, 32.6, 30.0, 28.5, 28.4, 26.8, 22.6 ppm; IR (thin film) 3415, 1649 cm$^{-1}$. HRMS (ESI) calc'd for $C_{31}H_{37}N_2O_2{}^+$469.2855, found 469.2837 ; TLC $R_f$0.72 ($CH_2Cl_2$/methanol 4:1 v/v); UV $λ_{max}$ 640 nm.

Cy3-(R)-phenylalanine Tert-butyl Ester Conjugate (8)

To an oven-dried, septaed 10 mL round-bottom flask, cooled under an argon atmosphere and charged with 5 (112.5 mg, 0.19 mmol), (R)-phenylalanine tert-butyl ester hydrochloride (63.7 mg, 0.25 mmol), 1-[3-(dimethylamino) propyl]-3-ethylcarbodiimide hydrochloride (EDC.HCl, 74.0 mg, 0.39 mmol) and 1-hydroxybenzotriazole hydrate (HOBt.$H_2O$, 38.4 mg, 0.25 mmol) was added 1 mL anhydrous N,N-dimethylformamide (DMF) under argon. While stirring under argon, diisopropylethylamine (DIPEA, 135 μL, 0.77 mmol) was added, and the reaction was left to stir for 20 hours at room temperature and under argon. The crude reaction was poured into 40 mL 0.5 M HCl and extracted to completion with $CH_2Cl_2$. Combined $CH_2Cl_2$ extractions were washed with 40 mL water, dried over anhydrous magnesium sulfate, filtered, then concentrated in vacuo. The crude product was purified by silica gel chromatography using a gradient elution of $CH_2Cl_2$:acetone:methanol (90:8:2 to 87:8:5). Appropriate fractions were combined and concentrated in vacuo to afford 119 mg (81%) of 8 as a red solid.

Cy3-(R)-phenylalanine Conjugate (9) by Solution Phase Synthesis

To an oven-dried, septaed 10 mL round-bottom flask, cooled under an argon atmosphere and charged with 8 (87 mg, 0.11 mmol) was added 230 μL $CH_2Cl_2$ under argon. While stirring under argon 45 μL triethylsilane then 130 μL trifluoroacetic acid were added and reaction was stirred 5 hours at room temperature. The crude reaction was concentrated in vacuo then purified by silica gel chromatography using a gradient elution of 15%–40% ethanolic $CH_2Cl_2$. Appropriate fractions were combined and concentrated in vacuo to afford 43.7 mg (62%) of 9 as a red solid. HRMS (ESI) calc'd for $C_{38}H_{44}N_3O_3$ (M+): 590.3382, found 590.3383.

Cy3-(R)-phenylalanine Conjugate (9) by Solid Phase Synthesis

TGT trityl alcohol resin (NovaBiochem, La Jolla, Calif.; 0.28 mmol/g, 250 mg, 70 μmol) was washed six times with DMF, six times with tetrahydrofuran (THF), six times with $CH_2Cl_2$, then dried under vacuum overnight. Beads were transferred to a 10 mL Bio-Rad polypropylene tube, and purged with argon. Under argon was added 2 mL freshly distilled toluene and acetyl chloride (350 μL, 4.9 mmol), the tube was immersed in an oil bath, and reaction was maintained for 4 hours at 65° C. Beads were washed under argon four times with freshly distilled toluene, eight times with freshly distilled $CH_2Cl_2$, then six times with anhydrous DMF. To the beads were added (R)-N-Fmoc-phenylalanine (54 mg, 0.14 mmol), followed by 2 mL anhydrous DMF, then freshly distilled DIPEA (25 μL, 0.14 mmol) under argon. The tube was capped, and placed on an orbital stirrer overnight. Beads were washed six times with DMF, six times with THF, six times with $CH_2Cl_2$, then four times with DMF. To the beads was then added 2 mL 20% piperidine in DMF (v/v), and tube was placed on an orbital stirrer for 10 hours. Beads were washed six times with DMF, six times with THF, six times with $CH_2Cl_2$, then six times with DMF. To the beads were then added 5 (81.5 mg, 0.14 mmol), EDC.HCl (33.5 mg, 0.18 mmol), HOBt.$H_2O$ (21.4 mg, 0.14 mmol), 1.5 mL DMF, and DIPEA (55 μL, 0.32 mmol). Tube was placed on an orbital stirrer for 36 hours, then washed twice with $CH_2Cl_2$ to recover excess 5. Beads were then washed six times with DMF, six times with THF, and six times with $CH_2Cl_2$. To the beads was then added 4 mL 2% trifluoroacetic acid in $CH_2Cl_2$ (v/v), and the reaction tube was placed on an orbital stirrer for 1 hour. Elution with $CH_2Cl_2$ and concentration in vacuo afforded 9 as a red solid. Prior to further use, product was further purified in the following manner as needed. A solution of 9 in $CH_2Cl_2$ was adsorbed on a reversed-phase $C_{18}$ TLC plate, and developed with 80% aqueous ethanol. Product band was excised, eluted with methanol, and concentrated in vacuo. Product was redissolved in 5% methanolic $CH_2Cl_2$, passed through a plug of washed and dried sand to filter off methanol-soluble TLC plate particles, and concentrated in vacuo to afford analytically pure 9 as a red solid.

Cy3-(S)-phenylalanine Tert-butyl Ester Conjugate (10)

To an oven-dried, septaed 25 mL round-bottom flask, cooled under an argon atmosphere and charged with 5 (99.0 mg, 0.17 mmol), (S)-phenylalanine tert-butyl ester hydrochloride (57.0 mg, 0.22 mmol), EDC.HCl (65.2 mg, 0.34 mmol) and HOBt.$H_2O$ (33.8 mg, 0.22 mmol) was added 1 mL anhydrous DMF under argon. While stirring under argon, DIPEA (118 μL, 0.68 mmol) was added, and the reaction was stirred for 18 hours at room temperature. The crude reaction was poured into 40 mL 0.5 M HCl and extracted to completion with $CH_2Cl_2$. Combined $CH_2Cl_2$ extractions were washed with 40 mL water, dried over anhydrous magnesium sulfate, filtered, and concentrated in vacuo. The crude product was purified by silica gel chromatography using a gradient elution of $CH_2Cl_2$: acetone:methanol (90:8:2 to 87:8:5). Appropriate fractions were combined and concentrated in vacuo to afford 109 mg (83%) of 10 as a red solid.

Cy3-(S)-phenylalanine Conjugate (11)

To an oven-dried, septaed 10 mL round-bottom flask, cooled under an argon atmosphere and charged with 10 (42.2 mg, 0.05 mmol) was added 112 μL $CH_2Cl_2$ under argon. While stirring under argon, 22 μL triethylsilane then 63 μL trifluoroacetic acid were added and the reaction was stirred for 5 hours at room temperature. The crude reaction was concentrated in vacuo then purified by silica gel chromatography using a gradient elution of 15%–40% ethanolic $CH_2C_2$. Appropriate fractions were combined and concentrated in vacuo to afford 11 as a red solid.

Cy3-(R)-proline Tert-butyl Ester Conjugate (12)

To an oven-dried, septaed 25 mL round-bottom flask, cooled under an argon atmosphere and charged with 5 (95.8 mg, 0.16 mmol), (R)-proline tert-butyl ester hydrochloride (44.4 mg, 0.21 mmol), EDC.HCl (63.1 mg, 0.33 mmol) and HOBt.H$_2$O (32.7 mg, 0.21 mmol) was added 1 mL anhydrous DMF under argon. While stirring under argon, DIPEA (115 µL, 0.66 mmol) was added and the reaction was stirred for 18 hours at room temperature. The crude reaction was poured into 40 mL 0.5 M HCl and extracted to completion with CH$_2$Cl$_2$. The combined CH$_2$Cl$_2$ extractions were washed with 40 mL water, dried over anhydrous magnesium sulfate, filtered, and concentrated in vacuo to afford 12 as a red solid.

Cy3-(S)-proline Tert-butyl Ester Conjugate (13)

To an oven-dried, septaed 25 mL round-bottom flask, cooled under an argon atmosphere and charged with 5 (98.8 mg, 0.17 mmol), (S)-proline tert-butyl ester hydrochloride (45.8 mg, 0.22 mmol), EDC.HCl (65.0 mg, 0.34 mmol) and HOBt.H$_2$O (33.8 mg, 0.22 mmol) was added 1 mL anhydrous DMF under argon. While stirring under argon, DIPEA (118 µL, 0.68 mmol) was added, and the reaction was stirred for 18 hours at room temperature. The crude reaction was poured into 40 mL 0.5 M HCl and extracted to completion with CH$_2$Cl$_2$. The combined CH$_2$Cl$_2$ extractions were washed with 40 mL water, dried over anhydrous magnesium sulfate, filtered, then concentrated in vacuo. The crude product was purified by silica gel chromatography using a gradient elution of CH$_2$Cl$_2$:acetone:methanol (90:8:2 to 87:8:5). Appropriate fractions were combined and concentrated in vacuo to afford 104.7 mg (85%) of 13 as a red solid.

Cy5-(S)-phenylalanine Tert-butyl Ester Conjugate (14)

To an oven-dried, septaed 25 mL round-bottom flask, cooled under an argon atmosphere and charged with 7 (89.6 mg, 0.15 mmol), (S)-phenylalanine tert-butyl ester hydrochloride (49.3 mg, 0.19 numol), EDC.HCl (56.4 mg, 0.29 mmol) and HOBt.H$_2$O (29.3 mg, 0.19 mmol) was added 1 mL anhydrous DMF under argon. While stirring under argon, DIPEA (118 µL, 0.68 mmol) was added, and the reaction was stirred for 18 hours at room temperature. The crude reaction was poured into 40 mL 0.5 M HCl and extracted to completion with CH$_2$C$_{12}$. Combined CH$_2$Cl$_2$ extractions were washed with 40 mL water, dried over anhydrous magnesium sulfate, filtered, and concentrated in vacuo. The crude product was purified by silica gel chromatography using CH$_2$Cl$_2$:ethanol:acetone (72:18:10) as eluant. Appropriate fractions were combined and concentrated in vacuo to afford 70.6 mg (60%) of 14 as a blue solid.

Cy5-(S)-phenylalanine Conjugate (15)

To an oven-dried, septaed 10 mL round-bottom flask, cooled under an argon atmosphere and charged with 14 (44.6 mg, 0.05 mmol) was added 114 µL CH$_2$Cl$_2$ under argon. While stirring under argon, 22 µL triethylsilane then 65 µL trifluoroacetic acid were added and the reaction was stirred 5 hours at room temperature. The crude reaction was concentrated in vacuo to afford 15 as a blue solid.

Cy3-(R)-proline Conjugate (16)

TGT trityl alcohol resin (NovaBiochem, 0.28 mmol/g, 250 mg, 70 µmol) was washed six times with dimethylformamide (DMF), six times with tetrahydrofuran (THF), six times with CH$_2$Cl$_2$, then dried under vacuum overnight. The beads were transferred to a 10 mL Bio-Rad polypropylene tube, and purged with argon. Under argon was added 2 mL anhydrous toluene and acetyl chloride (350 µL, 4.9 mmol), the tube was immersed in an oil bath, and the reaction was maintained for 4 hours at 65 C. The beads were washed under argon four times with anhydrous toluene, eight times with anhydrous CH$_2$Cl$_2$, then six times with anhydrous DMF. To the beads were added (R)-N-Fmoc-proline (47 mg, 0.14 mmol), 2 mL anhydrous DMF, and freshly distilled diisopropylethylamine (DIPEA, 25 µL, 0.14 mmol) under argon. The tube was capped, then placed on an orbital stirrer overnight. Beads were washed six times with DMF, six times with THF, six times with CH$_2$Cl$_2$, then four times with DMF. To the beads was then added 2 mL 20% piperidine in DMF (v/v), and the tube was placed on an orbital stirrer for 10 hours. Beads were washed six times with DMF, six times with THF, six times with CH$_2$Cl$_2$, then six times with DMF. To the beads were then added 5 (81.5 mg, 0.14 mmol), 1-(3-dimethylaminopropyl)-3-ethylcarbodiimide hydrochloride (EDC.HCl, 33.5 mg, 0.18 mmol), 1-hydroxybenzotriazole hydrate (HOBt.H$_2$O, 21.4 mg, 0.14 mmol), 1.5 mL DMF, and DIPEA (55 µL, 0.32 mmol). The tube was placed on an orbital stirrer for 36 hours, then washed twice with CH$_2$Cl$_2$ to recover excess 5. Beads were then washed six times with DMF, six times with THF, and six times with CH$_2$Cl$_2$. To the beads was then added 4 mL 2% trifluoroacetic acid in CH$_2$Cl$_2$ (v/v), and the reaction tube was placed on an orbital stirrer for 1 hour. Elution with CH$_2$Cl$_2$ and concentration in vacuo afforded 16 as a red solid. Prior to further use as needed, the product was further purified in the following manner. A solution of 16 in CH$_2$Cl$_2$ was adsorbed on a reversed-phase C$_{18}$ TLC plate, and developed with 80% aqueous ethanol. The product band was excised, eluted with methanol, and concentrated in vacuo. The product was redissolved in 5% methanolic CH$_2$Cl$_2$, passed through a plug of washed and dried sand, and concentrated in vacuo to afford analytically pure 16 as a red solid:. $^1$H-NMR (500 MHz, CDCl$_3$, 23 C) δ 8.41–8.35 (t, J=13 Hz, 1H); 7.74–7.71 (d, J=13 Hz, 1H); 7.47–7.32 (m, 3H); 7.24–7.21 (m, 4H); 7.15–7.14 (d, J=8 Hz, 1H); 7.10–7.09 (d, J=8 Hz, 1H); 4.33–4.30 (m, 2H); 4.04–3.98 (m, 1H); 3.89 (s, 3H); 3.75–3.71 (m, 1H); 3.61–3.55 (m, 1H); 2.78–2.73 (m, 1H); 2.47–2.23 (m, 3H); 2.07–2.03 (m, 1H); 1.90–1.83 (m, 1H); 1.83–1.76 (m, 1H); 1.70 (s, 6H); 1.69 (s, 6H); 1.58–1.54 (m, 3H). FTIR (film) 3386, 1682 cm$^{-1}$. HRMS (FAB) calc'd for C$_{34}$H$_{41}$N$_3$NaO$_3$$^+$(M+Na)$^+$: 562.3046, found 562.3054.

Cy3-(R)-alanine Conjugate (17)

TGT trityl alcohol resin (0.28 mmol/g, 100 mg, 28 µmol) was added to a 10 mL Bio-Rad polypropylene tube, washed six times with THF, then six times with CH$_2$Cl$_2$. The tube was purged with argon and the beads were washed four times with freshly distilled toluene. To the resin was then added 2 mL freshly distilled toluene and 350 µL acetyl chloride, then the tube was immersed in an oil bath, and maintained for 3 hours at 65° C. Beads were washed under argon four times with freshly distilled toluene, five times with freshly distilled CH$_2$Cl$_2$, and six times with anhydrous DMF. To the beads were then added (R)-N-Fmoc-alanine (34.9 mg, 0.11 mmol), 2 mL anhydrous DMF, and freshly distilled DIPEA (19.5 µL, 0.11 mmol) under argon. The tube was capped, then placed on an orbital stirrer for 4 hours. Beads were washed six times with DMF, six times with THF, twelve times with CH$_2$Cl$_2$, then six times with DMF. To the beads was then added 3 mL 20% piperidine in DMF (v/v), and the tube was placed on an orbital stirrer for 10 hours. Beads were washed six times with DMF, six times with THF, six times with CH$_2$Cl$_2$, and six times with DMF. To the beads were then added 5 (32.6 mg, 56 µmol), benzotriazol-1-yloxytripyrrolidinophophonium hexafluorophosphate (PyBOP, 32 mg, 62 µmol), and 2 mL DMF. The tube was placed on an orbital stirrer for 8 hours, then the beads were washed four times with 25% methanolic CH$_2$Cl$_2$, six times with DMF, six times with THF, four times with 25% methanolic $CH_2Cl_2$, four times with $CH_2Cl_2$, twice with methanol, and six times with $CH_2Cl_2$. To the beads were then added 1.5 mL 10% triethylsilane in $CH_2Cl_2$ (v/v) and 1.5 mL 2% trifluoroacetic acid in $CH_2Cl_2$ (v/v), and the reaction tube was placed on an orbital stirrer for 1.5 hours. Elution with 25% methanolic $CH_2Cl_2$ and concentration in vacuo afforded 17 as a red solid. A solution of 17 in methanol was adsorbed on a reversed-phase $C_{18}$ TLC plate, and developed with 80% aqueous ethanol. The product band was excised, eluted with methanol, and concentrated in vacuo. The product was redissolved in 5% methanolic $CH_2Cl_2$, passed through a plug of washed and dried sand to filter off methanol-soluble TLC plate particles, and concentrated in vacuo to afford 7.0 mg (39%) of analytically pure 17 as a red solid.

Cy3-(R)-valine Conjugate (18)

TGT trityl alcohol resin (0.28 mmol/g, 100 mg, 28 µmol) was added to a 10 mL Bio-Rad polypropylene tube, washed six times with THF, then six times with $CH_2Cl_2$. The tube was purged with argon and the beads were washed four times with freshly distilled toluene. To the resin was then added 2 mL freshly distilled toluene and 350 µL acetyl chloride, then the tube was immersed in an oil bath and maintained for 3 hours at 65° C. Beads were washed under argon four times with freshly distilled toluene, five times with freshly distilled $CH_2Cl_2$, then six times with anhydrous DMF. To the beads were then added (R)-N-Fmoc-valine (38 mg, 0.11 mmol), 2 mL anhydrous DMF, and freshly distilled DIPEA (19.5 µL, 0.11 mmol) under argon. The tube was capped, then placed on an orbital stirrer for 4 hours. Beads were washed six times with DMF, six times with THF, twelve times with $CH_2Cl_2$, then six times with DMF. To the beads was then added 3 mL 20% piperidine in DMF (v/v), and the tube was placed on an orbital stirrer for 10 hours. Beads were washed six times with DMF, six times with THF, six times with $CH_2Cl_2$, then six times with DMF. To the beads were then added 5 (32.6 mg, 56 µmol), PyBOP (32 mg, 62 µmol), and 2 mL DMF. The tube was placed on an orbital stirrer for 8 hours, then the beads were washed four times with 25% methanolic $CH_2Cl_2$, six times with DMF, six times with THF, four times with 25% methanolic $CH_2Cl_2$, four times with $CH_2Cl_2$, twice with methanol, and six times with $CH_2C_2$. To the beads were then added 1.5 mL 10% triethylsilane in $CH_2Cl_2$ (v/v) and 1.5 mL 2% trifluoroacetic acid in $CH_2Cl_2$ (v/v), and the reaction tube was placed on an orbital stirrer for 1.5 hours. Elution with 25% methanolic $CH_2Cl_2$ and concentration in vacuo afforded 18 as a red solid. A solution of 18 in methanol was adsorbed on a reversed-phase $C_{18}$ TLC plate, and developed with 80% aqueous ethanol. The product band was excised, eluted with methanol, and concentrated in vacuo. The product was redissolved in 5% methanolic $CH_2Cl_2$, passed through a plug of washed and dried sand to filter off methanol-soluble TLC plate particles, and concentrated in vacuo to afford 12.8 mg (68%) of analytically pure 18 as a red solid.

Cy3-(R)-leucine (19)

TGT trityl alcohol resin (0.28 mmol/g, 100 mg, 28 µmol) was added to a 10 mL Bio-Rad polypropylene tube, washed six times with DMF, six times with THF, then six times with $CH_2Cl_2$. The tube was purged with argon and the beads were washed six times with freshly distilled toluene. To the resin were then added 2 mL freshly distilled toluene and 350 µL acetyl chloride, then the tube was immersed in an oil bath and maintained for 3 hours at 65° C. Beads were washed under argon four times with freshly distilled toluene, five times with freshly distilled $CH_2Cl_2$, then six times with anhydrous DMF. To the beads were then added (R)-N-Fmoc-leucine (39.6 mg, 0.11 mmol), 2 mL anhydrous DMF, and freshly distilled DIPEA (20 µL, 0.11 mmol) under argon. The tube was capped, then placed on an orbital stirrer for 4 hours. Beads were washed six times with DMF, six times with THF, twelve times with $CH_2Cl_2$, then six times with DMF. To the beads was then added 3 mL 20% piperidine in DMF (v/v), and tube was placed on an orbital stirrer for 10 hours. Beads were washed six times with DMF, six times with TBF, six times with $CH_2Cl_2$, then six times with DMF. To the beads were then added 5 (32 mg, 56 µmol), PyBOP (32 mg, 62 µmol), and 2 mL DMF. The tube was placed on an orbital stirrer for 24 hours, then the beads were washed six times with DMF, six times with THF, four times with 25% methanolic $CH_2Cl_2$, four times with methanol, eight times with 25% methanolic $CH_2Cl_2$, and six times with $CH_2Cl_2$. To the beads were then added 1.5 mL 10% triethylsilane in $CH_2Cl_2$ (v/v) and 1.5 mL 2% trifluoroacetic acid in $CH_2Cl_2$ (v/v), and the reaction tube was placed on an orbital stirrer for 1.5 hours. Elution with 25% methanolic $CH_2Cl_2$ and concentration in vacuo afforded 19 as a red solid. A solution of 19 in methanol was adsorbed on a reversed-phase $C_{18}$ TLC plate, and developed with 80% aqueous ethanol. The product band was excised, eluted with methanol, and concentrated in vacuo. The product was redissolved in 5% methanolic $CH_2Cl_2$, passed through a plug of washed and dried sand to filter off methanol-soluble TLC plate particles, and concentrated in vacuo to afford 8.4 mg (44%) of analytically pure 19 as a red solid.

Cy3-(R)-β-cyclohexylalanine Conjugate (20)

TGT trityl alcohol resin (0.28 mmol/g, 100 mg, 28 µmol) was added to a 10 mL Bio-Rad polypropylene tube, and washed six times with DMF, six times with THF then six times with $CH_2Cl_2$. The tube was purged with argon and the beads were washed six times with freshly distilled toluene. To the resin were added 2 mL freshly distilled toluene and 350 µL acetyl chloride, then the tube was immersed in an oil bath and maintained for 3 hours at 65° C. Beads were washed under argon four times with freshly distilled toluene, five times with freshly distilled $CH_2Cl_2$, then six times with anhydrous DMF. To the beads were then added (R)-N-Fmoc-β-cyclohexylalanine (44.1 mg, 0.11 mmol), 2 mL anhydrous DMF, and freshly distilled DIPEA (20 µL, 0.11 mmol) under argon. The tube was capped, then placed on an orbital stirrer for 4 hours. Beads were washed six times with DMF, six times with THF, twelve times with $CH_2Cl_2$, then six times with DMF. To the beads was then added 3 mL 20% piperidine in DMF (v/v), and the tube was placed on an orbital stirrer for 10 hours. Beads were washed six times with DMF, six times with THEF, six times with $CH_2Cl_2$, then six times with DMF. To the beads were then added 5 (32 mg, 56 µmol), PyBOP (32 mg, 62 µmol), and 2 mL DMF. The tube was placed on an orbital stirrer for 24 hours, then beads were washed six times with DMF, six times with THF, four times with 25% methanolic $CH_2Cl_2$, four times with methanol, eight times with 25% methanolic $CH_2Cl_2$, and six times with $CH_2Cl_2$. To the beads were then added 1.5 mL 10% triethylsilane in $CH_2Cl_2$ (v/v) and 1.5 mL 2% trifluoroacetic acid in $CH_2Cl_2$ (v/v), and the reaction tube was placed on an orbital stirrer for 1.5 hours. Elution with 25% methanolic $CH_2Cl_2$ and concentration in vacuo afforded 20 as a red solid. A solution of 20 in methanol was adsorbed on a reversed-phase $C_{18}$ TLC plate, and developed with 80% aqueous ethanol. The product band was excised, eluted with methanol, and concentrated in vacuo. The product was redissolved in 5% methanolic $CH_2Cl_2$, passed through a plug of washed and dried sand to filter off methanol-soluble TLC plate particles, and concentrated in vacuo to afford 6.5 mg (32%) of analytically pure 20 as a red solid.

Cy5-(S)-proline Conjugate (21)

TGT trityl alcohol resin (0.28 mmol/g, 127 mg, 36 μmol) was added to a 10 mL Bio-Rad polypropylene tube, and purged with argon. Under argon, the beads were washed eight times with anhydrous toluene. To the resin was then added 2 mL anhydrous toluene and 350 μL acetyl chloride, then the tube was immersed in an oil bath, and maintained for 3 hours at 65 C. Beads were washed under argon six times with anhydrous toluene, twelve times with anhydrous $CH_2Cl_2$, then eight times with anhydrous DMF. To the beads were then added (S)-N-Fmoc-proline (47 mg, 0.14 mmol), followed by 2 mL anhydrous DMF, and freshly distilled DIPEA (25 μL, 0.14 mmol) under argon. The tube was capped, then placed on an orbital stirrer for 4 hours. Beads were washed six times with DMF, six times with THF, twelve times with $CH_2Cl_2$, then six times with DMF. To the beads was then added 3 mL 20% piperidine in DMF (v/v), and tube was placed on orbital stirrer for 8 hours. Beads were washed six times with DMF, six times with THF, six times with $CH_2Cl_2$, and six times with DMF. To the beads were then added 7 (44 mg, 72 μmol), benzotriazolyloxytripyrrolidinophosphonium hexafluorophosphate (PyBOP, 41 mg, 79 μmol), and 2 mL DMF. The tube was placed on an orbital stirrer for 8 hours, then the beads were washed four times with 25% methanolic $CH_2Cl_2$, six times with DMF, six times with THF, four times with 25% methanolic $CH_2Cl_2$, twice with methanol, and six times with $CH_2Cl_2$. To the beads were then added 1.5 mL 10% triethylsilane in $CH_2Cl_2$ (v/v) and 1.5 mL 2% trifluoroacetic acid in $CH_2Cl_2$ (v/v), and the reaction tube was placed on an orbital stirrer for 1.5 hours. Elution with 25% methanolic $CH_2Cl_2$ and concentration in vacuo afforded 21 as a blue solid. Prior to further use, the product was further purified in the following manner as needed. A solution of 21 in $CH_2Cl_2$ was adsorbed on a reversed-phase $C_{18}$ TLC plate, and developed with 80% aqueous ethanol. The product band was excised, eluted with methanol, and concentrated in vacuo. The product was redissolved in 5% methanolic $CH_2Cl_2$, passed through a plug of washed and dried sand, and concentrated in vacuo to afford 7.4 mg (10.7 μmol, 30%) of analytically pure 21 as a blue solid: $^1$H-NMR (500 MHz, $CDCl_3$, 23 C) δ 7.77–7.72 (t, J=13 Hz, 1H); 7.69–7.64 (t, J=13 Hz, 1H); 7.42–7.39 (t, J=8 Hz, 1H); 7.36–7.30 (m, 3H); 7.25–7.24 (m, 2H); 7.17–7.13 (m, 2H); 7.00–6.93 (m, 2H); 6.21–6.19 (d, J=13 Hz, 1H); 4.32–4.24 (m, 2H); 4.21–4.16 (m, 1H); 3.75–3.70 (m, 1H); 3.59–3.53 (m, 1H); 3.50 (s, 3H); 2.77–2.71 (m, 1H); 2.44–2.15 (m, 5H); 2.10–2.02 (m, 1H); 1.93–1.88 (m, 1H); 1.85–1.76 (m, 2H); 1.66 (s, 12H). FTIR (film) 3414, 1730, 1633 $cm^{-1}$. HRMS (ESI) calc'd for $C_{36}H_{44}N_3O_3{}^+(M^+)$: 566.3382, found 566.3406.

Cy5-(S)-alanine Conjugate (22)

TGT trityl alcohol resin (0.28 mmol/g, 100 mg, 28 μmol) was added to a 10 mL Bio-Rad polypropylene tube, and washed six times with DMF, six times with THF then six times with $CH_2Cl_2$. The tube was purged with argon and the beads were washed six times with freshly distilled toluene. To the resin were added 2 mL freshly distilled toluene and 350 μL acetyl chloride, then the tube was immersed in an oil bath and maintained for 3 hours at 65° C. Beads were washed under argon four times with freshly distilled toluene, five times with freshly distilled $CH_2Cl_2$, then six times with anhydrous DMF. To the beads were then added (S)-N-Fmoc-alanine (34.9 mg, 0.11 mmol), 2 mL anhydrous DMF, and freshly distilled DIPEA (20 μL, 0.11 mmol) under argon. The tube was capped, then placed on an orbital stirrer for 4 hours. Beads were washed six times with DMF, six times with THF, twelve times with $CH_2Cl_2$, then six times with DMF. To the beads was then added 3 mL 20% piperidine in DMF (v/v), and the tube was placed on an orbital stirrer for 10 hours. Beads were washed six times with DMF, six times with THF, six times with $CH_2Cl_2$, then six times with DMF. To the beads were then added 7 (33.4 mg, 56 μmol), PyBOP (32 mg, 62 μmol), and 2 mL DMF. The tube was placed on an orbital stirrer for 24 hours, then the beads were washed six times with DMF, six times with THF, four times with 25% methanolic $CH_2Cl_2$, four times with methanol, eight times with 25% methanolic $CH_2Cl_2$, and six times with $CH_2Cl_2$. To the beads were then added 1.5 mL 10% triethylsilane in $CH_2Cl_2$ (v/v) and 1.5 mL 2% trifluoroacetic acid in $CH_2Cl_2$ (v/v), and the reaction tube was placed on an orbital stirrer for 1.5 hours. Elution with 25% methanolic $CH_2Cl_2$ and concentration in vacuo afforded 22 as a blue solid. A solution of 2 in methanol was adsorbed on a reversed-phase $C_{18}$ TLC plate and developed with 80% aqueous ethanol. The product band was excised, eluted with methanol, and concentrated in vacuo. The product was redissolved in 5% methanolic $CH_2Cl_2$, passed through a plug of washed and dried sand to filter off methanol-soluble TLC plate particles, and concentrated in vacuo to afford 3.1 mg (17%) of analytically pure 22 as a blue solid.

Cy5-(S)-valine Conjugate (23)

TGT trityl alcohol resin (0.28 mmol/g, 100 mg, 28 μmol) was added to a 10 mL Bio-Rad polypropylene tube, and washed six times with DMF, six times with THF then six times with $CH_2Cl_2$. The tube was purged with argon and the beads were washed six times with freshly distilled toluene. To the resin were added 2 mL freshly distilled toluene and 350 μL acetyl chloride, then the tube was immersed in an oil bath and maintained for 3 hours at 65° C. The beads were washed under argon four times with freshly distilled toluene, five times with freshly distilled $CH_2Cl_2$, then six times with anhydrous DMF. To the beads were then added (S)-N-Fmoc-valine (38 mg, 0.11 mmol), 2 mL anhydrous DMF, and freshly distilled DIPEA (20 μL, 0.11 mmol) under argon. The tube was capped, then placed on an orbital stirrer for 4 hours. The beads were washed six times with DMF, six times with THF, twelve times with $CH_2Cl_2$, then six times with DMF. To the beads was then added 3 mL 20% piperidine in DMF (v/v), and the tube was placed on an orbital stirrer for 10 hours. The beads were washed six times with DMF, six times with THF, six times with $CH_2Cl_2$, then six times with DMF. To the beads were then added 7 (33.4 mg, 56 μmol), PyBOP (32 mg, 62 μmol), and 2 mL DMF. The tube was placed on an orbital stirrer for 24 hours, then beads were washed six times with DMF, six times with THF, four times with 25% methanolic $CH_2Cl_2$, four times with methanol, eight times with 25% methanolic $CH_2Cl_2$, and six times with $CH_2Cl_2$. To the beads were then added 1.5 mL 10% triethylsilane in $CH_2Cl_2$ (v/v) and 1.5 mL 2% trifluoroacetic acid in $CH_2Cl_2$ (v/v), and the reaction tube was placed on an orbital stirrer for 1.5 hours. Elution with 25% methanolic $CH_2Cl_2$ and concentration in vacuo afforded 23 as a blue solid. A solution of 23 in methanol was adsorbed on a reversed-phase $C_{18}$ TLC plate, and developed with 80% aqueous ethanol. The product band was excised, eluted with methanol, and concentrated in vacuo. The product was redissolved in 5% methanolic $CH_2Cl_2$, passed through a plug of washed and dried sand to filter off methanol-soluble TLC plate particles, and concentrated in vacuo to afford 1.3 mg (7%) of analytically pure 23 as a blue solid.

(R)-2-tert-Butoxycarbonylamino-3,3-dimethyl-butyric Acid (24h)

To an oven-dried 50 ml round-bottom flask fitted with a septaed condenser, cooled under an argon atmosphere, and charged with (R)-tert-leucine (245.7 mg, 1.87 mmol) and di-tert-butyl dicarbonate (818 mg, 3.75 mmol) was added 3.6 mL anhydrous methanol followed by 400 μL of freshly distilled triethylamine. The reaction was heated with stirring to 50° C. for 30 minutes after all tert-leucine had disappeared. The reaction was concentrated in vacuo, 20 mL ice-cold dilute HCl (pH -2) was added, and the reaction was stirred for 10 minutes. The mixture was immediately extracted three times with ethyl acetate, and the combined organic extracts were dried over anhydrous magnesium sulfate, filtered, and concentrated in vacuo to afford 24h as a white solid.

(R)-tert-Butoxycarbonylamino-phenyl-acetic Acid (24j)

To an oven-dried 50 ml round-bottom flask fitted with a septaed condenser, cooled under an argon atmosphere, and charged with (R)-phenylglycine (756 mg, 5.0 mmol) and di-tert-butyl dicarbonate (2.18 g, 10.0 mmol) was added 7.0 mL anhydrous methanol followed by 3.0 mL of freshly distilled triethylamine. The reaction was heated with stirring to 50° C. for 30 minutes after all tert-leucine had disappeared. The reaction was concentrated in vacuo, 20 mL ice-cold dilute HCl (pH ~2) was added, and the reaction was stirred for 10 minutes. The mixture was immediately extracted three times with ethyl acetate, and the combined organic extracts were dried over anyhydrous magnesium sulfate, filtered, and concentrated in vacuo. Crytallization from petroleum ether afforded 1.20 g (96%) of 24j as white crystals.

(S)-tert-Butoxycarbonylamino-phenyl-acetic Acid (24k)

To an oven-dried 50 ml round-bottom flask fitted with a septaed condenser, cooled under an argon atmosphere, and charged with (S)-phenylglycine (378 mg, 2.5 nmmol) and di-tert-butyl dicarbonate (1.09 g, 5.0 mmol) was added 3.5 mL anhydrous methanol followed by 1.5 mL of freshly distilled triethylamine. The reaction was heated with stirring to 50° C. for 30 minutes after all tert-leucine had disappeared. The reaction was concentrated in vacuo, 20 mL ice-cold dilute HCl (pH ~2) was added, and the reaction was stirred for 10 minutes. The mixture was immediately extracted three times with ethyl acetate, and the combined organic extracts were dried over anhydrous magnesium sulfate, filtered, and concentrated in vacuo. Crystallization from petroleum ether afforded 557 mg (89%) of 24k as white crystals.

Fluorocarbonylmethyl-carbamic Acid tert-butyl Ester (25a)

To an oven-dried, septaed 10 mL round-bottom flask, cooled under an argon atmosphere, and charged with N-BOC-glycine, 24a, (175.2 mg, 1.00 mmol) was added 2.5 mL freshly distilled $CH_2Cl_2$ under argon. The reaction was cooled to −15° C. and to the flask was added cyanuric fluoride (450 μL, 5 mmol). The reaction was stirred at −15° C. for 15 minutes then anhydrous pyridine (81 μL, 1.0 mmol) was added. Stirring was maintained at −15° C. for 90 minutes, with reaction progress indicated by the gradual formation of a precipitate. Without warming, the crude reaction was poured over ice, and immediately extracted twice with $CH_2Cl_2$. The combined $CH_2Cl_2$ extracts were washed once with water, dried over anhydrous magnesium sulfate, filtered, and concentrated in vacuo. The product crystallized upon storage at 0° C., affording 145.6 mg of 25a as white crystals. FTIR (neat) 1859 $cm^{-1}$.

(R)-(1-Fluorocarbonyl-ethyl)-carbamic Acid tert-butyl Ester (25b)

To an oven-dried, septaed 10 mL round-bottom flask, cooled under an argon atmosphere, and charged with (R)-N-BOC-alanine, 24b, (189.2 mg, 1.00 nmmol) was added 2.5 mL freshly distilled $CH_2Cl_2$ under argon. The reaction was cooled to −15 C and to the flask was added cyanuric fluoride (450 μL, 5 mmol). The reaction was stirred at −15° C. for 15 minutes then anhydrous pyridine (81 μL, 1.0 mmol) was added. Stirring was maintained at −15° C. for 90 minutes, with reaction progress indicated by the gradual formation of a precipitate. Without warming, the crude reaction was poured over ice, and immediately extracted twice with $CH_2Cl_2$. The combined $CH_2Cl_2$ extracts were washed once with water, dried over anhydrous magnesium sulfate, filtered, and concentrated in vacuo. The resulting colorless oil was dissolved in $CH_2Cl_2$, and precipitated with hexane to afford 155.1 mg of a mixture of 24b and 25b as white crystals. FTIR (film) 1842 $cm^{-1}$.

(S)-(1-Fluorocarbonyl-ethyl)-carbamic Acid tert-butyl Ester (25c)

To an oven-dried, septaed 10 mL round-bottom flask, cooled under an argon atmosphere, and charged with (S)-N-BOC-alanine, 24c, (189.2 mg, 1.00 mmol) was added 2.5 mL freshly distilled $CH_2Cl_2$ under argon. The reaction was cooled to −15° C. and to the flask was added cyanuric fluoride (450 μL, 5 mmol). The reaction was stirred at −15° C. for 15 minutes then anhydrous pyridine (81 μL, 1.0 mmol) was added. Stirring was maintained at −15° C. for 90 minutes, with reaction progress indicated by the gradual formation of a precipitate. Without warming, the crude reaction was poured over ice, and immediately extracted twice with $CH_2Cl_2$. The combined $CH_2Cl_2$ extracts were washed once with water, dried over anhydrous magnesium sulfate, filtered, and concentrated in vacuo. The resulting colorless oil was dissolved in $CH_2Cl_2$, and precipitated with hexane to afford 163.5 mg of a mixture of 24c and 25c as white crystals. FTIR (film) 1842 $cm^{-1}$.

(R)-2-Fluorocarbonyl-pyrrolidine-1-carboxylic Acid tert-butyl Ester (25d)

To an oven-dried, septaed 10 mL round-bottom flask, cooled under an argon atmosphere, and charged with (R)-N-BOC-proline, 24d, (215.3 mg, 1.00 mmol) was added 2.5 mL freshly distilled $CH_2Cl_2$ under argon. The reaction was cooled to −15° C. and to the flask was added cyanuric fluoride (450 μL, 5 mmol). The reaction was stirred at −15° C. for 15 minutes then anhydrous pyridine (81 μL, 1.0 mmol) was added. Stirring was maintained at −15° C. for 90 minutes. Without warming, the crude reaction was poured over ice, and immediately extracted twice with $CH_2Cl_2$. The combined $CH_2Cl_2$ extracts were washed once with water, dried over anhydrous magnesium sulfate, filtered, and concentrated in vacuo to afford 170.3 mg of 25d as a colorless oil. FTIR (neat) 1850 $cm^{-1}$.

(S)-2-Fluorocarbonyl-pyrrolidine-1-carboxylic Acid tert-butyl Ester (25e)

To an oven-dried, septaed 10 mL round-bottom flask, cooled under an argon atmosphere, and charged with (S)-N-BOC-proline, 24e, (215.3 mg, 1.00 mmol) was added 2.5 mL freshly distilled $CH_2Cl_2$ under argon. The reaction was cooled to −15° C. and to the flask was added cyanuric fluoride (450 μL, 5 mmol). The reaction was stirred at −15° C. for 15 minutes then anhydrous pyridine (81 μL, 1.0 mmol) was added. Stirring was maintained at −15° C. for 90 minutes. Without warming, the crude reaction was poured over ice, and immediately extracted twice with $CH_2Cl_2$. The combined $CH_2Cl_2$ extracts were washed once with water, dried over anhydrous magnesium sulfate, filtered, and concentrated in vacuo to afford 148.0 mg of 25e as a faintly yellow oil. FTIR (neat) 1850 $cm^{-1}$.

(R)-(1-Fluorocarbonyl-2-methyl-propyl)-carbamic Acid tert-butyl Ester (25f)

To an oven-dried, septaed 25 mL round-bottom flask, cooled under an argon atmosphere, and charged with (R)-

N-BOC-valine (217.1 mg, 1.00 mmol) was added 2.5 mL CH$_2$Cl$_2$, and pyridine (81 µL, 1.00 mmol). The solution was cooled to −15 C, and to the reaction was added cyanuric fluoride (450 µL, 5.0 mmol). The reaction remained clear, but turned yellow green. The reaction was stirred at −15° C. for 60 minutes, with the gradual formation of a precipitate and transition to pale yellow. Without warming, the crude reaction was poured over ice and immediately extracted twice with CH$_2$Cl$_2$. The combined CH$_2$Cl$_2$ extracts were washed once with ice-cold water, dried over anhydrous magnesium sulfate, and concentrated in vacuo to afford 222.2 mg of 25f as a white solid. FTIR (neat) 1844 cm$^{-1}$.

(S)-(1-Fluorocarbonyl-2-methyl-propyl)-carbamic Acid tert-butyl Ester (25g)

To an oven-dried, septaed 25 mL round-bottom flask, cooled under an argon atmosphere, and charged with (S)-N-BOC-valine (217.2 mg, 1.00 mmol) was added 2.5 mL CH$_2$Cl$_2$, and pyridine (81 µL, 1.00 mmol). The solution was cooled to −15° C., and to the reaction was added cyanuric fluoride (450 µL, 5.0 mmol). The reaction was stirred at −15° C. for 60 minutes, with the gradual formation of a white precipitate. Without warming, the crude reaction was poured over ice, and immediately extracted twice with CH$_2$Cl$_2$. The combined CH$_2$Cl$_2$ extracts were washed once with ice-cold water, dried over anhydrous magnesium sulfate, and concentrated in vacuo to afford 201.3 mg of 25g as white needles. FTIR (neat) 1847 cm$^{-1}$.

(R)-(1-Fluorocarbonyl-2,2-dimethyl-propyl)-carbamic Acid tert-butyl Ester (25h)

To an oven-dried, septaed 25 mL round-bottom flask, cooled under an argon atmosphere, and charged with 24h (170.3 mg, 0.74 mmol) was added 2.0 mL freshly distilled CH$_2$Cl$_2$ under argon. The reaction was cooled to −15 C and to the flask was added cyanuric fluoride (335 µL, 3.7 mmol). The reaction was stirred at −15 C for 15 minutes then anhydrous pyridine (60 µL, 0.74 mmol) was added. Stirring was maintained at −15 C for 60 minutes. Without warming, the crude reaction was poured over ice, and immediately extracted twice with CH$_2$Cl$_2$. The combined CH$_2$Cl$_2$ extracts were washed once with water, dried over anhydrous magnesium sulfate, filtered, and concentrated in vacuo to afford 112.6 mg of a mixture of 24h and 25h as an off-white solid.

(S)-(1-Fluorocarbonyl-2,2-dimethyl-propyl)-carbamic Acid tert-butyl Ester (25i)

To an oven-dried, septaed 10 mL round-bottom flask, cooled under an argon atmosphere, and charged with 24i (150.4 mg, 0.65 mmol) was added 2.0 mL freshly distilled CH$_2$Cl$_2$ under argon. The reaction was cooled to −15 C and to the flask was added cyanuric fluoride (295 µL, 3.25 mmol). The reaction was stirred at −15 C for 15 minutes then anhydrous pyridine (81 µL, 1.0 mmol) was added. Stirring was maintained at −15 C for 60 minutes. Without warming, the crude reaction was poured over ice, and immediately extracted twice with CH$_2$Cl$_2$. The combined CH$_2$Cl$_2$ extracts were washed once with water, dried over anhydrous magnesium sulfate, filtered, and concentrated in vacuo to afford 113.3 mg of a mixture of 24i and 25i as an off-white solid.

(R)-(Fluorocarbonyl-phenyl-methyl)carbamic Acid tert-butyl Ester (25j)

To an oven-dried, septaed 25 mL round-bottom flask, cooled under an argon atmosphere, and charged with 24j (124.9 mg, 0.50 mmol) was added 1.25 mL freshly distilled CH$_2$Cl$_2$ under argon. The reaction was cooled to −15 C and to the flask was added cyanuric fluoride (225 µL, 2.5 mmol). The reaction was stirred at −15 C for 15 minutes then anhydrous pyridine (40 µL, 0.5 mmol) was added. Stirring was maintained at −15 C for 60 minutes. Without warning, the crude reaction was poured over ice, and immediately extracted twice with CH$_2$Cl$_2$. The combined CH$_2$Cl$_2$ extracts were washed once with water, dried over anhydrous magnesium sulfate, filtered, and concentrated in vacuo to afford 114.8 mg of a mixture of 24j and 25j as an off-white solid. FTIR (film) 1849.3 cm$^{-1}$.

(S)-(Fluorocarbonyl-phenyl-methyl)carbamic Acid tert-butyl Ester (25k)

To an oven-dried, septaed 25 mL round-bottom flask, cooled under an argon atmosphere, and charged with 24k (125.8 mg, 0.50 mmol) was added 1.25 mL freshly distilled CH$_2$Cl$_2$ under argon. The reaction was cooled to −15 C and to the flask was added cyanuric fluoride (225 µL, 2.5 mmol). The reaction was stirred at −15 C for 15 minutes then anhydrous pyridine (40 µL, 0.5 mmol) was added. Stirring was maintained at −15 C for 60 minutes. Without warming, the crude reaction was poured over ice, and immediately extracted twice with CH$_2$Cl$_2$. The combined CH$_2$Cl$_2$ extracts were washed once with water, dried over anhydrous magnesium sulfate, filtered, and concentrated in vacuo to afford 115.3 mg of a mixture of 24k and 25k as an off-white solid. FTIR (film) 1849.3 cm$^{-1}$.

(R)-(1-Fluorocarbonyl-2-phenyl-ethyl)-carbamic Acid tert-butyl Ester (25l)

To an oven-dried, septaed 10 mL round-bottom flask, cooled under an argon atmosphere, and charged with 24l (265.3 mg, 1.00 mmol) was added 2.5 mL freshly distilled CH$_2$Cl$_2$ under argon. The reaction was cooled to −15 C and to the flask was added cyanuric fluoride (450 µL, 5.0 mmol). The reaction was stirred at −15 C for 15 minutes then anhydrous pyridine (81 µL, 1.0 mmol) was added. Stirring was maintained at −15 C for 90 minutes. Without warming, the crude reaction was poured over ice, and or immediately extracted twice with CH$_2$Cl$_2$. The combined CH$_2$Cl$_2$ extracts were washed once with water, dried over anhydrous magnesium sulfate, filtered, and concentrated in vacuo to afford 113.0 mg of a mixture of 24l and 25l as an off-white solid. FTIR (film) 1838.1 cm$^{-1}$.

(S)-(1-Fluorocarbonyl-2-phenyl-ethyl)-carbamic Acid tert-butyl Ester (25m)

To an oven-dried, septaed 10 mL round-bottom flask, cooled under an argon atmosphere, and charged with 24m (265.3 mg, 1.00 mmol) was added 2.5 mL freshly distilled CH$_2$Cl$_2$ under argon. The reaction was cooled to −15° C. and to the flask was added cyanuric fluoride (450 µL, 5.0 mmol). The reaction was stirred at −15° C. for 15 minutes then anhydrous pyridine (81 µL, 1.0 mmol) was added. Stirring was maintained at −15° C. for 90 minutes. Without warming, the crude reaction was poured over ice, and immediately extracted twice with CH$_2$Cl$_2$. The combined CH$_2$Cl$_2$ extracts were washed once with water, dried over anhydrous magnesium sulfate, filtered, and concentrated in vacuo to afford 136.0 mg of a mixture of 24m and 25m as an off-white solid. FTIR (film) 1847.5 cm$^{-1}$.

[(2-mercapto-ethylcarbamoyl)-methyl]carbamic Acid tert-butyl Ester (26a)

To a 50 mL round-bottom flask charged with a solution of sodium bicarbonate (141 mg, 1.68 mmol) in 8.2 mL water was added 2-aminoethanethiol hydrochloride (102.5 mg, 0.90 mmol). To this stirring solution was added dropwise over 60 seconds a solution of 25a (145.6 mg, 0.82 mmol) in 8.2 mL CH$_2$Cl$_2$. The reaction was vigorously stirred for 25 minutes at room temperature, then extracted twice with fresh CH$_2$Cl$_2$. The combined CH$_2$Cl$_2$ extracts were washed once with 5% aqueous HCl, once with 10% aqueous sodium bicarbonate, then once with water. The organic fraction was dried over anhydrous magnesium sulfate, filtered, and concentrated in vacuo to afford 132.8 mg (69% from 24a) of clean 26a as a colorless oil.

(S)-[1-(2-mercapto-ethylcarbamoyl)-ethyl]-carbamic Acid tert-butyl Ester (26b)

To a 25 mL round-bottom flask charged with a solution of sodium bicarbonate (139.5 mg, 1.66 mmol) in 8.1 mL water was added 2-aminoethanethiol hydrochloride (101.2 mg, 0.89 mmol). To this stirring solution was added dropwise over 60 seconds a solution of 25b (155.1 mg, 0.81 mmol) in 8.1 mL $CH_2Cl_2$. The reaction was vigorously stirred for 25 minutes at room temperature, then extracted twice with fresh $CH_2Cl_2$. The combined $CH_2Cl_2$ extracts were washed once with 5% aqueous HCl, once with 10% aqueous sodium bicarbonate, then once with water. The organic fraction was dried over anhydrous magnesium sulfate, filtered, and concentrated in vacuo to afford 72.6 mg (36% from 24b) of clean 26b as a colorless oil.

(S)-[1-(2-mercapto-ethylcarbamoyl)-ethyl]-carbamic Acid tert-butyl Ester (26c)

To a 25 mL round-bottom flask charged with a solution of sodium bicarbonate (148.1 mg, 1.76 mmol) in 8.6 mL water was added 2-aminoethanethiol hydrochloride (107.5 mg, 0.95 mmol). To this stirring solution was added dropwise over 60 seconds a solution of 25c (163.5 mg, 0.86 mmol) in 8.6 mL $CH_2Cl_2$. The reaction was vigorously stirred for 25 minutes at room temperature, then extracted twice with fresh $CH_2Cl_2$. The combined $CH_2Cl_2$ extracts were washed once with 5% aqueous HCl, once with 10% aqueous sodium bicarbonate, then once with water. The organic fraction was dried over anhydrous magnesium sulfate, filtered, and concentrated in vacuo to afford 108.0 mg (51% from 24c) of clean 26c as a colorless oil.

(R)-2-(2-mercapto-ethylcarbamoyl)-pyrrolidine-1-carboxylic Acid tert-butyl Ester (26d)

To a 50 mL round-bottom flask charged with a solution of sodium bicarbonate (134.3 mg, 1.6 mmol) in 7.8 mL water was added 2-aminoethanethiol hydrochloride (97.5 mg, 0.86 mmol). To this stirring solution was added dropwise over 60 seconds a solution of 25d (170.3 mg, 0.78 mmol) in 7.8 mL $CH_2Cl_2$. The reaction was vigorously stirred for 25 minutes at room temperature, then extracted twice with fresh $CH_2Cl_2$. The combined $CH_2Cl_2$ extracts were washed once with 5% aqueous HCl, once with 10% aqueous sodium bicarbonate, then once with water. The organic fraction was dried over anhydrous magnesium sulfate, filtered, and concentrated in vacuo to afford 205.8 mg (96% from 24d) of clean 26d as a colorless oil.

(S)-2-(2-mercapto-ethylcarbamoyl)-pyrrolidine-1-carboxylic Acid tert-butyl Ester (26e)

To a 50 mL round-bottom flask charged with a solution of sodium bicarbonate (117.0 mg, 1.39 mmol) in 6.8 mL water was added 2-aminoethanethiol hydrochloride (85.0 mg, 0.75 mmol). To this stirring solution was added dropwise over 60 seconds a solution of 25e (148.0 mg, 0.78 mmol) in 6.8 mL $CH_2Cl_2$. The reaction was vigorously stirred for 25 minutes at room temperature, then extracted twice with fresh $CH_2Cl_2$. The combined $CH_2Cl_2$ extracts were washed once with 5% aqueous HCl, once with 10% aqueous sodium bicarbonate, then once with water. The organic fraction was dried over anhydrous magnesium sulfate, filtered, and concentrated in vacuo to afford 169.2 mg (91% from 24e) of clean 26e as a pale yellow oil.

(R)-[1-(2-mercapto-ethylcarbamoyl)-2-methyl-propyl]-carbamic Acid tert-butyl Ester (26f)

To a 50 mL round-bottom flask charged with a solution of sodium bicarbonate (1 74.0 mg, 2.07 mmol) in 10.1 mL was added 2-aminoethanethiol hydrochloride (126.6 mg, 1.11 mmol). To this stirring solution was added dropwise over 60 seconds a solution of 25f (222.2 mg, 1.0 mmol) in 10.1 mL $CH_2Cl_2$. The reaction was vigorously stirred for 25 minutes at room temperature, then extracted twice with fresh $CH_2Cl_2$. The combined $CH_2Cl_2$ extracts were washed once with 5% aqueous HCl, once with 10% aqueous sodium bicarbonate, then once with water. The organic fraction was dried over anhydrous magnesium sulfate, filtered, and concentrated in vacuo, to afford 195.2 mg (71% from 24f) of clean 26f as a white solid. FTIR (film) 3289, 1687, 1645 $cm^{-1}$.

(S)-[1-(2-mercapto-ethylcarbamoyl)-2-methyl-propyl]-carbamic Acid tert-butyl Ester (26g)

To a 50 mL round-bottom flask charged with a solution of sodium bicarbonate (158.1 mg, 1.88 mmol) in 9.2 mL water was added 2-aminoethanethiol hydrochloride (114.7 mg, 1.01 mmol). To this stirring solution was added dropwise over 60 seconds a solution of 25g (201.3 mg, 0.92 mmol) in 9.2 mL $CH_2Cl_2$. The reaction was vigorously stirred for 25 minutes at room temperature, then extracted twice with fresh $CH_2Cl_2$. The combined $CH_2Cl_2$ extracts were washed once with 5% aqueous HCl, once with 10% aqueous sodium bicarbonate, then once with water. The organic fraction was dried over anhydrous magnesium sulfate, filtered, and concentrated in vacuo, to afford 222.0 mg (80% from 24g) of clean 26g as a colorless oil. FTIR (neat) 3300, 1681, 1652 $cm^{-1}$.

(R)-[1-(2-mercapto-ethylcarbamoyl)-2,2-dimethyl-propyl]-carbamic Acid tert-butyl Ester (26h)

To a 25 mL round-bottom flask charged with a solution of sodium bicarbonate (83.0 mg, 0.99 mmol) in 4.8 mL water was added 2-aminoethanethiol hydrochloride (60.3 mg, 0.53 mmol). To this stirring solution was added dropwise over 60 seconds a solution of 25h (112.6 mg, 0.48 mmol) in 4.8 mL $CH_2Cl_2$. The reaction was vigorously stirred for 25 minutes at room temperature, then extracted twice with fresh $CH_2Cl_2$. The combined $CH_2Cl_2$ extracts were washed once with 5% aqueous HCl, once with 10% aqueous sodium bicarbonate, then once with water. The organic fraction was dried over anhydrous magnesium sulfate, filtered, and concentrated in vacuo to afford 26h as a colorless oil.

(S)-[1-(2-mercapto-ethylcarbamoyl)-2,2-dimethyl-propyl]-carbamic Acid tert-butyl Ester (26i)

To a 25 mL round-bottom flask charged with a solution of sodium bicarbonate (83.6 mg, 1.0 mmol) in 4.9 mL water was added 2-aminoethanethiol hydrochloride (60.7 mg, 0.53 mmol). To this stirring solution was added dropwise over 60 seconds a solution of 25i (113.3 mg, 0.48 mmol) in 4.9 mL $CH_2Cl_2$. The reaction was vigorously stirred for 25 minutes at room temperature, then extracted twice with fresh $CH_2Cl_2$. The combined $CH_2Cl_2$ extracts were washed once with 5% aqueous HCl, once with 10% aqueous sodium bicarbonate, then once with water. The organic fraction was dried over anhydrous magnesium sulfate, filtered, and concentrated in vacuo to afford 26i as a colorless oil.

(R)-[(2-mercapto-ethylearbamoyl)-phenyl-methyl]-carbamic Acid tert-butyl Ester (26j)

To a 50 mL round-bottom flask charged with a solution of sodium bicarbonate (78.0 mg, 0.93 mmol) in 4.5 mL water was added 2-aminoethanethiol hydrochloride (56.6 mg, 0.50 mmol). To this stirring solution was added dropwise over 60 seconds a solution of 25j (114.8 mg, 0.45 mmol) in 4.5 mL $CH_2Cl_2$. The reaction was vigorously stirred for 25 minutes at room temperature, then extracted twice with fresh $CH_2Cl_2$. The combined $CH_2Cl_2$ extracts were washed once with 5% aqueous HCl, once with 10% aqueous sodium bicarbonate, then once with water. The organic fraction was dried over anhydrous magnesium sulfate, filtered, and concentrated in vacuo to afford 132.3 mg (86% from 24j) of 26j as an off-white paste.

(S)-[(2-mercapto-ethylcarbamoyl)-phenyl-methyl]-carbamic Acid tert-butyl Ester (26k)

To a 50 mL round-bottom flask charged with a solution of sodium bicarbonate (78.4 mg, 0.93 mmol) in 4.6 mL water was added 2-aminoethanethiol hydrochloride (57.0 mg, 0.50 mmol). To this stirring solution was added dropwise over 60 seconds a solution of 25k (115.3 mg, 0.46 mmol) in 4.6 mL $CH_2Cl_2$. The reaction was vigorously stirred for 25 minutes at room temperature, then extracted twice with fresh $CH_2Cl_2$. The combined $CH_2Cl_2$ extracts were washed once with 5% aqueous HCl, once with 10% aqueous sodium bicarbonate, then once with water. The organic fraction was dried over anhydrous magnesium sulfate, filtered, and concentrated in vacuo to afford 130.8 mg (84% from 24k) of 26k as an off-white paste.

(R)-[1-(2-mercapto-ethylcarbamoyl)-2-phenyl-ethyl]-carbamic Acid tert-butyl Ester (26l)

To a 25 mL round-bottom flask charged with a solution of sodium bicarbonate (17 mg, 0.20 mmol) in 1.0 mL water was added 2-aminoethanethiol hydrochloride (12.0 mg, 0.10 mmol). To this stirring solution was added dropwise over 60 seconds a solution of 25l (25.6 mg, 96 μmol) in 1.0 mL $CH_2Cl_2$. The reaction was vigorously stirred for 25 minutes at room temperature, then extracted twice with fresh $CH_2Cl_2$. The combined $CH_2Cl_2$ extracts were washed once with 5% aqueous HCl, once with 10% aqueous sodium bicarbonate, then once with water. The organic fraction was dried over anhydrous magnesium sulfate, filtered, and concentrated in vacuo to afford 30.0 mg (97%) of 26l as a colorless oil.

(S)-[1-(2-mercapto-ethylcarbamoyl)-2-phenyl-ethyl]-carbamic Acid tert-butyl Ester (26m)

To an oven-dried, septaed 10 mL round-bottom flask, cooled under an argon atmosphere, and charged with 25m (136.0 mg, 0.51 mmol) and 2-aminoethanethiol hydrochloride (57.8 mg, 0.51 mmol) were added 2 mL freshly distilled $CH_2Cl_2$ and anhydrous pyridine (82 μL, 1.02 mmol). The reaction immediately clouded then cleared after 30 minutes. The reaction was stirred for 3 hours at room temperature, then poured into water and extracted twice with $CH_2Cl_2$. The combined $CH_2Cl_2$ extracts were washed once with 5% aqueous HCl, once with 10% aqueous sodium bicarbonate, once with saturated brine, then once with water. The organic fraction was dried over anhydrous magnesium sulfate, filtered, and concentrated in vacuo to afford 123.0 mg (38% from 24m) of 26m as a colorless oil.

(S)-2-Amino-N-(2-mercapto-ethyl)-acetamide (27a)

To 26a in a 25 mL round-bottom flask purged with argon were added 1.5 mL freshly distilled $CH_2Cl_2$, 500 gL triethylsilane, and 250 μL trifluoroacetic acid. The reaction was stirred for 75 minutes at room temperature, then concentrated in vacuo. The crude product was purified by silica gel chromatography using 15% methanolic $CH_2Cl_2$ as eluant. Clean fractions were combined, and concentrated in vacuo to afford 71 mg (93%) of 27a as a pale yellow oil.

(R)-2-Amino-N-(2-mercapto-ethyl)-propionamide (27b)

To 26b in a 25 mL round-bottom flask purged with argon were added 1.0 mL freshly distilled $CH_2Cl_2$, 500 μL triethylsilane, and 250 μL trifluoroacetic acid. The reaction was stirred for 1 hour at room temperature, then concentrated in vacuo. The crude product was purified by silica gel chromatography using 15% methanolic $CH_2Cl_2$ as eluant. Clean fractions were combined, and concentrated in vacuo to afford 39.6 mg (92%) of 27b as a pale yellow oil.

(S)-2-Amino-N-(2-mercapto-ethyl)-propionamide (27c)

To 26c in a 25 mL round-bottom flask purged with argon were added 1.0 mL freshly distilled $CH_2Cl_2$, 500 μL triethylsilane, and 250 μL trifluoroacetic acid. The reaction was stirred for 1 hour at room temperature, then concentrated in vacuo. The crude product was purified by silica gel chromatography using 15% methanolic $CH_2Cl_2$ as eluant. Clean fractions were combined, and concentrated in vacuo to afford 48 mg (74%/) of 27c as a pale yellow oil.

(R)-Pyrrolidine-2-carboxylic Acid (2-mercapto-ethyl)-amide (27d)

To 26d in a 25 mL round-bottom flask purged with argon were added 1.5 mL freshly distilled $CH_2Cl_2$, 500 μL triethylsilane, and 250 μL trifluoroacetic acid. The reaction was stirred for 75 minutes at room temperature, then concentrated in vacuo. The crude product was purified by silica gel chromatography using 10% methanolic $CH_2Cl_2$ as eluant. Clean fractions were combined, and concentrated in vacuo to afford 102.6 mg (79%) of 27d as a pale yellow oil.

(S)-Pyrrolidine-2-carboxylic Acid (2-mercapto-ethyl)-amide (27e)

To 26e in a 25 mL round-bottom flask purged with argon were added 1.5 mL freshly distilled $CH_2Cl_2$, 500 μL triethylsilane, and 250 μL trifluoroacetic acid. The reaction was stirred for 75 minutes at room temperature, then concentrated in vacuo. The crude product was purified by silica gel chromatography using 15% methanolic $CH_2Cl_2$ as eluant. Clean fractions were combined, and concentrated in vacuo to afford 102.0 mg (78%) of 27e as a pale yellow oil.

(R)-2-Amino-N-(2-mercapto-ethyl)-3-methyl-butyramide (27f) To 26f (195.2 mg, 0.71 mmol) in a 100 mL round-bottom flask purged with argon were added $CH_2Cl_2$ (1.76 mL, 27.5 mmol), triethylsilane (1.13 mL, 7.1 mmol), and trifluoroacetic acid (544 μL, 7.1 mmol). The reaction was stirred for 90 minutes at room temperature, then concentrated in vacuo. The crude product was purified by silica gel chromatography using 10% methanolic $CH_2Cl_2$ as eluant. Clean fractions were combined, and concentrated in vacuo to afford 27f as a white solid.

(S)-2-Amino-N-(2-mercapto-ethyl)-3-methyl-butyramide (27g)

To 26g (222.0 mg, 0.80 mmol) in a 100 mL round-bottom flask purged with argon were added $CH_2Cl_2$ (2.00 mL, 31.2 mmol), triethylsilane (1.28 mL, 8.0 mmol), and trifluoroacetic acid (616 μL, 8.0 mmol). The reaction was stirred for 2.5 hours at room temperature, then concentrated in vacuo. The crude product was purified by silica gel chromatography using 10% methanolic $CH_2Cl_2$ as eluant. Clean fractions were combined, and concentrated in vacuo to afford 27g as a colorless oil.

(R)-2-Amino-N-(2-mercapto-ethyl)-3,3-dimethyl-butyramide (27h)

To 26h in a 25 mL round-bottom flask purged with argon were added 1.0 mL freshly distilled $CH_2Cl_2$, 500 μL triethylsilane, and 250 μL trifluoroacetic acid. The reaction was stirred for 45 minutes at room temperature, then concentrated in vacuo. The crude product was purified by silica gel chromatography using 10% methanolic $CH_2Cl_2$ as eluant. Clean fractions were combined, and concentrated in vacuo to afford 6.8 mg (5% from 24h) of 27h as a pale yellow oil.

(S)-2-Amino-N-(2-mercapto-ethyl)-3,3-dimethyl-butyramide (27i)

To 26i in a 25 mL round-bottom flask purged with argon were added 1.0 mL freshly distilled $CH_2Cl_2$, 500 μL triethylsilane, and 250 μL trifluoroacetic acid. The reaction was stirred for 45 minutes at room temperature, then concentrated in vacuo. The crude product was purified by silica gel chromatography using 10% methanolic $CH_2Cl_2$ as eluant. Clean fractions were combined, and concentrated in vacuo to afford 22.3 mg (18% from 24i) of 27i as a pale yellow oil.

(R)-2-Amino-N-(2-mercapto-ethyl)-2-phenyl-acetamide (27j)

To 26j in a 25 mL round-bottom flask purged with argon were added 1.0 mL freshly distilled $CH_2Cl_2$, 500 μL triethylsilane, and 250 μL trifluoroacetic acid. The reaction was stirred for 45 minutes at room temperature, then concentrated in vacuo. The crude product was purified by silica gel chromatography using 5% methanolic $CH_2Cl_2$ as eluant. Clean fractions were combined, and concentrated in vacuo to afford 37.7 mg (42%) of 27j as a pale yellow oil.

(S)-2-Amino-N-(2-mercapto-ethyl)-2-phenyl-acetamide (27k)

To 26k in a 25 mL round-bottom flask purged with argon were added 1.0 mL freshly distilled $CH_2Cl_2$, 500 μL triethylsilane, and 250 μL trifluoroacetic acid. The reaction was stirred for 45 minutes at room temperature, then concentrated in vacuo. The crude product was purified by silica gel chromatography using 5% methanolic $CH_2Cl_2$ as eluant. Clean fractions were combined, and concentrated in vacuo to afford 59.2 mg (67%) of 27k as a pale yellow oil.

(R)-2-Amino-N-(2-mercapto-ethyl)-3-phenyl-propionamide (27l)

To 26l in a 25 mL round-bottom flask purged with argon were added 1.0 mL freshly distilled $CH_2Cl_2$, 250 μL triethylsilane, and 250 μL trifluoroacetic acid. The reaction was stirred for 20 minutes at room temperature, then concentrated in vacuo. The crude product was purified by silica gel chromatography using 15% methanolic $CH_2Cl_2$ as eluant. Clean fractions were combined, and concentrated in vacuo to afford 14.0 mg (71%) of 27l as a pale yellow oil.

(S)-2-Amino-N-(2-mercapto-ethyl)-3-phenyl-propionamide (27m)

To 26m in a 25 mL round-bottom flask purged with argon were added 3.8 mL freshly distilled $CH_2Cl_2$, and 3.8 mL trifluoroacetic acid. The reaction was stirred for 20 minutes at room temperature, then concentrated in vacuo. The crude product was purified by silica gel chromatography using 15% methanolic $CH_2Cl_2$ as eluant. Clean fractions were combined, and concentrated in vacuo to afford 42.0 mg (49%) of 27m as a pale yellow oil.

Chemical Derivatization of Glass Microscope Slides

Derivatization of glass microscope slides was performed, with minor modifications, as described by Schreiber et. al. (*J. Am. Chem. Soc.,* 1999, 121, 7967–7968 and supporting information. Details for the Schreiber procedure, as well as information on custom slide-sized reaction chambers are available on the World Wide Web at http://www-schreiber.chem.harvard.edu/home/protocols/SMP.html.) Plain glass slides were cleaned in piranha solution (7:3 v/v mixture of 95–98% $H_2SO_4$ and 30% $H_2O_2$) for 12 hours at room temperature. The slides were rinsed thoroughly with distilled water then treated with 3% 3-aminopropyl-triethoxysilane in 95% ethanol for 1 hour. Prior to immersing the slides, the solution was stirred for at least 15 minutes. The slides were briefly dipped in 95% ethanol, then dried by centrifugation at 2000 rpm. The slides were cured for 3 hours at 115° C., then cooled to room temperature in a dessiccator over $P_2O_5$. The amino-functionalized slides were transferred to slide-sized polydimethylsiloxane (PDMS) reaction vessels, and one face was treated with 20 mM N-succinimidyl 3-maleimido propionate in 50 mM $NaHCO_3$ buffer, pH ~8.3., for 4 hours at room temperature. The plates were washed thoroughly with distilled water, rinsed with 95% ethanol, then immersed in a stirring solution of a catalytic amount of pyridine in acetic anhydride for at least 6 hours at room temperature. The slides were then washed in 95% ethanol, dipped in absolute methanol, and dried by centrifugation. Derivatized slides were stored over $P_2O_5$ until needed.

Arraying Thiols Onto Derivatized Glass Microscope Slides

Thiol-containing amino acid derivatives (27a–m) were dissolved in DMF to a concentration of approximately 30 mM. From these stock solutions, ratios of enantiomeric thiols were mixed to make solutions with enantiomeric excesses (e.e.) of approximately 100%, 80%, 60%, 40%, 20%, and 0% (eleven solutions in total). From these stock solutions were taken 5 μL aliquots which were transferred to a 96-well polypropylene V-bottom plate, and a fraction of the contents of each well was arrayed by robot on the derivatized microscope slides. The microarraying robot used in this procedure was constructed using directions provided on the World Wide Web at http://cmgm.stanford.edu.pbrown/mguide/index.html, and was made accessible by the Harvard University Center for Genomics Research (http:/fcgr.harvard.edu/). After arraying was complete, the slides were incubated at room temperature for 24 hours, then washed for 1 hour in DMF, one hour in THF, and one hour in isopropyl alcohol. Slides were rinsed briefly in methanol, dried by centrifuigation, and stored at room temperature until acylation. The following amino acids were arrayed in the following rows (row A through row F) and columns (column 1 through column 12):

| Amino Acid | Row | Column |
| --- | --- | --- |
| Glycine (Gly, achiral substrate) | A | 1–12 |
| Alanine (Ala) | B | 1–12 |
| Proline (Pro) | C | 1–12 |
| tert-Leucine (t-Leu) | D | 1–12 |
| Phenylglycine (Phg) | E | 1–12 |
| Phenylalanine (Phe) | F | 1–12 |

In the arrays of the chiral amino acids the enantiomer in excess in columns 1 through 5 was intended to be D, while the L enantiomer was intended to be the excess enantiomer in columns 7 through 12. Columns 6 and 7 were intended to contain a nearly racemic (0% enantiomeric excess) mixture.

Acylation of Arrayed Thiols by Chiral Cy3 and Cy5 Fluorophores as Their Pentafluorophenyl Esters Derivatized microscope slides that were arrayed with small molecules were placed in PDMS reaction vessels. In a typical procedure, a 1:1 mixture of enantiomerically-related Cy3-(R)-proline conjugate 16 and Cy5-(S)-proline conjugate 21 (ratio determined by 400 MHz NMR, integrating downfield triplets near 8 ppm; the Cy3 triplet is downfield from that of Cy5) was dissolved in DMF to an approximate concentration of 10 mM. Pentafluorophenyl diphenylphosphinate (FDPP, 19.2 mg, 0.05 mmol) was dissolved in 225 μL DMF and to this was added DIPEA (8.7 μL, 0.05 mmol) and the solution was mixed thoroughly. A 1 μL aliquot was diluted 1000-fold with DMF, yielding a solution approximately 200 μM in FDPP and DIPEA. In a separate vial was mixed 1423.5 μL of DMF, 1.5 μL of the Cy3/Cy5 mixture, and 75 μL of the coupling reagent solution. This concentration of Cy3/Cy5 represents a 3000–4000-fold molar excess of fluorophores to printed substrates. As much of this mixture as necessary (1.2–1.5 mL) was pipetted under the arrayed slide, and the reaction vessel was incubated in the absence of light at −20° C. for 14 hours. After incubation, the slide was washed in the dark at room temperature for 1.5 hours in DMF then 1.5 hours in methanol, and finally dried by centrifugation. The slide was then scanned for Cy3 and Cy5 fluorescence.

Acylation of Arrayed Thiols by Chiral Cy3 and Cy5 Fluorophores, PyBOP, and DIPEA Derivatized microscope slides that were arrayed with small molecules were placed in PDMS reaction vessels. In a typical procedure, a 1:1 mixture of enantiomerically-related Cy3-(R)-proline conjugate 16 and Cy5-(S)-proline conjugate 21 (ratio determined by 400 MHz NMR, integrating downfield triplets near 8 ppm; the Cy3 triplet is downfield from that of Cy5) was dissolved in DMF to an approximate concentration of 10 mM. PyBOP (26.0 mg, 0.05 mmol) was dissolved in 220 µL DMF and to this was added DIPEA (8.7 µL, 0.05 mmol) and the solution was mixed thoroughly. A 1 µL aliquot was diluted 1000-fold with DMF, yielding a solution approximately 200 µM in PyBOP and DIPEA. In a separate vial was mixed 1423.5 µL of DMF, 1.5 µL of the Cy3/Cy5 mixture, and 75 µL of the coupling reagent solution. This concentration of Cy3/Cy5 represents a 3000–4000-fold molar excess of fluorophores to printed substrates. As much of this mixture as necessary (1.2–1.5 mL) was pipetted under the arrayed slide, and the reaction vessel was incubated in the absence of light at −20 C for 14 hours. After incubation, the slide was washed in the dark at room temperature for 1.5 hours in DMF then 1.5 hours in methanol, and finally dried by centrifugation. The slide was then scanned for Cy3 and Cy5 fluorescence.

Imaging of Cy3/Cy5-acylated Microarrays of Thiol-containing Compounds

Imaging of acylated microarrays was performed with an Applied Precision ArrayWorx scanner, made accessible by the Harvard University Center for Genomics Research. Identical exposure times of 0.25 seconds were chosen for both fluorophores. Cy3 emission intensity is monitored at 595 nm, and Cy5 emission intensity is monitored at 685 nm. The resulting scans are stitched together electronically to yield a false-colored picture of the entire array in which Cy3 emission is colored green and that for Cy5 is colored red. Using the program software the ratio of intensities at 685 and 595 nm ($I_{685}/I_{595}$) is obtained directly. A difference in color between enantiomers and between a chiral compound at known enantiomeric excesses is indicative of kinetic resolution in the amide bond-forming step. This color difference is reflected quantitatively in the changing ratios of fluorescent intensity, and from these values is obtained the values for kinetic resolution (kinetic resolution=k.r.=s; defined as the ratio of the fast rate to the slow rate of reaction) and calculated enantiomeric excess.

Calculation of Kinetic Resolution and Enantiomeric Excess of Thiol Microarrays Acylated by Cy3/Cy5 as Their Pentafluorophenyl Esters The following table shows the calculated values of s and percentage enantiomeric excess for the chiral amino acids Ala, Pro, and Phe. Absolute configuration of the enantiomer in excess in a given spot is given in parentheses after the value of the enantiomeric excess, and using the D and L nomenclature. The use of FDPP as an activation reagent did not yield a significant value of kinetic resolution for phenylglycine. Due to inconsistent arraying reliable data was unavailable for the determination of an s value and subsequent calculation of enantiomeric excess of printed spots of tert-leucine.

| Amino acid | | | | | | |
|---|---|---|---|---|---|---|
| Ala (s = 2.0) | | | | | | |
| 100(D) | 87.5(D) | 60.4(D) | 39.7(D) | 21.5(D) | 7.4(D) | 13.4(D) |
| 5.2(L) | 25.1(L) | 49.3(L) | 71.0(L) | 100(L) | | |
| Pro (s = 4.7) | | | | | | |
| 100(D) | 87.0(D) | 72.2(D) | 58.3(D) | 43.4(D) | 31.0(D) | |
| 34.2(D) | 20.1(D) | 6.3(D) | 12.0(L) | 39.0(L) | | 100(L) |
| Phe (s = 1.8) | | | | | | |
| 100(D) | 85.0(D) | 61.5(D) | 39.6(D) | 18.4(D) | 0.7(D) | 10.4(D) |
| 3.4(L) | 30.6(L) | 53.3(L) | 81.9(L) | 100(L) | | |

Calculation of Kinetic Resolution and Enantiomeric Excess of Microarrays Acylated by Cy3/Cy5, PyBOP, and DIPEA The following table shows the calculated values of s and percentage enantiomeric excess for the chiral amino acid tert-leucine. Absolute configuration of the enantiomer in excess in a given spot is given in parentheses after the value of the enantiomeric excess, and using the D and L nomenclature.

| Amino acid | | | | | |
|---|---|---|---|---|---|
| t-Leu (s = 1.4) | | | | | |
| 100(D) | 55.3(D) | 28.8(D) | --N/A-- | 33.7(D) | 34.8(D) |
| 37.6(D) | 6.8(D) | 6.3(L) | 46.0(L) | 70.8(L) | 100(L) |

Arraying N-Boc Amino Acids Onto Derivatized Glass Microscope Slides

In a typical experiment ~500 mg of N-BOC-protected (α- and β-amino acids were independently dissolved in dimethylformamide (DMF) to a concentration of 1.00 M. The amino acids investigated were: glycine; alanine; valine; leucine; proline; serine; S-acetamido-cysteine; phenylalanine; 3-amino-4-(4-methylphenyl)butyric acid; 3-amino-3-pbenylpropionic acid; 3-amino-5-hexenoic acid. For aliphatic α-amino acids an aliquot of each enantiomer was diluted to 10 mM, and solutions of enantiomeric amino acids were combined via micropipettors to the appropriate calculated enantiomeric excess (e.e.) in increments of 10% e.e. A separate solution in DMF was prepared to be 10 mM in 7-azabenzotriazol-1-yloxytris(pyrrolidino)phosphonium hexafluorophosphate (PyAOP) and 10 mM in diisopropylethylamine. Amino acids and coupling reagent were combined and diluted with DMF to a final concentration of 2 mM. Solutions were transferred to 96-well polypropylene V-bottom plates, and arrayed using a Affymetrix 417 arrayer (125 µm standard, 4-pin operation; array mode; X-axis spacing=375 µm; Y-axis spacing=750 µm; 2 replicates; 5 second, single, non-recirculating acetone wash; 3 second vacuum dry) made available by the Harvard University Center for Genomics Research, onto γ-aminopropylsilane coated 25mm×75mm microslides (CMT-GAPS, Corning Glass).

Aromatic α-amino acids and all β-amino acids were evaluated by coupling with PyBOP and diisopropylethylamine at printing concentrations of 10 mM. All other technical and instrumental parameters were identical to those for aliphatic cc-amino acids. All arrayed microslides were incubated at room temperature for 14 hours, then washed in each of DMF, THF, and 2-propanol for 1 hour. Washed slides were then treated with 3% pyridine in acetic anhydride for 6 hours to acetylate residual free amino termini. Two hours treatment with 10% trifluoracetic acid in methylene chloride afforded BOC-deprotection, and 2 hours treatment with 3% triethylamine in methylene chloride afforded the free base of the arrayed amino acids. The slides were washed briefly in methanol, dried by centrifugation, and used without further modification.

Acylation of Arrayed Amino acids by Chiral Cy3 and Cy5 Fluorophores

Derivatized microscope slides that were arrayed with amino acids were placed in polydimethylsiloxane (PDMS) reaction vessels. These reaction vessels were prepared as described by Schreiber et. al. (*J. Am. Chem. Soc.*, 1999, 121, 7967–7968 and supporting information therein.) A 1:1 mixture of pseudo-enantiomeric Cy3-(R)-proline conjugate 16 and Cy5-(S)-proline conjugate 21 (ratio determined by integration of single-proton signals using 500 MHz NMR; Cy3 triplet at 8.3 ppm; Cy5 doublet at 6.1 ppm; measured ratio, Cy3:Cy5=1.00:1.03) was dissolved in DMF to an approximate concentration of 10 mM. In a typical procedure for aliphatic α-amino acids, pentafluorophenyl diphenylphosphinate (FDPP, 19.2 mg, 0.05 mmol) was dissolved in 225 μL DMF and to this was added DIPEA (8.7 μL, 0.05 mmol) and the solution was mixed thoroughly. A 1 μL aliquot was diluted 1000-fold with DMF, yielding a solution approximately 200 μM in FDPP and DIPEA. In a separate vial was mixed 1423.5 μL of DMF, 1.5 μL of the Cy3/Cy5 mixture, and 75 μL of the coupling reagent solution. This concentration of Cy3/Cy5 represents a >3000-fold molar excess of fluorophores to printed substrates. As much of this mixture as necessary (1.2–1.5 mL) was pipetted under the arrayed slide, and the reaction vessel was incubated in the absence of light at −20 C for 12 hours. After incubation, the slide was washed in the dark at room temperature for 1 hour in DMF then 1–1.5 hours in methanol, and finally dried by centrifugation. The slide was then scanned for Cy3 and Cy5 fluorescence.

In a typical procedure for arrayed aromatic α- and all β-amino acids, O-(7-azabenzotriazol-1-yl)-N,N,N',N'-tetramethyluronium hexafluorophosphate (HATU, 26 mg, 0.05 mmol) and 1-hydroxy-7-azabenzotriazole (HOAt, 6.8 mg, 0.05 mmol) were substituted for PyBOP. All other chemical and technical parameters were identical to those performed for arrayed aliphatic α-amino acids.

Imaging of Cy3/Cy5 Acylated Microarrays of Amino Acids

Imaging of Cy3/Cy5 acylated microarrays was performed using a GenePix 4000A scanner (Axon Instruments, Inc.,) made available by the Harvard University Center for Genomics Research. Excitation was performed for Cy3 at 532 nm (PMT detector voltage=490 V) and for Cy5 at 635 nm (700 V), with scanning at 10 μm resolution. Graphic visualization was performed with the "preserve high intensities" method of ratio processing. Cy3 fluorescence was mapped to the green channel,and Cy5 to the red channel, resulting in a 24-bit composite RGB overlay image which was exported to Adobe Photoshop 5.1 as a TIFF file.

Calculation of Kinetic Resolutions and Enantiomeric Excesses on Amino Acid Microarrays Individual spots were analyzed using GenePix 4000A software, and the background-subtracted mean of ratios (arithmetic mean of background-subtracted pixel-by-pixel ratios of raw pixel intensities) was used for calculation of kinetic resolution and subsequent calculation of measured e.e. The mean of ratios value for each racemic (0% e.e.) chiral amino acid was used to determine the fluorescent intensity normalization factor for all other mean of ratios values for that amino acid. The normalized ratios for enantiopure (>99% e.e.) amino acids were applied to a rearranged version of Horeau's equation, where for 100% e.e., s=y, and a quantitative value for kinetic resolution is obtained directly. This calculated s value for each enantiopure amino acid was then used to calculate the e.e. for each spot with that enantiomer in excess. Mean of ratios data was rejected from further consideration if the standard deviation in the mean of ratios exceeded one-half the mean of ratios value. Data from 12 arrays were pooled, and statistical outliers were rejected from pooled statistical analysis using the Q-test at 95% CL. The resulting body of data for each amino acid at each actual e.e. was evaluated for: number of valid cases; arithmetic mean; standard error of the mean; variance; standard deviation; minimum value; maximum value; range; median; and geometric mean. The arithmetic mean was plotted against the actual enantiomeric excess (100% e.e. D-amino acid arbitrarily defined as +100%; 100% e.e. L-amino acid as −100%) with error bars defined by values of the standard error of the mean. Plots, as defined above, were fit to a straight line of form y=ax+b using non-weighted linear least-squares analysis.

Preparation of Nitrone-derivatized Microslides for the Attachment of Olefins

CMT-GAPS slides were functionalized with nitrones by amide coupling nitrone acids to the surface with PyBOP and DIPEA in DMF. [[Benzyl]oxidoimino]acetic acid or [[methyl]oxidoimino]acetic acid were the nitone acids of choice, and were prepared in similar fashion to that described by Schreiber et. al. (*J. Am. Chem. Soc.*, 1998, 120, 8565.) In a typical preparation, approximately 100 μmol of nitrone acid was mixed with 100 μmol of PyBOP and 100 μmol of DIPEA in 1.5 mL DMF. This solution was pipetted under a GAPS microslides using the reaction vessels described above, and the amide-coupling was allowed to proceed for at least 4 hours. The slides were washed with DMF, rinsed with methylene chloride and dried under vacuum.

Preparation of Selenyl Bromide-functionalized Microslides for the Attachment of Olefins CMT-GAPS slides were functionalized with bis(4-carboxyphenyl)-diselenide by amide coupling the diselenide diacid to the surface with PyBOP and DIPEA in DMF. The bis(4-carboxyphenyl)-diselenide used in this process was prepared according to literature procedure as described by Mlochowski et al. (*Liebigs Ann. Chem.*, EN, 1993, 12, 1239.). Prior to printing of olefin-containing substrates, the diselenides were converted to their selenyl bromides by soaking in ~2% $Br_2/CH_2Cl_2$ for 10 minutes. The slides were rinsed with fresh methylene chloride and air-dried.

Preparation of Allyl Amides of Amino Acids for Attachment to Nitrone- or Selenyl Bromide-derivatized Microslides In a typical experiment, an N-Boc-protected alpha amino acid (0.5 mmol), PyBOP (0.5 mmol), DIPEA (0.5 mmol), and allylamine (0.5 mmol) in 5 mL $CH_2Cl_2$ was stirred for at least 12 hours. The reactions were then concentrated in vacuo and purified immediately by silica gel chromatography, using 6:1 EtOAc: Hex as eluant. Appropriate fractions were combined and concentrated to yield the desired Boc-protected allyl amides in yields generally greater than 90%. The amino acids investigated in this manner include alanine, proline, valine, phenylalanine, 3-amino-3-phenylpropionic acid, and 3-amino-5-hexenoic acid.

Attachment of Olefin-containing Molecules to Nitrone- or Selenyl Bromide-functionalized Microslides The allyl amides were taken up in DMF and dispensed to make solutions of each amino acid in steps of 10% ee. For nitrone-functionalized microslides, the amino acids were suspended in DMF at a concentration of 20 mM. For selenyl bromide-functionalized microslides samples were prepared to be 0.1 mM in a binary solvent system (v/v) of 1:199 DMF:toluene. The allyl amides were printed in the fashion described previously for N-Boc amino acids. Nitrone-functionalized plates were then incubated at 80° C. for 1 hour, cooled to room temperature, then deprotected by 5% TFA/$CH_2Cl_2$ for one hour, followed by deprotonation with 3% triethylamine in methylene chloride for 30 min.

Selenyl bromide-functionalized microslides were incubated at room temperature overnight. Deprotection was performed as described above for nitrone-functionalized microslides.

Acylation of Amino Acids Bound to Nitrone- or Selenyl Bromide-Functionalized Microslides Acylation was performed as described previously for amino acids using Cy3 and Cy5 as their pentafluorophenyl esters in DMF. Kinetic resolution is easily detectable on both nitrone- and selenyl bromide-functionalized microslides.

Acylation of Alcohols Using Cy3 and Cy5

A series of hydroxy acids were amide coupled to CMT-GAPS slides using PyBOP and DIPEA in DMF at concentrations of 50 mM and 10 mM. The compounds included D-lactic acid, L-lactic acid, (R)-3-hydroxybutyric acid, (S)-3-hydroxybutyric acid, (R)-3-hydroxy-3-phenylpropanoic acid, (S)-3-hydroxy-3-phenylpropanoic acid, and 4-(hydroxymethyl)-benzoic acid. The slides were incubated at room temperature overnight and then the residual amines were capped by amide coupling with acetic acid, PyBOP, and DIPEA in DMF. These capped microslides were washed with DMF, then rinsed with methylene chloride and dried in vacuo. Slides were then placed in a specially-designed glass apparatus which was constructed to maintain anhydrous conditions under an inert atmosphere. The slide and apparatus was placed under vacuum for a minimum of 12 hours, then exposed only to an atmosphere of dry argon gas.

A 2.9 mg sample of vacuum-dried Cy3:Cy5 (ratio=1:1) was taken up in 2 mL of anhydrous methylene chloride. In a separate flask was placed 17 mg dicyclohexylcarbodiimide (DCC) and 10 mg of N,N-dimethylaminopyridine (DMAP) and these were dissolved in 1 mL of anhydrous methylene chloride. To the DMAP/DCC solution was added 20 μL of the Cy3:Cy5 solution. The mixture was gently swirled, then pipetted under the microslide using a gas-tight syringe under an argon atmosphere. Approximately 700 μL of the fluorophore solution was pipetted into the reaction vessel, and the reaction was left for 12 hours at room temperature. The slide was washed with a 1:1 solution of methanolic methylene chloride for 20 minutes, followed by a one hour wash in methanol. The slides were then rinsed with methylene chloride and dried in vacuo. Scanning of the slides was performed as described above using the Axon scanner, whereby incorporation of fluorophores in all cases, and kinetic resolution for the chiral hydroxy acids, was easily discerned.

We claim:

1. A chiral detecting reagent comprising the structure (I):

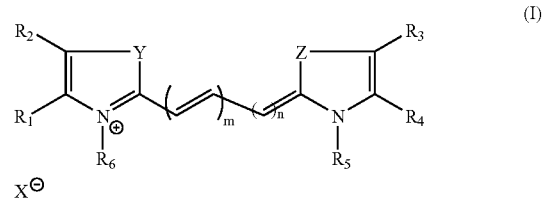

wherein $R_1$ and $R_2$, and $R_3$ and $R_4$ taken together each independently comprise a substituted or unsubstituted cyclic or polycyclic aryl or heteroaromatic moiety;
m is 1, 2, or 3;
n is 0 or 1;
Z or Y each independently comprise —O—, —S—, —Se—, —C(R)$_2$— or —NR—;
wherein each occurrence of the functional moiety R is independently selected from the group consisting of hydrogen and methyl;
X is a non-coordinating negative counter ion; and
$R_5$ and $R_6$ independently comprise lower alkyl, a chiral reagent (CR) or a chiral reagent and linker (L-CR), whereby said chiral reagent is attached to the detecting agent via the linker, with the proviso that at least one of $R_5$ and $R_6$ is a chiral reagent (CR) or a chiral reagent and linker (L-CR).

2. The chiral detecting reagent of claim 1, wherein $R_1$ and $R_2$ and $R_3$ and $R_4$ taken together each comprise a benzene moiety, $C_6H_6$; wherein each of Z and Y are —C(CH$_3$)$_2$; wherein the linker moiety comprises —(CH)$_p$—(CO)—; wherein p is 1–5, and wherein the chiral reagent comprises a chiral acylating agent having the general structure: —N(R')—CH(R$_x$)—COOH, where R$_x$ comprises an amino acid side chain, and R' is hydrogen, or R' and R$_x$ taken together with the nitrogen and carbon atoms to which they are respectively attached form a 5-membered heterocycle.

3. The chiral detecting reagent of claim 1, wherein $R_1$ and $R_2$ and $R_3$ and $R_4$ taken together each comprise a benzene moiety, $C_6H_6$.

4. The chiral detecting reagent of claim 1, wherein Z and Y are each —C(CH$_3$)$_2$.

5. The chiral detecting reagent of claim 1, wherein X is BF$_4$, PF$_6$, ClO$_4$, TsO, I or Br.

6. The chiral detecting reagent of claim 1, wherein one of $R_5$ and $R_6$ is methyl, and the other comprises a chiral reagent (CR) or a chiral reagent and linker (L-CR), whereby said chiral reagent is attached to the detecting agent via the linker.

7. The chiral detecting reagent of claim 1, 2, or 6, wherein the linker moiety comprises —(CH)$_p$—(CO)—; wherein p is 1–5.

8. The chiral detecting reagent of claim 1, wherein m and n are each 1.

9. The chiral detecting reagent of claim 1, wherein m is 2 and n is 1.

10. The chiral detecting reagent of claim 1, wherein the chiral agent comprises a chiral acylating agent.

11. The chiral detecting reagent of claim 10, wherein the chiral acylating agent has the general structure: —N(R')—CH(R$_x$)—COOH, where R$_x$ comprises an amino acid side chain; and R' is hydrogen, or R' and R$_x$ taken together the nitrogen and carbon atoms to which they are respectively attached form a 5-membered heterocycle.

12. The chiral detecting reagent of claim 11, wherein R' is hydrogen and R$_x$ is methyl, ethyl, iso-propyl, iso-butyl, tert-butyl, benzyl or cyclohexylmethyl.

13. The chiral detecting reagent of claim 11, wherein R' and R$_x$ taken together the nitrogen and carbon atoms to which they are respectively attached form a 5-membered heterocycle having the structure
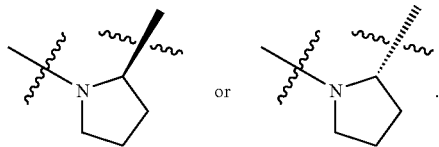
14. The chiral detecting reagent of claim 1, wherein the chiral reagent (CR) or the chiral reagent and linker (L-CR) is attached at any one of $R_1$–$R_6$, or as substitutions of other moieties thereof attached at $R_1$–$R_6$.
15. The chiral detecting reagent of claim 1, wherein p is 4.
* * * * *